US012668775B2

(12) United States Patent
Polo et al.

(10) Patent No.: US 12,668,775 B2
(45) Date of Patent: Jun. 30, 2026

(54) METHODS FOR REPROGRAMMING CELLS

(71) Applicants: Monash University, Clayton (AU); National University of Singapore, Singapore (SG); Nantes Université, Nantes (FR)

(72) Inventors: Jose Polo, Clayton (AU); Xiaodong Liu, Clayton (AU); Kathryn Davidson, Clayton (AU); Owen Rackham, Singapore (SG); John F. Ouyang, Singapore (SG); Laurent David, Nantes (FR); Gael Castel, Nantes (FR)

(73) Assignees: Monash University, Clayton (AU); National University of Singapore, Singapore (SG); NANTES UNIVERSITE, Nantes (FR)

( * ) Notice: Subject to any disclaimer, the term of this patent is extended or adjusted under 35 U.S.C. 154(b) by 938 days.

(21) Appl. No.: 17/776,506

(22) PCT Filed: Nov. 13, 2020

(86) PCT No.: PCT/AU2020/051235
§ 371 (c)(1),
(2) Date: May 12, 2022

(87) PCT Pub. No.: WO2021/092657
PCT Pub. Date: May 20, 2021

(65) Prior Publication Data
US 2022/0389376 A1 Dec. 8, 2022

(30) Foreign Application Priority Data
Nov. 13, 2019 (AU) ................................ 2019904283

(51) Int. Cl.
*C12N 5/073* (2010.01)

(52) U.S. Cl.
CPC ........ *C12N 5/0605* (2013.01); *C12N 2501/60* (2013.01); *C12N 2506/1307* (2013.01)

(58) Field of Classification Search
CPC ................................................... C12N 5/0605
See application file for complete search history.

(56) References Cited

U.S. PATENT DOCUMENTS 3,766,162 A 10/1973 Spector
3,791,932 A 2/1974 Schuurs et al.
(Continued)

FOREIGN PATENT DOCUMENTS

WO 2005/084158 9/2005
WO 2007/123667 11/2007
(Continued)

OTHER PUBLICATIONS

Ezashi (2011), Biology of Reproduction 85, 779-787 (Year: 2011).*
(Continued)

*Primary Examiner* — Mark L Shibuya
(74) *Attorney, Agent, or Firm* — McDonnell Boehnen Hulbert & Berghoff, LLP

(57) ABSTRACT

The present invention provides a method for reprogramming a human somatic cell to a cell exhibiting at least one characteristic of a trophoblast stem cell (TSC), the method comprising the following steps in order: a) increasing the protein expression of one or more factors in the somatic cell, wherein the factors are for reprogramming the somatic cell towards a pluripotent state; b) culturing the cell for a sufficient time and under conditions to allow the reprogramming of the cell towards a pluripotent state; c) contacting the cell with a culture medium suitable for sustaining trophoblast stem cells (TSC); and d) culturing the cell in the TSC medium for a sufficient time and under conditions to allow the cell to exhibit at least one characteristic of a TSC,
(Continued)

a)

b)

thereby reprogramming the somatic cell to a cell exhibiting at least one characteristic of a TSC.

21 Claims, 24 Drawing Sheets

(56)                    References Cited

U.S. PATENT DOCUMENTS

| | | | |
|---|---|---|---|
| 3,817,837 | A | 6/1974 | Rubenstein et al. |
| 4,233,402 | A | 11/1980 | Maggio et al. |
| 5,384,253 | A | 1/1995 | Krzyzek et al. |
| 5,580,859 | A | 12/1996 | Felgner et al. |
| 5,589,466 | A | 12/1996 | Felgner et al. |
| 5,656,610 | A | 8/1997 | Shuler et al. |
| 5,702,932 | A | 12/1997 | Hoy et al. |
| 5,736,524 | A | 4/1998 | Content et al. |
| 5,780,448 | A | 7/1998 | Davis |
| 5,789,215 | A | 8/1998 | Berns et al. |
| 5,945,100 | A | 8/1999 | Fick |
| 5,981,274 | A | 11/1999 | Tyrrell et al. |
| 5,994,624 | A | 11/1999 | Trolinder et al. |
| 6,730,293 | B1 | 5/2004 | Rothbard et al. |
| 2011/0136145 | A1 * | 6/2011 | Song ..................... C12N 5/16 |
| | | | 435/441 |

FOREIGN PATENT DOCUMENTS

| | | | | |
|---|---|---|---|---|
| WO | 2009/101407 | | 8/2009 | |
| WO | 2011/037270 | | 3/2011 | |
| WO | 2011/055851 | | 5/2011 | |
| WO | 2011/090221 | | 7/2011 | |
| WO | 2011/158967 | | 12/2011 | |
| WO | 2012/036299 | | 3/2012 | |
| WO | 2012/060473 | | 5/2012 | |
| WO | 2013/176233 | | 11/2013 | |
| WO | 2014/065435 | | 5/2014 | |
| WO | 2014/200030 | | 12/2014 | |
| WO | 2014/200114 | | 12/2014 | |
| WO | 2015/038704 | A1 | 3/2015 | |
| WO | 2016/005985 | | 1/2016 | |
| WO | WO-2016005985 | A2 * | 1/2016 | ........... C12N 5/0605 |
| WO | 2016/143866 | | 9/2016 | |

OTHER PUBLICATIONS

Okae, Jan. 4, 2018, Cell Stem Cell, vol. 22, pp. 50-63 (Year: 2018).*
Gao et al., "Establishment of porcine and human expanded potential stem cells", Nature Cell Biology, 2019; 21: 687-698.
Li et al., "Establishment of human trophoblast stem cells from human induced pluripotent stem cell-derived cystic cells under micromesh culture", Stem Cell Research & Therapy, 2019; 10, Article 245.
Liu et al., "Reprogramming roadmap reveals route to human induced trophoblast stem cells", Nature, 2020; 586 (7827): 101-107.
International Search Report mailed Jan. 19, 2021 in International Application No. PCT/AU2020/051235, filed Nov. 13, 2020, 4 pages.
Written Opinion mailed Jan. 19, 2021 in International Application No. PCT/AU2020/051235, filed Nov. 13, 2020, 5 pages.
Ezashi et al., "Generation of Colonies of Induced Trophoblast Cells During Standard Reprogramming of Porcine Fibroblasts to Induced Pluripotent Stem Cells", Biology of Reproduction, 2011, vol. 85, 779-787.
Okae et al., "Derivation of Human Trophoblast Stem Cells", Cell Stem Cell, 2018, vol. 22, 50-63.
Castel et al., "Induction of Human Trophoblast Stem Cells from Somatic Cells and Pluripotent Stem Cells", Cell Reports, 2020, vol. 33, 22 pages.
Castel et al., "Generation of human induced trophoblast stem cells", bioRxiv, 2020, 1-24.

Amita, Mitsuyoshi, et al. "Complete and unidirectional conversion of human embryonic stem cells to trophoblast by BMP4." Proceedings of the National Academy of Sciences 110.13 (2013): E1212-E1221.
Bredenkamp, Nicholas, et al. "Wnt inhibition facilitates RNA-mediated reprogramming of human somatic cells to naive pluripotency." Stem cell reports 13.6 (2019): 1083-1098.
Chen, Ying, et al. "Roles of CDX2 and EOMES in human induced trophoblast progenitor cells." Biochemical and biophysical research communications 431.2 (2013): 197-202.
Deglincerti, Alessia, et al. "Self-organization of the in vitro attached human embryo." Nature 533.7602 (2016): 251-254.
Eiselleova, Livia, et al. "A complex role for FGF-2 in self-renewal, survival, and adhesion of human embryonic stem cells." Stem cells 27.8 (2009): 1847-1857.
Elliott, Gillian, and Peter O'Hare. "Intercellular trafficking and protein delivery by a herpesvirus structural protein." Cell 88.2 (1997): 223-233.
Frankel, Alan D., and Carl O. Pabo. "Cellular uptake of the tat protein from human immunodeficiency virus." Cell 55.6 (1988): 1189-1193.
Gafni, Ohad, et al. "Derivation of novel human ground state naive pluripotent stem cells." Nature 504.7479 (2013): 282-286.
Green, Maurice, and Paul M. Loewenstein. "Autonomous functional domains of chemically synthesized human immunodeficiency virus tat trans-activator protein." Cell 55.6 (1988): 1179-1188.
Guo, Ge, et al. "Naive pluripotent stem cells derived directly from isolated cells of the human inner cell mass." Stem cell reports 6.4 (2016): 437-446.
Joliot, A. H., et al. "a-2, 8-Polysialic acid is the neuronal surface receptor of Antennapedia homeobox peptide." New Biol 3.11 (1991): 1121.
Joliot, Alain, et al. "Antennapedia homeobox peptide regulates neural morphogenesis." Proceedings of the National Academy of Sciences 88.5 (1991): 1864-1868.
Kidder, Benjamin L. "Derivation and manipulation of trophoblast stem cells from mouse blastocysts." Stem Cell Transcriptional Networks: Methods and Protocols (2014): 201-212.
Kilens, Stéphanie, et al. "Parallel derivation of isogenic human primed and naive induced pluripotent stem cells." Nature communications 9.1 (2018): 360.
Kuo, Hui-Hsuan, et al. "Negligible-cost and weekend-free chemically defined human iPSC culture." Stem Cell Reports 14.2 (2020): 256-270.
Le Roux, Isabelle, et al. "Neurotrophic activity of the Antennapedia homeodomain depends on its specific DNA-binding properties." Proceedings of the National Academy of Sciences 90.19 (1993): 9120-9124.
Lei, T., et al. "Influences of extracellular matrix and of conditioned media on differentiation and invasiveness of trophoblast stem cells." Placenta 28.1 (2007): 14-21.
Lindner, Scott E., and Bill Sugden. "The plasmid replicon of Epstein-Barr virus: mechanistic insights into efficient, licensed, extrachromosomal replication in human cells." Plasmid 58.1 (2007): 1-12.
Niakan, Kathy K., and Kevin Eggan. "Analysis of human embryos from zygote to blastocyst reveals distinct gene expression patterns relative to the mouse." Developmental biology 375.1 (2013): 54-64.
Petropoulos, Sophie, et al. "Single-cell RNA-seq reveals lineage and X chromosome dynamics in human preimplantation embryos." Cell 165.4 (2016): 1012-1026.
Rippe, R. A., D. A. Brenner, and H. L. Leffert. "DNA-mediated gene transfer into adult rat hepatocytes in primary culture." Molecular and Cellular Biology 10.2 (1990): 689-695.
Shahbazi, Marta N., et al. "Self-organization of the human embryo in the absence of maternal tissues." Nature cell biology 18.6 (2016): 700-708.
Stadtfeld, Matthias, and Konrad Hochedlinger. "Without a trace? PiggyBac-ing toward pluripotency." Nature Methods 6.5 (2009): 329-330.
Theunissen, Thorold W., et al. "Systematic identification of culture conditions for induction and maintenance of naive human pluripotency." Cell stem cell 15.4 (2014): 471-487.

(56) References Cited

OTHER PUBLICATIONS

Turco, Margherita Y., et al. "Trophoblast organoids as a model for maternal-fetal interactions during human placentation." Nature 564. 7735 (2018): 263-267.

Wilson, James M., et al. "Implantation of vascular grafts lined with genetically modified endothelial cells." Science 244.4910 (1989): 1344-1346.

Woltjen, Knut, et al. "piggyBac transposition reprograms fibroblasts to induced pluripotent stem cells." nature 458.7239 (2009): 766-770.

Wong, Tai-Kin, Claude Nicolau, and Peter Hans Hofschneider. "Appearance of β-lactamase activity in animal cells upon liposome-mediated gene transfer." Gene 10.2 (1980): 87-94.

Yang, Yang, et al. "Derivation of pluripotent stem cells with in vivo embryonic and extraembryonic potency." Cell 169.2 (2017): 243-257.

Yasuda, Shin-ya, et al. "Chemically defined and growth-factor-free culture system for the expansion and derivation of human pluripotent stem cells." Nature Biomedical Engineering 2.3 (2018): 173-182.

Yusa, Kosuke, et al. "Generation of transgene-free induced pluripotent mouse stem cells by the piggyBac transposon." Nature methods 6.5 (2009): 363-369.

* cited by examiner a)

b)

d) and e)

METHODS FOR REPROGRAMMING CELLS

RELATED APPLICATION

This application is a U.S. National Phase of International Application No. PCT/AU2020/051235 filed on Nov. 13, 2020, which claims priority from Australian provisional application AU 2019904283 filed on Nov. 13, 2019, the entire contents of which are hereby incorporated by reference.

FIELD OF THE INVENTION

The invention relates to methods and compositions for generating induced trophoblast stem cells from a cell.

BACKGROUND OF THE INVENTION

Mammalian embryogenesis begins with the totipotent zygote that is capable of developing into a blastocyst segregated by the inner cell mass (ICM) and the extraembryonic trophectoderm (TE). The ICM develops into the epiblast that yields the embryo proper and the primitive endoderm that generates the yolk sac. The TE eventually gives rises to the placenta.

The placenta is an important organ for human fetal development as the trophoblast cells in the placenta can mediate the interactions between the fetus and mother at the feto-maternal interface.

There are three main types of trophoblast derived cells that can be found in the human placenta: undifferentiated cytotrophoblasts (CTs), which can give rise to extravillous trophoblasts (EVTs) and syncytiotrophoblasts (STs). All of the trophoblast cells arise from the TE cells of the blastocyst and their well-controlled proliferation and differentiation are essential for fetal development. Impaired trophoblast development and function can lead to various complications during pregnancy, including miscarriage, preeclampsia and intrauterine growth restriction.

Despite the advances in research and clinical application of human pluripotent stem cells (hPSCs), including human embryonic stem cells (hESCs) and human induced pluripotent stem cells (hiPSCs), the development of reproducible methods for producing trophoblast stem cells has been lacking. Moreover, although derivation of TSCs has been achieved, isolating those cells from pre-implantation embryos or from placenta does not give access to genetic diversity.

There is a need for new and/or improved methods for generating human trophoblast stem cells, or cells displaying the characteristics of trophoblast stem cells that do not require pre-implantation embryos or placenta.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect, the present invention provides a method for reprogramming a somatic cell to a cell exhibiting at least one characteristic of a trophoblast stem cell (TSC), the method comprising the following steps in order:
  a) increasing the protein expression or amount of one or more factors in the somatic cell, wherein the factors are for reprogramming the somatic cell towards a de-differentiated or pluripotent state;
  b) culturing the cell for a sufficient time and under conditions to allow the reprogramming of the cell towards a de-differentiated or pluripotent state;
  c) contacting the cell with a TSC culture medium suitable for sustaining trophoblast stem cells (TSC); and
  d) culturing the cell in the TSC medium for a sufficient time and under conditions to allow the cell to exhibit at least one characteristic of a TSC,
  thereby reprogramming the somatic cell to a cell exhibiting at least one characteristic of a TSC.

Preferably, the TSC medium comprises a growth factor, preferably EGF, and a Rho-kinase (ROCK) inhibitor. Accordingly, the present invention also provides a method for reprogramming a somatic cell to a cell exhibiting at least one characteristic of a trophoblast stem cell (TSC), the method comprising the following steps in order:
  a) increasing the protein expression or amount of one or more factors in the somatic cell, wherein the factors are for reprogramming the somatic cell towards a de-differentiated or pluripotent state;
  b) culturing the cell for a sufficient time and under conditions to allow reprogramming of the cell towards a de-differentiated or pluripotent state;
  c) contacting the cell with a TSC culture medium comprising: a growth factor, preferably EGF, and a ROCK inhibitor; and
  d) culturing the cell in the TSC culture medium for a sufficient time and under conditions to allow the cell to exhibit at least one characteristic of a TSC,
  thereby reprogramming the somatic cell to a cell exhibiting at least one characteristic of a TSC.

The present invention also provides a method for producing a cell exhibiting at least one characteristic of a trophoblast stem cell (TSC) from a somatic cell, the method comprising the following steps in order:
  a) increasing the protein expression or amount of one or more factors in the somatic cell, wherein the factors are for reprogramming the somatic cell towards a de-differentiated or pluripotent state;
  b) culturing the cell for a sufficient time and under conditions to allow reprogramming of the cell towards a de-differentiated or pluripotent state;
  c) contacting the cell with a TSC culture medium comprising: a growth factor, preferably EGF, and a ROCK inhibitor; and
  d) culturing the cell in the TSC culture medium for a sufficient time and under conditions to allow the cell to exhibit at least one characteristic of a TSC,
  thereby producing a cell exhibiting at least one characteristic of a TSC from a somatic cell.

In a further embodiment, the invention provides a method for reprogramming a fibroblast, the method comprising the following steps in order:
  a) increasing the protein expression or amount of one or more factors in the fibroblast, wherein the factors are for reprogramming the fibroblast towards a de-differentiated or pluripotent state;
  b) culturing the cell for a sufficient time and under conditions to allow reprogramming of the cell towards a de-differentiated or pluripotent state;
  c) contacting the cell with a TSC culture medium comprising: a growth factor, preferably EGF, and a ROCK inhibitor; and

d) culturing the cell in the TSC culture medium for a sufficient time and under conditions to allow the cell to exhibit at least one characteristic of a TSC, wherein the fibroblast is reprogrammed to exhibit at least one characteristic of a TSC.

It will be understood that any method for reprogramming a somatic cell towards a de-differentiated or pluripotent state (i.e., methods for conducting steps a) and b) of the methods described herein) can be used in accordance with the methods of the present invention. As such, the present invention is not limited by the particular method for increasing the protein expression or amount of relevant factors, or culturing conditions, which can be used in accordance with steps a) and b), to allow the somatic cell to commence reprogramming towards plasticity or pluripotency. Such methods are known in the art and are further described herein.

In preferred embodiments, the factors for reprogramming the somatic cell towards a de-differentiated or pluripotent state are transcription factors. The transcription factors may comprise one or more of, or consist or consist essentially of the factors: OCT4, SOX2, KLF4 and MYC. In particularly preferred embodiments, the transcription factors comprise all four of the factors OCT4, SOX2, KLF4 and MYC (OSKM), or variants thereof.

Accordingly, in a preferred embodiment, the present invention provides:

In a further embodiment, the invention provides a method for reprogramming a fibroblast, the method comprising the following steps in order:

a) increasing the protein expression or amount of one or more of the transcription factors OCT4, SOX2, KLF4 and MYC (OSKM) in the fibroblast;

b) culturing the cell for a sufficient time and under conditions to allow reprogramming of the cell towards a de-differentiated or pluripotent state;

c) contacting the cell with a TSC culture medium comprising: EGF and a ROCK inhibitor; and d) culturing the cell in the TSC medium for a sufficient time and under conditions to allow the cell to exhibit at least one characteristic of a TSC, wherein the fibroblast is reprogrammed to exhibit at least one characteristic of a TSC.

In further embodiments, the transcription factors for reprogramming the somatic cell, e.g., fibroblast, towards a de-differentiated or pluripotent state may also comprise the factors LIN28 and/or NANOG. In certain embodiments, the protein expression of each of OCT4, SOX2, KLF4, MYC, LIN28 and NANOG is increased in the somatic cell.

Typically, the protein expression, or amount, of a transcription factor as described herein is increased by contacting the cell with an agent which increases the expression of the transcription factor. Preferably, the agent is selected from the group consisting of: a nucleotide sequence, a protein, an aptamer and small molecule, ribosome, RNAi agent and peptide-nucleic acid (PNA) and analogues or variants thereof. In some embodiments, the agent is exogenous. The present invention also contemplates the use of a transcriptional activation system (e.g., a gRNA for use in a gene activation system such as CRISPR/Cas9 or TALEN) for increasing the expression of the one or more transcription factors.

Typically, the protein expression, or amount, of a transcription factor as described herein is increased by introducing at least one nucleic acid comprising a nucleotide sequence encoding a transcription factor, or encoding a functional fragment thereof, in the cell.

In a preferred embodiment of the invention, the nucleic acid sequence encoding a transcription factor protein is introduced into a cell by a plasmid. One or more nucleic acids encoding one or more transcription factors may be used. Therefore, it is apparent that one or more plasmids may be used for the purpose of increasing the expression or amount of the required one or more transcription factors. In other words, the nucleic acid sequences may be in or on a single plasmid, or provided to the somatic cell in two or more plasmids.

In any embodiment of the present invention, the plasmid containing the nucleic acid encoding the one or more transcription factors for use according to the invention may be an episomal plasmid.

In any embodiment of the present invention, a detectable marker may also be introduced into the somatic cell to identify when the somatic cell has been reprogrammed to exhibit at least one characteristic of a TSC. The detectable marker may be a fluorescent reporter operably linked to a promoter or enhancer sequence.

Preferably, the nucleic acid further includes a heterologous promoter. Preferably, the nucleic acid is in a vector, such as a viral vector or a non-viral vector. Preferably, the vector is a viral vector comprising a genome that does not integrate into the host cell genome. The viral vector may be a retroviral vector, a lentiviral vector, an adenovirus or Sendai virus.

In any embodiment of the invention, the protein expression or amount of the factors is increased in the somatic cell by contacting the somatic cell with one or more agents for increasing the expression of said factors in the cell. In certain embodiments, the protein expression or amount of the factors is increased in the somatic cell by transduction or transfection of the somatic cell with one or more vectors encoding said transcription factors. The vector may be a viral vector, including an integrating or non-integrating viral vector. In further embodiments, the vector may be an episomal vector.

It will also be understood that the language "reprogramming towards a pluripotent state" does not require that the cell be pluripotent at the time of contacting with the TSC medium. In other words, the somatic cell does not need to have completed reprogramming to the pluripotent state prior to the step of contacting the cell with the TSC medium. Rather, the cell is preferably at an intermediate state, transitioning from differentiated state to a more plastic or less mature state (i.e., towards a non-differentiated or de-differentiated state) when it is contacted with the TSC medium.

Thus, the present invention further provides a method for reprogramming a somatic cell to a cell exhibiting at least one characteristic of a trophoblast stem cell (TSC), the method comprising the following steps in order:

a) increasing the protein expression or amount of one or more factors in the somatic cell, wherein the factors are for reprogramming the cell towards a de-differentiated or pluripotent state;

b) culturing the cell for a sufficient time and under conditions to allow the reprogramming of the cell to a reprogramming intermediate state between differentiation and pluripotency;

c) contacting the cell with a TSC culture medium suitable for sustaining trophoblast stem cells (TSC); and d) culturing the cell in the TSC medium for a sufficient time and under conditions to allow the cell to exhibit at least one characteristic of a TSC, thereby reprogramming the somatic cell to a cell exhibiting at least one characteristic of a TSC.

As used herein, reprogramming to an intermediate state between differentiation and pluripotency may also be understood to refer to reprogramming towards a less "mature" cell state.

In any embodiment, the period of time between increasing the protein expression or amount of the factors and contacting the cell with the TSC culture medium may be any period of time provided that it enables the reduction of markers associated with the somatic cell. In further examples, the period of time between increasing the protein expression or amount of the factors and contacting the cell with the TSC culture medium may be any period of time provided that it enables the cell to proceed through mesenchymal to epithelial transition states. In further or alternative embodiments, the period of time can be any period provided that it enables the upregulation of expression of trophectoderm (TE)-associated transcription factors in the cell. Examples of such transcription factors include: TFAP2C and GATA2.

In certain embodiments, the period of time for culturing the cell to commence reprogramming towards a de-differentiated or pluripotent state is at least 1 day following increasing the protein expression, or amount of the one or more factors. The period of time may be about 2, 3, 4, 5, 6, 7, 8, 9, 10, 11, 12, 13, 14, 15, 16, 17, 18, 19, 20, 21, 23, 25, 28, 30, 35, 42 or more days after increasing the protein expression, or amount of the one or more factors. In any embodiment, the period of time for culturing the cell to commence reprogramming towards a de-differentiated or pluripotent state may be any period of time provided that it enables the reduction of markers associated with the somatic cell.

In further embodiments of the invention, the methods above include culturing the cells towards a pluripotent state in a medium selected from: media suitable for culturing the somatic cell (e.g., fibroblast or similar media), primed pluripotency media, naïve pluripotency media or extended pluripotency media (e.g. LCDM media), prior to contacting and culturing the cells with TSC medium.

Still further, the methods above may include culturing the cells towards a pluripotent state in a primed medium, followed by transitioning the cells to a medium selected from: naïve media or extended media (e.g. LCDM media), and then contacting and culturing the cells with TSC medium.

The present invention also provides methods for obtaining TSCs from naïve and extended pluripotent stem cells.

Thus, in a further aspect, the present invention provides a method for generating a cell exhibiting at least one characteristic of a trophoblast stem cell (TSC), the method comprising the following steps in order:
- a) providing an established naïve pluripotent stem cell (iPSC) or extended induced pluripotent stem cell (EPSC);
- b) contacting the EPSC or naïve iPSC with a TSC culture medium comprising: a growth factor, preferably EGF, and a ROCK inhibitor; and
- c) culturing the cell in the TSC medium for a sufficient time and under conditions to allow the cell to exhibit at least one characteristic of a TSC,
- thereby reprogramming the EPSC or naïve iPSC to a cell exhibiting at least one characteristic of a TSC.

In any embodiment of the above aspect, the cell is an iPSC that has been obtained by reprogramming a somatic cell by any method known in the art. In preferred embodiments, the iPSC has been obtained from a reprogrammed fibroblast. In further embodiments, the iPSC has been obtained by reprogramming a fibroblast by increasing the expression of one or more of the transcription factors OCT4, SOX2, KLF4 and MYC (OSKM) in the fibroblast.

In a further aspect, the present invention provides a method for generating a cell exhibiting at least one characteristic of a trophoblast stem cell (TSC), the method comprising the following steps in order:
- a) providing an established primed extended pluripotent stem cell (EPSC) or naïve induced pluripotent stem cell (iPSC);
- b) contacting the EPSC or naïve iPSC with naïve media or LCDM media;
- c) contacting the EPSC or iPSC with a TSC culture medium comprising: a growth factor, preferably EGF, and a ROCK inhibitor; and
- d) culturing the cell in the TSC medium for a sufficient time and under conditions to allow the cell to exhibit at least one characteristic of a TSC,
- thereby reprogramming the EPSC or naïve iPSC cell to a cell exhibiting at least one characteristic of a TSC.

In any embodiment of the above aspect, the cell is a naïve iPSC/EPSC that has been obtained by reprogramming a somatic cell by any method known in the art. In preferred embodiments, the naïve iPSC/EPSC has been obtained from a reprogrammed fibroblast or other somatic cell type. In further embodiments, the iPSC has been obtained by reprogramming a fibroblast by increasing the expression of one or more of the transcription factors OCT4, SOX2, KLF4 and MYC (OSKM) in the fibroblast.

In any embodiment of the invention, the TSC culture media comprises the ROCK inhibitor trans-N-(4-pyridyl)-4-(1-aminoethyl)-cyclohexanecarboxamide (Y-27632), or a salt thereof.

In further embodiments, the TSC culture medium additionally comprises one or more of:
4-[4-(1,3-benzodioxol-5-yl)-5-(2-pyridyl)-1H-imidazol-2-yl] benzamide (SB 431542) or a salt thereof;
6-[[2-[[4-(2,4-dichlorophenyl)-5-(4-methyl-1H-imidazol_2-yl)-2-pyrimidinyl]amino]ethyl]amino]micotinonitrile (CHIR 99021), or a salt thereof; and/or
A83-01 (3-(6-Methyl-2-pyridinyl)-N-phenyl-4-(4-quinolinyl)-1H-pyrazole-1-carbothioamide), or a salt thereof;

In further embodiments, the TSC medium also comprises an agent for stimulating Wnt and one or more inhibitors of TGFβ.

In preferred embodiments, the TSC culture comprises: A83-01, SB431542, EGF, CHIR, a ROCK inhibitor, ascorbic acid and valproic acid. (The media may also be referred to as ASECRiAV).

As used herein, a characteristic of a TSC will be understood to include:
an undifferentiated, bipotential state and the ability to differentiate into a cell exhibiting one or more characteristics of an extravillous trophoblast (EVT) or syncytiotrophoblast (ST);
cobblestone-shaped colony appearance;
a methylation pattern similar to a blastocyst-derived TSC, as determined by a bisulfite assay or genome-wide DNA methylation profiling techniques;
the expression of one or more biochemical markers of a TSC, as determined by an immunohistochemistry and/or PCR assay, preferably wherein the markers are selected from the group consisting of: CD249 (aminopeptidase A), CD49f (ITGA6); nuclear GATA2/3, TFAP2C, P63 and NR2F2;
the level of chromatin accessibility similar to blastocyst-derived TSC, as determined using ATAC-seq;

a histone modification profile similar to blastocyst-derived TSC, (eg, H3K4me3, H3K27ac gene modification);

a proteome or metabolome profile similar to blastocyst-derived TSC.

In further embodiments, a cell exhibiting at least one characteristic of a TSC is characterised by an absence of the markers characterising the somatic cell. In certain embodiments, the cell exhibiting at least one characteristic of a TSC does not express one or more of the following markers: OCT4 (also called POU5F1), NANOG, SOX2, SALL2, OTX2, BANCR, KLF17, DPPA3, ARGFX and DNMT3L.

In any embodiment, the TSC cells made according to the present invention are characterised by at least one, at least two, at least three, at least four, or at least five characteristics of a TSC as herein described.

In preferred embodiments, the methods defined herein are for reprogramming of a somatic cell to a cell that:

has the ability to differentiate into a cell exhibiting one or more characteristics of an extravillous trophoblast (EVT) or syncytiotrophoblast (ST); and expresses one or more biochemical markers of a TSC selected from the group consisting of: nuclear GATA2/3, TFAP2C, P63 and NR2F2.

As used herein, a characteristic of an ST includes one or more of: SDC1+ multinucleated cells, and increased expression of one or more of the markers CGA, CGB, PSG1, CSH1, HSD3B1, CYP19A1, SDC1 and INHA relative to a TSC.

As used herein, a characteristic of an EVT includes one or more of: increased expression of one or more of the markers HLA-G, PRG2, PAPPA2, MMP2, ITGA5 and ATGA1 relative to a TSC.

In further embodiments, the cell exhibiting at least one characteristic of a TSC retains its undifferentiated state when maintained in subculture.

Preferably, the cell having at least one characteristic of a TSC retains the at least one characteristic of a TSC for at least 5, at least 10, at least 15, at least 20, at least 40 or more cell culture passages.

A somatic cell may be any cell type described herein, including a diseased cell. The somatic cell may be an adult cell or a cell derived from an adult which displays one or more detectable characteristics of an adult or non-embryonic cell. The diseased cell may be a cell displaying one or more detectable characteristics of a disease or condition.

In preferred embodiments, the somatic cell is a fibroblast.

Typically, conditions suitable for reprogramming of a somatic cell include culturing the cells for a sufficient time and in a suitable medium. A sufficient time of culturing may be at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days.

In any method described herein, the method may further include the step of expanding the cells exhibiting at least one characteristic of a TSC to increase the proportion of cells in the population exhibiting at least one characteristic of a TSC. The step of expanding the cells may include culturing the cells for a sufficient time and under conditions for generating a population of cells as described below.

In any method described herein, the method may further include the step of differentiating the cells exhibiting at least one characteristic of a TSC to generate a cell exhibiting at least one characteristic of an EVT or an ST. The step of differentiating the cells may include culturing the cells for a sufficient time and under conditions for generating a cell having at least one characteristic of an EVT or ST as described herein.

Still further, the methods may further include differentiating a cell exhibiting at least one characteristic of a TSC, to an extra-placental cell type, for use in regenerative medicine.

The present invention also provides a mammalian undifferentiated progenitor cell having at least one characteristic of a TSC, wherein the cell is obtained by any method as defined herein.

The present invention also provides a cell exhibiting at least one characteristic of a TSC produced by a method as described herein.

In any method described herein, the method may further include the step of isolating the cell exhibiting at least one characteristic of the TSC.

Accordingly, in a further embodiment, there is provided an isolated TSC obtainable, or obtained by any method described herein.

The invention also provides an isolated EVT or ST derived or differentiated from a cell exhibiting at least one characteristic of a TSC, obtained according to the methods of the present invention.

The present invention also provides a population of cells, wherein at least 5% of cells exhibit at least one characteristic of a TSC and those cells are produced by a method as described herein. Preferably, at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the cells in the population exhibit at least one characteristic of a TSC.

The present invention also provides a population of cells, wherein at least 5% of the cells are STs or EVTs differentiated from cells that exhibit at least one characteristic of a TSC produced by a method as described herein. Preferably, at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% of the cells in the population are STs or EVTs obtained by differentiating a cell exhibiting at least one characteristic of a TSC obtained according to the present invention.

The invention also provides a pharmaceutical composition comprising:

a cell exhibiting at least one characteristic of a TSC, wherein the cell is obtained or obtainable according to the methods of the present invention, and a pharmaceutically acceptable excipient.

The invention also provides a pharmaceutical composition comprising:

a cell exhibiting at least one characteristic of an ST or EVT, wherein the cell is obtained or obtainable by differentiating a cell having at least one characteristic of a TSC obtained or obtainable according to the methods of the present invention, and a pharmaceutically acceptable excipient.

The invention also provides a composition, including a homeopathic, or dietary supplement comprising:

a cell or population of cells exhibiting at least one characteristic of a TSC, wherein the cell is obtained or obtainable according to the methods of the present invention, and/or a cell or population of cells exhibiting at least one characteristic of an ST or EVT, wherein the cell is obtained or obtainable by differentiating a cell having at least one characteristic of a TSC obtained or obtainable according to the methods of the present invention, and/or an organoid derived from a cell or population of cells exhibiting at least one characteristic of an ST or EVT, wherein the cell is obtained or obtainable by differentiating a cell having at least one characteristic of a TSC obtained or obtainable according to the methods of the present invention;

and a pharmaceutically acceptable excipient.

The invention further provides a composition, including a homeopathic, or dietary supplement derived from:

a cell or population of cells, exhibiting at least one characteristic of a TSC, wherein the cell is obtained or obtainable according to the methods of the present invention, and a cell or population of cells exhibiting at least one characteristic of an ST or EVT, wherein the cell is obtained or obtainable by differentiating a cell having at least one characteristic of a TSC obtained or obtainable according to the methods of the present invention, and an organoid derived from a cell or population of cells exhibiting at least one characteristic of an ST or EVT, wherein the cell is obtained or obtainable by differentiating a cell having at least one characteristic of a TSC obtained or obtainable according to the methods of the present invention.

Uses

In any method described herein, the method may further include the step of administering:

a cell exhibiting at least one characteristic of a TSC made according to a method described herein, or a cell population including a cell exhibiting at least one characteristic of a TSC made according to a method described herein, or a differentiated cell or population of differentiated cells, obtained from a cell exhibiting at least one characteristic of a TSC made according to the present invention, to a subject in need thereof.

In some embodiments, there is provided a method of augmenting a placenta or blastocyst comprising introducing into a placenta or blastocyst:

a cell exhibiting at least one characteristic of a TSC generated according to the methods described herein;

a cell population including a cell exhibiting at least one characteristic of a TSC made according to a method described herein, or a differentiated cell or population of differentiated cells, obtained from a cell exhibiting at least one characteristic of a TSC made according to the present invention.

The invention also provides for an organoid obtained from cells exhibiting at least one characteristic of a TSC made according to a method described herein and/or differentiated cells (e.g., STs or EVTs) obtained from cells exhibiting at least one characteristic of a TSC made according to a method described herein.

In further aspects, there is provided a method of treating and/or preventing a disorder associated with the development and/or activity of trophoblasts in a subject in need thereof, the method comprising administering to the subject a therapeutically effective amount of a cell or population of cells exhibiting at least one characteristic of a TSC made according to a method described herein, a differentiated ST or EVT obtained from cells exhibiting at least one characteristic of a TSC made according to a method described herein, or pharmaceutical product according to the invention, thereby treating and/or preventing the disorder associated with the development and/or activity of trophoblasts in the subject.

The present invention also provides a use of a cell, or cell population including a cell produced according to the instant invention, exhibiting at least one characteristic of a TSC, in the manufacture of a medicament for the treatment of a disease/disorder of the placenta. For example, the reprogrammed cells of the instant invention may be introduced (transplanted) to an individual in order to improve a disease or condition of the placenta. Alternatively, the cells exhibiting at least one characteristic of a TSC can be differentiated prior to use in the manufacture of a medicament as herein described.

In any embodiment of the above aspects, the disease is selected from the group consisting of: recurrent miscarriage, preeclampsia, fetal growth restriction (FGR), hydratiform mole and choriocarcinoma. The present invention also provides a method of identifying an agent capable of modulating trophoblast development and/or activity, the method comprising:

contacting an isolated TSC or placenta made according to the present invention with a candidate agent;

comparing development and/or activity of the isolated TSC or placenta following the contacting with the agent, to the development and/or activity of the TSC or placenta without the agent wherein the effect of the agent on the development and/or activity of the TSC or placenta above a predetermined level relative to the development of the TSC or placenta without the agent is indicative that the agent modulates trophoblast development and/or activity.

Further, the present invention provides a method for obtaining a compound produced by a trophoblast, the method comprising culturing a cell, or population of cells comprising at least one characteristic of a TSC according to the present invention, or a culture comprising the same, and isolating from the culture medium a compound secreted by the cells, thereby obtaining the compound produced by the trophoblast.

The present invention also provides a method for obtaining a compound or particle secreted by an EVT or ST, the method comprising culturing an ST or EVT, or population of STs or EVTs obtained by differentiating a cell comprising at least one characteristic of a TSC according to the present invention, and isolating from the culture medium a compound or particle secreted by the cells, thereby obtaining the compound or particle produced by the EVT or ST.

The compound may be a hormone or growth factor. The particle secreted by the cell may be an extracellular vesicle, such as an exosome.

The present invention also relates to kits for producing a cell exhibiting at least one characteristic of a TSC as disclosed herein. In some embodiments, a kit comprises a somatic cell, reprogramming factors, and TSC culture medium as disclosed herein. Preferably, the kit can be used to produce a cell exhibiting at least one characteristic of a TSC. Preferably, the kit can be used with a somatic cell that is a fibroblast. In some embodiments, the kit further comprises instructions for reprogramming a somatic cell to a cell exhibiting at least one characteristic of a TSC according to the methods as disclosed herein. Preferably, the present invention provides a kit when used in a method of the invention described herein.

The kit may also comprise one or more agents suitable for differentiating the TSCs towards an EVT or ST fate, or other non-placental differentiated cell type.

Any method as described herein may have one or more, or all, steps performed in vitro, ex vivo or in vivo.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

Figure 2:
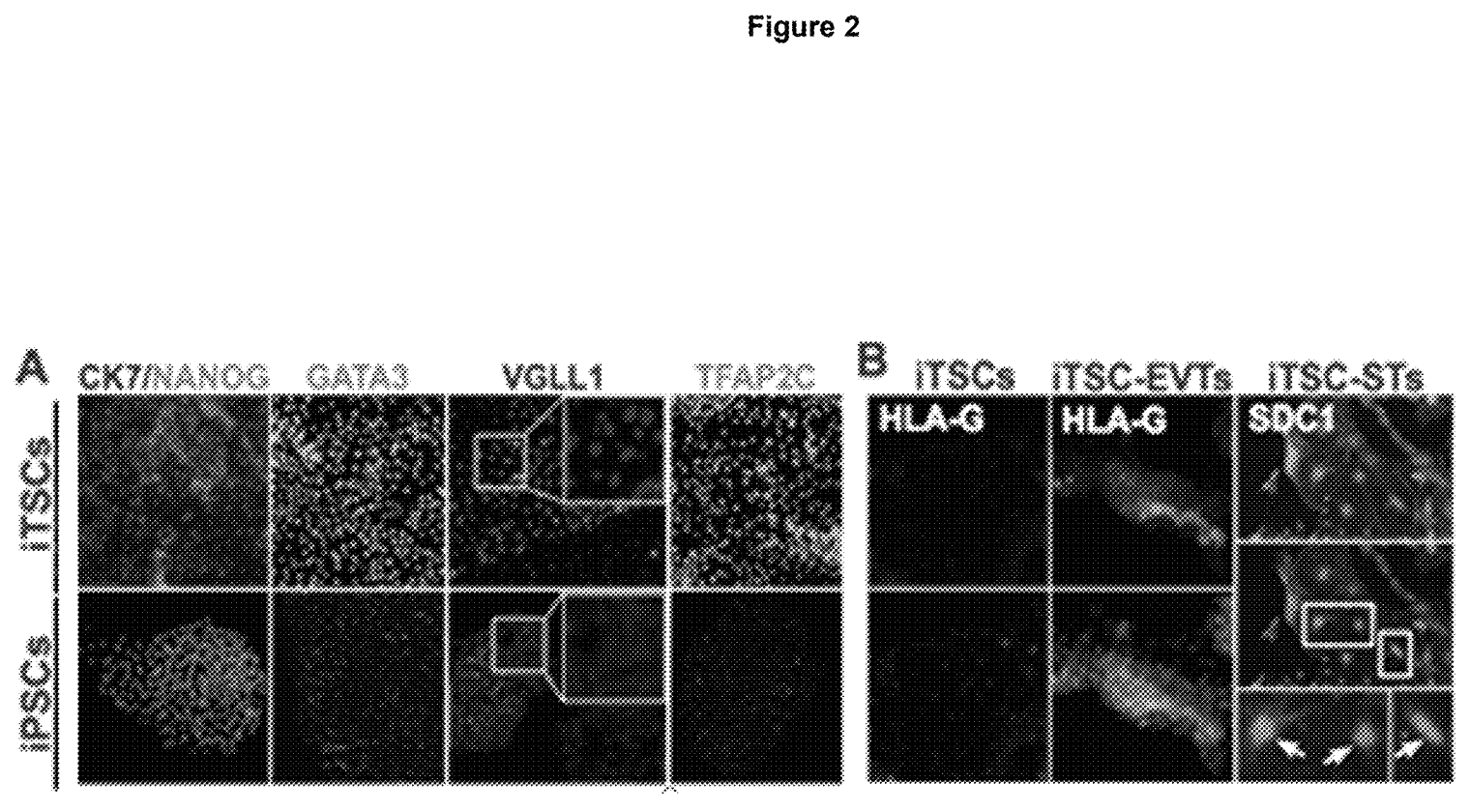

FIG. 2: Characterization of iTSCs. A) Immunofluorescent (IF) labelling confirms iTSCs express TE markers CK7, GATA3, nuclear VGLL1 & TFAP2C and do not express NANOG (PSC marker). B) iTSC-derived EVTs express HLA-G; iTSC-STs express SDC1 and exhibit multi-nucleation (arrows). DAPI nuclear stain in blue.

and HLA-G in iTSCd8 EVT and iTSCd21n EVT. (r, s) Expression of ST genes in iTSCd8- and iTSCd21n-derived ST cells (r) and expression of EVT genes in iTSCd8 and iTSCd21n-derived EVT cells (s). (t) Representative hCG test from urine samples collected from iTSCd8-injected mice, n=3. (u) Lesions collected from subcutaneously engrafted iTSCd8 in NOD-SCID mice, n=4. (v) hCG protein level detected by hCG ELISA using mouse blood serum samples, n=4. (w) Haematoxylin and eosin (H&E) and immunohistochemical staining of KRT7, SDC1 and HLA-G in the lesions collected from iTSCd8 engrafts in NOD-SCID mice, n=4. No lesions were evident in vehicle controls. Scale bar, 200 μm.

Figure 6:
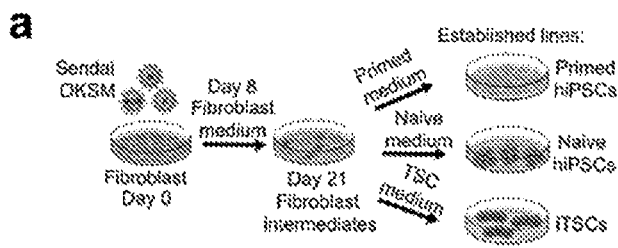
Figure 6:
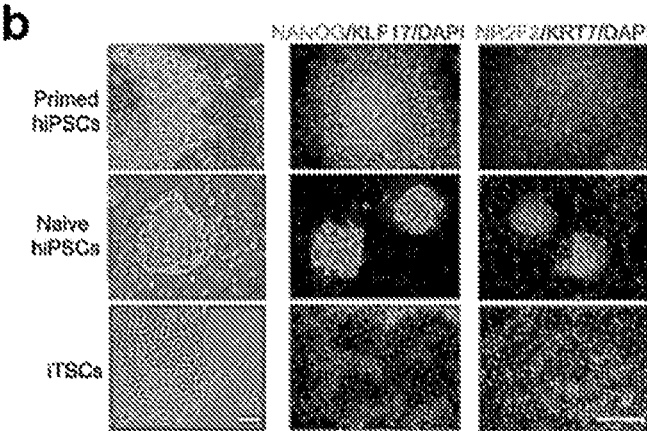
Figure 6:
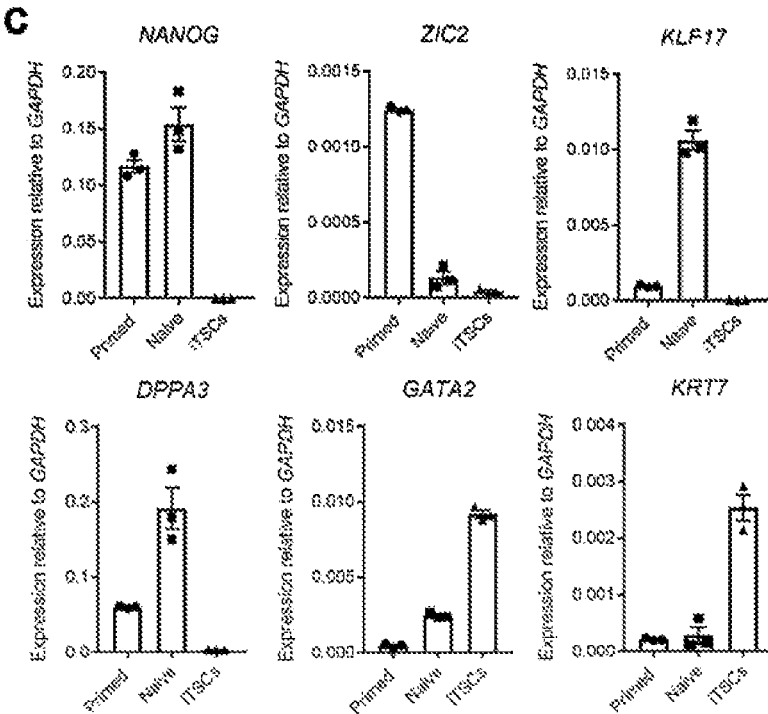

FIG. 6: Derivation of iTSCs from day21 human fibroblast reprogramming intermediates. (a) Experimental designs to validate the potential of day-21 fibroblast reprogramming intermediates for the derivation of primed, naive iPSCs and iTSCs. (b) Phase-contrast images of primed, naive iPSCs and iTSCs generated from day 21 fibroblast reprogramming intermediates, n=2. Scale bar, 50 μm. Immunostaining of primed, naive iPSCs and iTSCs with NANOG, KLF17, NR2F2, KRT7 and DAPI for nuclei staining, n=2. Scale bar, 200 μm. (c) Reverse-transcription qPCR analysis of NANOG, ZIC2, KLF17, DPPA3, GATA2 and KRT7 expression in primed, naive iPSCs and iTSCs generated from day-21 fibroblast reprogramming intermediates, n=3. Data are mean±s.e.m.

Figure 7:
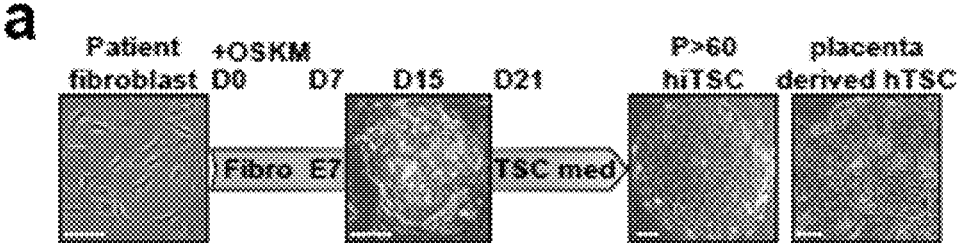
Figure 7:
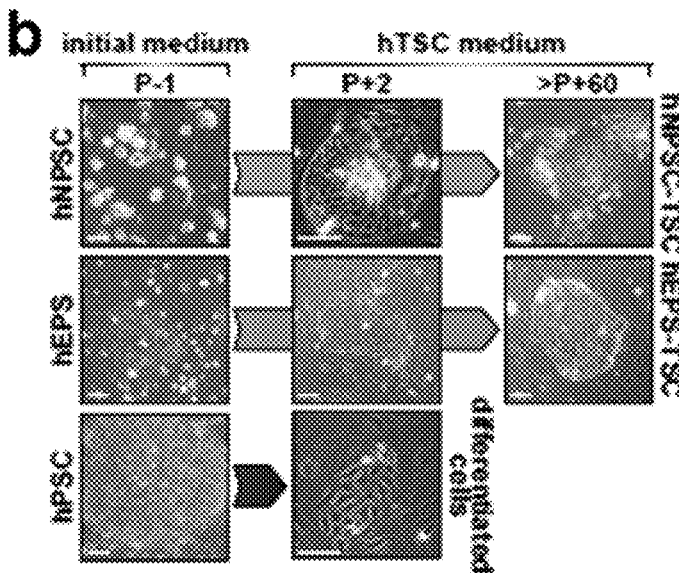
Figure 7:
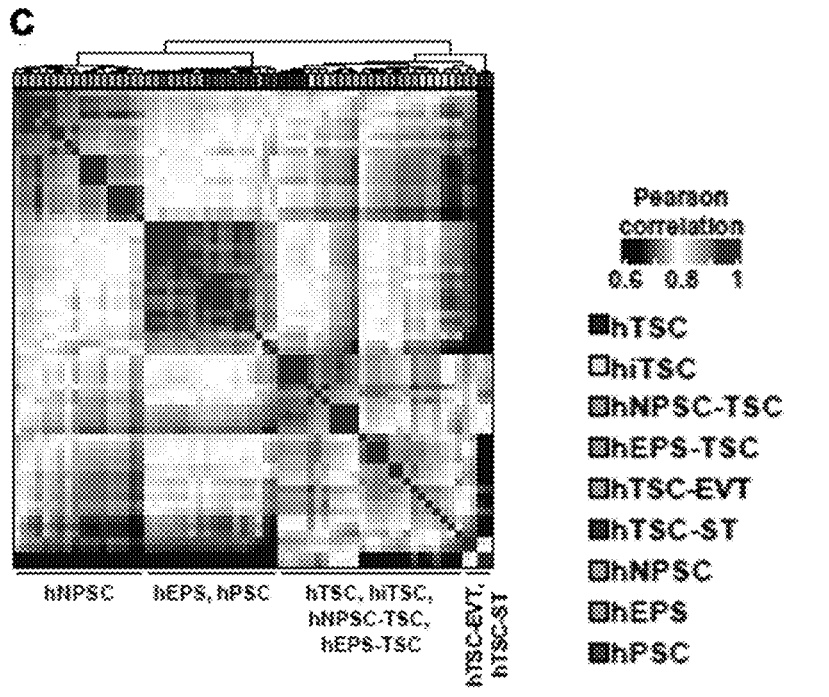
Figure 7:
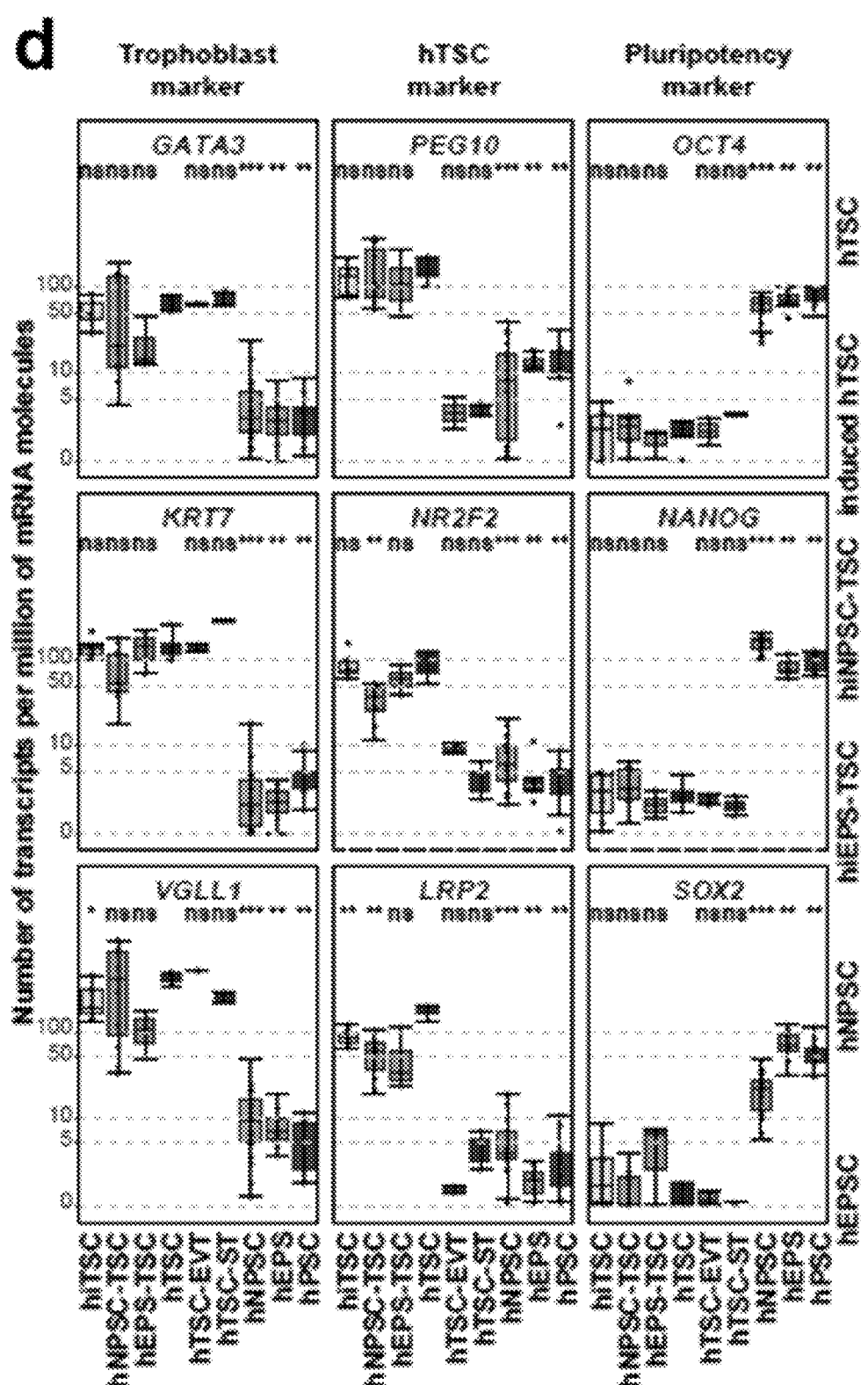
Figure 7:
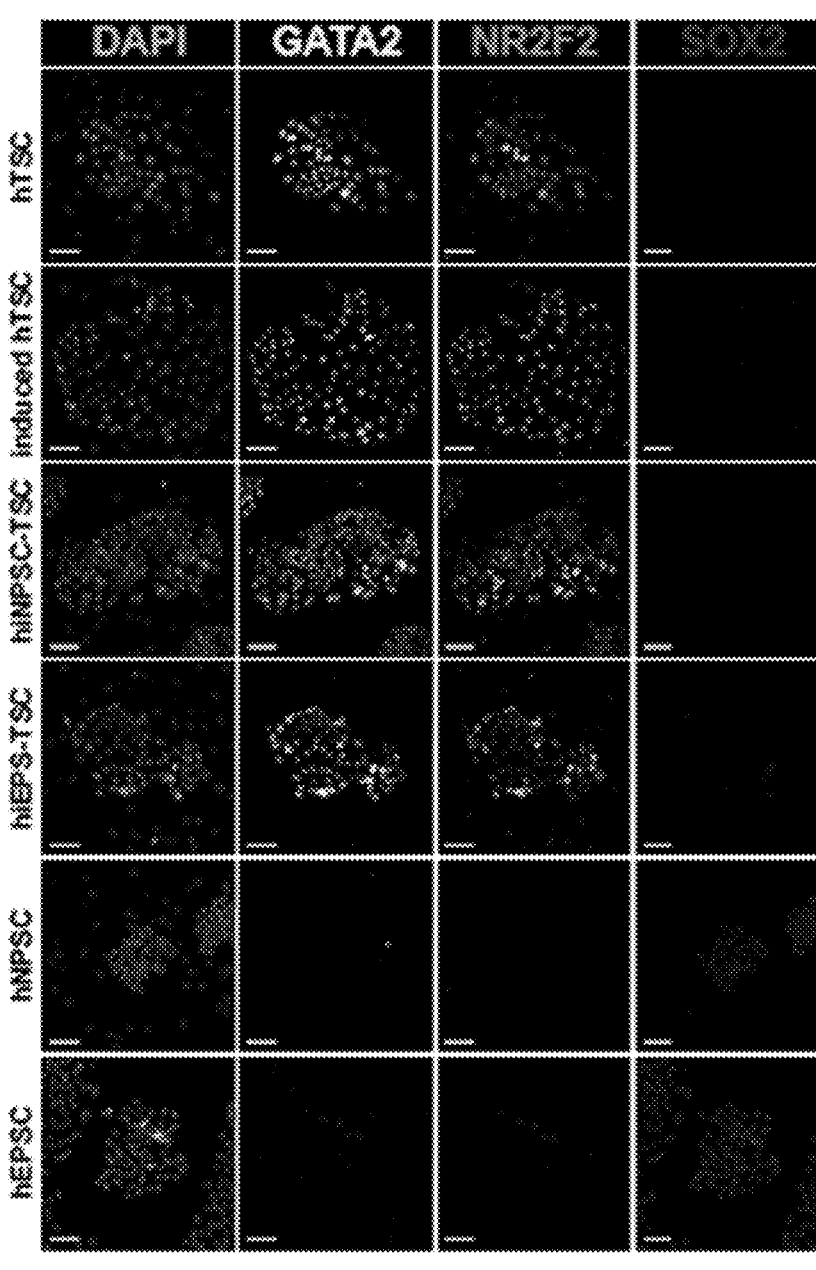
Figure 7:
Figure 7:
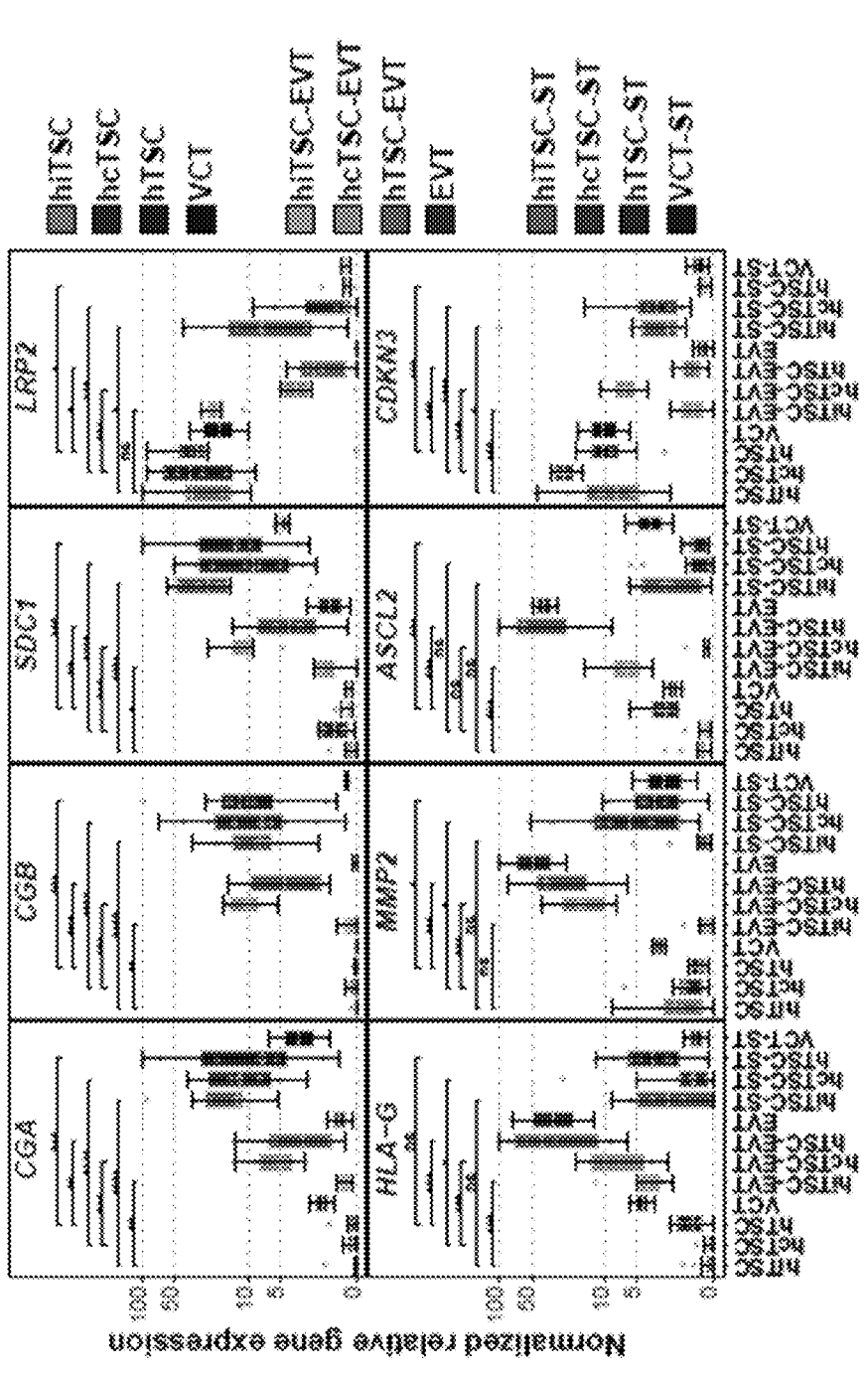
Figure 7:
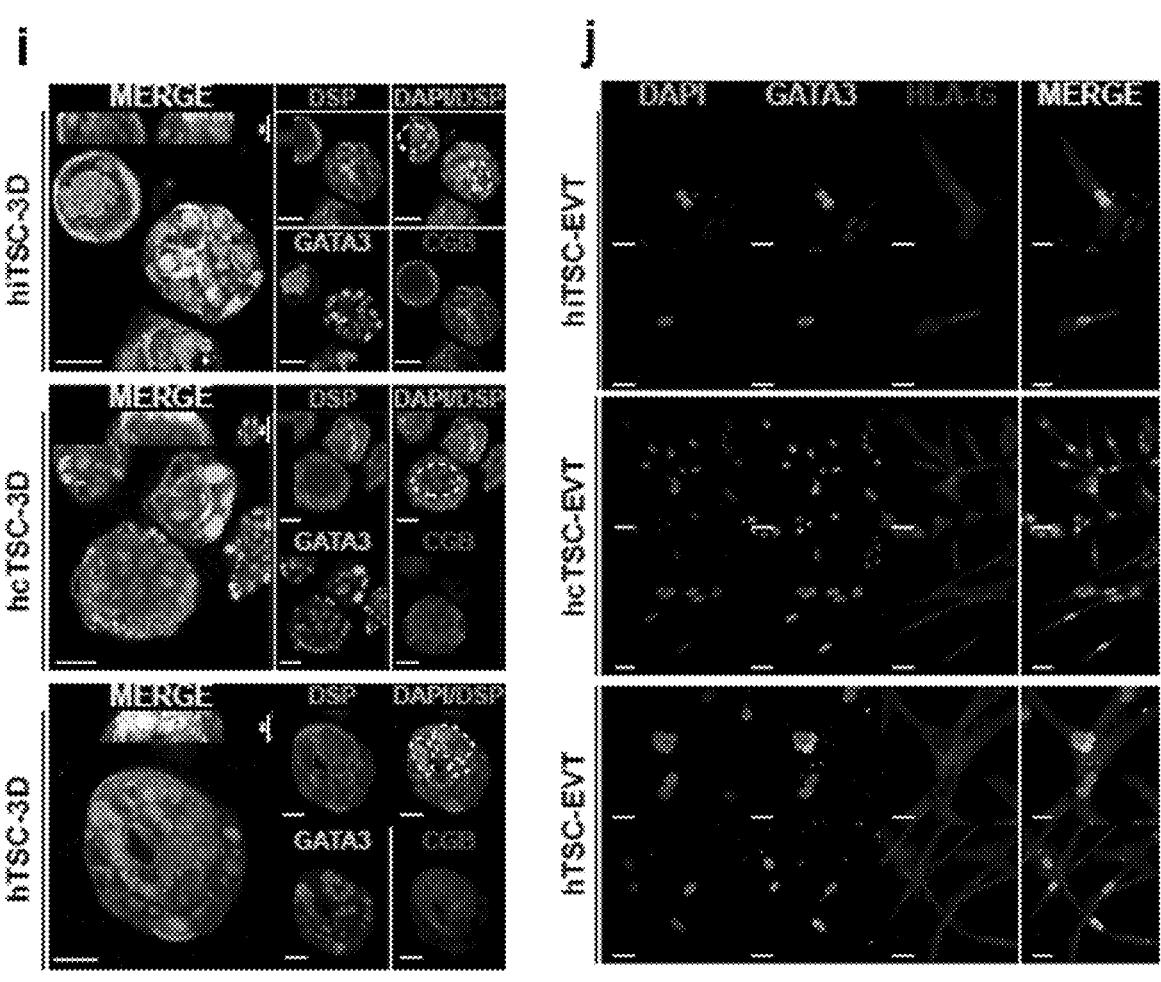

FIG. 7: Derivation of iTSCs from partially reprogrammed intermediates, conversion of naive and extended iPSCs into TSCs. (a) Schematic representation of the reprogramming protocol. Phase contrast pictures show the changes in cell morphology. Placenta-derived hTSC are shown as controls. (b) Schematic representation of the conversion protocol. Phase contrast pictures show the changes in cell morphology. (c) Heatmap of Pearson correlation coefficients of hPSC, hEPS, hNPSC, hiTSC, hcTSC and hTSC lines along with ST and EVT differentiated from hTSC. Correlations are determined from the comparison of the 2770 most over dispersed genes of the dataset (see Methods). Samples are clustered from the Euclidean distance of correlations, by a hierarchical clustering using Ward's method. (d) Gene expression levels of indicated lineage markers are shown for hPSC, hEPS, hNPSC, hiTSC, hcTSC and previously-established embryo- and placenta-derived hTSC lines. The differentiated ST and EVT are included as controls. Expression levels are given as the number of transcripts per million of mRNA molecules. A Wilcoxon-Mann-Whitney statistical test was performed for each type of hPSC and hTSC, with embryo- and placenta-derived hTSC taken as the reference group. Stars indicate statistical significance of the difference: *p-value<0.05; p-value<0.01; *p-value<0.001. (e) Immunofluorescence images of hTSC, hiTSC, hcTSC, hNPSC and hEPS stained for trophoblast-associated transcription factors GATA2 and NR2F2 and pluripotency associated transcription factor SOX2. Nuclei were stained with DAPI. Scale bars: 100 μm. (f) Schematic representation of the EVT differentiation protocol (left). Bright field pictures of the EVT progeny of h(i/c)TSC (right). (g) Schematic representation of the 3D-ST differentiation protocol (left). Bright field pictures of the 3D-ST structures derived from h(i/c)TSC (right). (h) RT-qPCR quantification of markers associated with ST (CGA, CGB, SDC1), EVT (HLA-G, MMP2, ASCL2) and hTSC (LRP2, CDKN3). A Wilcoxon-Mann-Whitney statistical test was performed for each type of hTSC and the differentiated cell progeny. Stars indicate statistical significance of the difference: *p value<0.05; p-value<0.01; *p-value<0.001. (i) Immunofluorescence images of 3D-ST structures derived from hiTSC, hcTSC and hTSC lines stained for GATA3 and the membrane-associated protein desmoplakin (DSP) highlighting syncytia, along with the syncytiotrophoblast-associated marker CGB. Nuclei were stained with DAPI. (j) Immunofluorescence images of EVT differentiated from hiTSC, hcTSC and placenta-derived hTSC lines stained for the trophoblast-associated transcription factor GATA3 and the extravillous trophoblast-specific surface marker HLA-G. Nuclei were stained with DAPI. Scale bars (f-g): 100 μm; (i-j): 30 μm.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

For purposes of interpreting this specification, terms used in the singular will also include the plural and vice versa.

The present invention is directed to a new method for generating human trophoblast stem cells (hTSCs) directly from somatic cells by nuclear reprogramming. To date, the only published methods for generating TSCs include isolation of TSCs from primary tissues (e.g., first-trimester placenta or blastocyst), or by differentiating "expanded potential stem cells" (EPSCs) into TSCs. The present invention enables the generation of human "induced" trophoblast stem cells (iTSCs) from easy-to-access patient-specific sources (e.g., fibroblasts), and therefore removes the reliance on obtaining tissue sources of such cells (such as placenta) or the difficult-to-generate EPSCs.

Whilst studying the reprogramming of fibroblasts into different pluripotent states, the present inventors identified an intermediate cell population that transiently upregulates the trophectoderm (TE) transcriptional network. By stabilising the intermediate TE state and shifting reprogramming cells out of pluripotency media and into media that can support TSCs, the inventors have devised a method for generating "induced trophoblast stem cells" (iTSCs) from somatic cells.

Characterization of the iTSCs produced according to the inventors' methods shows that these cells express key factors that define human TE and TSCs. For example, the cells express nuclear NR2F2, which marks PCNA+ proliferating cells in human placenta. TSCs produced according to the present invention are proliferative, and maintain their TSC characteristics through multiple passages without a reduction in growth rate. Moreover, these cells strongly resemble TSCs derived from human blastocyst or first-trimester placentas, both molecularly and functionally. Functional characterisation of the TSCs generated according to the methods of the present invention demonstrate that these cells are capable of being differentiated into either syncytiotrophoblasts (STs) or extravillous trophoblasts cells (EVTs). Importantly, these assays demonstrate that the iTSCs generated according to the methods of the invention are indeed bipotential and can differentiate into ST cells and EVT cells.

Human trophoblast stem cells (TSCs) derived from primary placental tissues or human blastocysts are difficult to access and are highly regulated. Accordingly, having stable self-renewing iTSC lines that can be derived from adult cells provides a unique opportunity not only to study human trophoblast development, but also its relationship with pluripotent cells and its role in coordinating events associated with early human embryogenesis in an in vitro context where modern biochemical and molecular techniques can be applied at scale. The iTSC lines can also be used for disease modeling, drug screening and regenerative medicine. Further, iTSCs may be useful for generating organoids resembling the placenta.

Cells produced according to the present invention may also find utility in a variety of other clinical applications, including for generating trophoblast organoids to investigate maternal-fetal transmission of xenobiotics, drugs and pathogens, proteins and hormones. Further, human TSCs/iTSCs and iPSCs derived from somatic cells of the same healthy individual or patient may be used to assemble human blastocyst-like structures. This provides an unlimited source of synthetic human blastocyst-like organoids for large scale screening studies, including for the treatment of infertility and to improve the rate of success of IVF. Still further, the iTSCs produced according to the present invention can be used in regenerative medicine. For example, placental cells have recently been shown to be useful in regenerating heart tissue. The iTSCs of the present invention can be used to generate such placenta cells, without the need to obtain cells from placenta directly.

Compared to current methods of deriving human TSCs from human placentas or human embryos, the reprogramming approach of the present invention, for generating human iTSCs is more accessible, labor and cost effective, with no ethical restrictions. This approach allows unlimited supply of isogenic iTSCs for large scale screening studies using disease-specific iTSCs generated from the patients. Cells A cell for use in accordance with the methods of the present invention may be any cell type described herein, including a somatic cell or a diseased cell. The somatic cell may be an adult cell or a cell derived from an adult which displays one or more detectable characteristics of an adult or non-embryonic cell. The diseased cell may be a cell displaying one or more detectable characteristics of a disease or condition.

The somatic cell for use in accordance with the present invention may be derived from an iPSC or other embryonic or adult stem cell or may be derived from a tissue explant from a subject.

In preferred embodiments, the somatic cell is a fibroblast (preferably a dermal fibroblast or a cardiac fibroblast), a keratinocyte (preferably epidermal keratinocyte), a monocyte or an endothelial cell.

As used herein, the term "stem cell" refers to a cell which is not terminally differentiated, i.e., it is capable of differentiating into other cell types having a more particular, specialised function. The term encompasses embryonic stem cells, fetal stem cells, adult stem cells or committed/progenitor cells.

As used herein, a "somatic cell" refers to a terminally differentiated cell. As used herein, the term "somatic cell" refers to any cell forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. The somatic cells may be immortalized to provide an unlimited supply of cells, for example, by increasing the level of telomerase reverse transcriptase (TERT). For example, the level of TERT can be increased by increasing the transcription of TERT from the endogenous gene, or by introducing a transgene through any gene delivery method or system.

Differentiated somatic cells, including cells from a fetal, newborn, juvenile or adult primate, including human, individual, are suitable somatic cells in the methods of the invention. Suitable somatic cells include, but are not limited to, bone marrow cells, epithelial cells, endothelial cells, fibroblast cells, hematopoietic cells, keratinocytes, hepatic cells, intestinal cells, mesenchymal cells, myeloid precursor cells and spleen cells. Alternatively, the somatic cells can be cells that can themselves proliferate and differentiate into other types of cells, including blood stem cells, muscle/bone stem cells, brain stem cells and liver stem cells. Suitable somatic cells are receptive, or can be made receptive using methods generally known in the scientific literature, to uptake of transcription factors including genetic material encoding the transcription factors. Uptake-enhancing methods can vary depending on the cell type and expression system. Exemplary conditions used to prepare receptive somatic cells having suitable transduction efficiency are well-known by those of ordinary skill in the art. The starting somatic cells can have a doubling time of about twenty-four hours.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein, refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of target cells, i.e. cells at exhibit at least one characteristic of a TSC, refers to a population of cells that contain fewer than about 20%, more preferably fewer than about 15%, 10%, 8%, 7%, most preferably fewer than about 5%, 4%, 3%, 2%, 1%, or less than 1%, of cells that are not target cells or their progeny as defined by the terms herein.

The skilled person will also be familiar with means to distinguish the characteristics of somatic cells from those of TSCs (in other words, to test for the loss of somatic cell phenotype). For example, as provided in the examples herein, suitable somatic cells for the production of TSCs include fibroblasts. The skilled person will be able to readily distinguish between characteristics of a fibroblast and a TSC, for example: fibroblasts are typically positive for CD44. The skilled person will be able to determine conversion from fibroblasts to TSCs by observing reduced expression of this marker.

Other markers that have altered expression during the conversion from somatic to pluripotent state include: TWIST1, TWIST2, SNAI1, SNAI2, ZEB1 and ZEB2.

The skilled person will also be able to determine when a somatic cell has commenced reprogramming towards a pluripotent state when the somatic cell loses morphological characteristics that are typical of the somatic cell. Again, the skilled person will be familiar with morphological characteristics of various somatic cells, including those of fibroblasts.

A somatic cell may also be determined to be reprogrammed to a pluripotent state, when it displays at least one characteristic of a pluripotent cell. The one or more characteristics of a pluripotent cell (e.g., an iPSC or ESC) include up-regulation of any one or more ESC markers and/or changes in cell morphology. Typically, a cell that is converted to an iPSC/EPSC-like cell will display 1, 2, 3, 4, 5, 6, 7, 8 or more characteristics of the iPSC/EPSC.

A somatic cell is determined to be converted to a TSC when it displays at least one characteristic of a TSC. For example, a fibroblast will be identified as being converted to a TSC when a fibroblast, treated according to a method of the present invention, displays at least one characteristic of TSC.

The one or more characteristics of a TSC include up-regulation of any one or more trophoblast markers and/or changes in cell morphology. Typically, a cell that is converted to a TSC will display 1, 2, 3, 4, 5, 6, 7, 8 or more characteristics of the TSC.

As used herein, a cell exhibiting at least one characteristic of a TSC made according to the present invention, may also be referred to as an "induced trophoblast stem cell" or iTSC.

In any embodiment of the present invention, a protein marker which is characteristic of a TSC nuclear CD49f (iTGA6), CD249 (aminopeptidase A), and nuclear NR2F2, TFAP2C, GATA2/3 and P63.

In further embodiments, a cell exhibiting at least one characteristic of a TSC does not express one or more of the following markers: OCT4 (POU5F1), NANOG, SOX2, SALL2, OTX2, BANCR, KLF17, DPPA3, and DNMT3L.

Further, a cell that has at least one characteristic of a TSC has the ability to differentiate into a cell exhibiting one or more characteristics of an EVT or an ST.

Additional markers which can be used to determine whether a somatic cell has been reprogrammed or converted into a TSC will be known to the skilled person. Examples of suitable markers are disclosed for example in Okae et al., (2018) Cell Stem Cell 22: 50-63, Deglincerti et al., (2016) Nature, 533: 751-4, Shahbazi et al., (2016 Nature Cell Biology 18: 700-708 and Niakan & Eggan (2013) Dev Biol 375: 54-64), the entire contents of which are herein incorporated in their entirety.

The skilled person will be familiar with methods for determining conversion of a fibroblast to a TSC by observing changes in cell morphology. For example, adult fibroblasts are characterised by having an elongated, branched cytoplasm surrounding an elliptical, speckled nucleus.

In contrast, TSCs typically form large, cobblestone-shaped colonies.

In any aspect of the invention, the TSC characteristic may be determined by analysis of cell morphology, gene expression profiles, activity assay, protein expression profile, surface marker profile, differentiation ability or a combination thereof. Examples of characteristics or markers include those that are described herein and those known to the skilled person.

Reprogramming

Various methods for reprogramming a somatic cell towards a pluripotent state are known in the art. Reprogramming of somatic cells typically involves the expression of reprogramming factors (including transcription factors), followed by culture in particular conditions for promoting the loss of markers of somatic cells (i.e., of differentiation), and gain the potential to be cell types of early embryonic origin.

Examples of suitable methods for reprogramming somatic cells are replete in the art, and are exemplified in WO 2009/101407, WO 2014/200030, WO 2015/056804, WO 2014/200114, WO 2014/065435, WO 2013/176233, WO 2012/060473, WO 2012/036299, WO 2011/158967, WO 2011/055851, WO 2011/037270, WO 2011/090221, the contents of which are hereby incorporated by reference.

Particularly preferred transcription factors, and nucleic acid sequences thereof, that may be used to reprogram a somatic cell (e.g., a fibroblast) in accordance with the methods of the invention are shown below in Table 1. It will be understood however that the present invention is not limited to the use of the transcription factors recited in Table 1 in order to reprogram a somatic cell.

The transcription factors and other protein factors referred to herein are referred to by the HUGO Gene Nomenclature Committee (HGNC) Symbol. Table 1 provides exemplary Ensemble Gene ID and Uniprot IDs for the transcription factors recited herein. The nucleotide sequences are derived from the Ensembl database (Flicek et al. (2014). Nucleic Acids Research Volume 42, Issue D1. Pp. D749-D755) version 83. Also contemplated for use in the invention is any homolog, ortholog or paralog of a transcription factor referred to herein.

The skilled person will also be familiar with the ability to reprogram somatic cells towards a naïve pluripotent state (as compared to a primed pluripotent state). It will be understood that the methods of the present invention apply to cells that have been treated so as to promote reprogramming towards a naïve or primed pluripotent state. In preferred embodiments of the invention, the method comprises increasing the protein expression of one or more factors in the somatic cell for reprogramming the somatic cell towards a naïve pluripotent state.

The skilled person will appreciate that this information may be used in performing the methods of the present invention, for example, for the purposes of providing increased amounts of transcription factors in somatic cells, or providing nucleic acids or the like for recombinantly expressing a transcription factor in a somatic cell.

TABLE 1

Accession numbers identifying exemplary nucleotide sequences and
amino acid sequences of transcription factors referred to herein.

| Transcription factor Associated Gene Name | Ensembl Gene ID | Uniprot ID |
|---|---|---|
| OCT4 (also called POU5F1) | ENSG00000204531 | Q01860 |
| SOX2 | ENSG00000181449 | P48431 |
| cMYC | ENSG00000136997 | P01106 |
| KLF4 | ENSG00000136826 | O43474 |
| LIN28 | ENSG00000131914 | Q9H9Z2 |
| NANOG | ENSG00000111704 | Q9H9S0 |

The term a "variant" in referring to a polypeptide that is at least 70%, 80%, 85%, 90%, 95%, 98%, or 99% identical to the full length polypeptide. The present invention contemplates the use of variants of the transcription factors described herein. The variant could be a fragment of full length polypeptide or a naturally occurring splice variant. The variant could be a polypeptide at least 70%, 80%, 85%, 90%, 95%, 98%, or 99% identical to a fragment of the polypeptide, wherein the fragment is at least 50%, 60%, 70%, 80%, 85%, 90%, 95%, 98%, or 99% as long as the full length wild type polypeptide or a domain thereof has a functional activity of interest such as the ability to promote conversion of a somatic cell type to a target cell type. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full length) polypeptide, by which is meant a polypeptide that has had one or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein. One of skill in the art will be aware of, or will readily be able to ascertain, whether a particular polypeptide variant, fragment, or derivative is functional using assays known in the art. For example, the ability of a variant of a transcription factor to convert a somatic cell to a target cell type can be assessed using the assays as disclosed herein in the Examples. Other convenient assays include measuring the ability to activate transcription of a reporter construct containing a transcription factor binding site operably linked to a nucleic acid sequence encoding a detectable marker such as luciferase. In certain embodiments of the invention a functional variant or fragment has at least 50%, 60%, 70%, 80%, 90%, 95% or more of the activity of the full length wild type polypeptide.

The term "increasing the amount of" with respect to increasing an amount of a transcription factor, refers to increasing the quantity of the transcription factor in a cell of interest (e.g., a somatic cell such as a fibroblast). In some embodiments, the amount of transcription factor is "increased" in a cell of interest (e.g., a cell into which an expression cassette directing expression of a polynucleotide encoding one or more transcription factors has been introduced) when the quantity of transcription factor is at least 10%, 20%, 30%, 40%, 50%, 60%, 70%, 80%, 90%, or more relative to a control (e.g., a fibroblast into which none of said expression cassettes have been introduced). However, any method of increasing an amount of a transcription factor is contemplated including any method that increases the amount, rate or efficiency of transcription, translation, stability or activity of a transcription factor (or the pre-mRNA or mRNA encoding it). In addition, down-regulation or interference of a negative regulator of transcription expression, increasing efficiency of existing translation (e.g. SINEUP) are also considered.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecules having a chemical moiety. For example, chemical moieties included unsubstituted or substituted alkyl, aromatic, or heterocyclic moieties including macrolides, leptomycins and related natural products or analogues thereof. Compounds can be known to have a desired activity and/or property, or can be selected from a library of diverse compounds.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from that of natural cells, or is otherwise flanked by a different nucleic acid sequence than that found in nature. An exogenous nucleic acid may also be extra-chromosomal, such as an episomal vector.

Screening one or more candidate agents for the ability to increase the amount of the one or more transcription factors required for reprogramming of a somatic cell type to a pluripotent state may include the steps of contacting a system that allows the product or expression of a transcription factor with the candidate agent and determining whether the amount of the transcription factor has increased. The system may be in vivo, for example a tissue or cell in an organism, or in vitro, a cell isolated from an organism or an in vitro transcription assay, or ex vivo in a cell or tissue. The amount of transcription factor may be measured directly or indirectly, and either by determining the amount of protein or RNA (e.g. mRNA or pre-mRNA). The candidate agent may function to increase the amount of a transcription factor by increasing any step in the transcription of the gene encoding the transcription factor or increase the translation of corresponding mRNA. Alternatively, the candidate agent may decrease the inhibitory activity of a repressor of transcription of the gene encoding the transcription factor or the activity of a molecule that causes the degradation of the mRNA encoding the transcription factor or the protein of the transcription factor itself.

Suitable detection means include the use of labels such as radionucleotides, enzymes, coenzymes, fluorescers, chemiluminescers, chromogens, enzyme substrates or co-factors, enzyme inhibitors, prosthetic group complexes, free radicals, particles, dyes, and the like. Such labelled reagents may be used in a variety of well-known assays, such as radioimmunoassays, enzyme immunoassays, e.g., ELISA, fluorescent immunoassays, and the like. See, for example, U.S. Pat. Nos. 3,766,162; 3,791,932; 3,817,837; and 4,233,402.

The methods of the invention include high-throughput screening applications. For example, a high-throughput screening assay may be used which comprises any of the assays according to the invention wherein aliquots of a system that allows the product or expression of a transcription factor are exposed to a plurality of candidate agents within different wells of a multi-well plate. Further, a high-throughput screening assay according to the disclosure involves aliquots of a system that allows the product or expression of a transcription factor which are exposed to a plurality of candidate agents in a miniaturized assay system of any kind.

The method of the disclosure may be "miniaturized" in an assay system through any acceptable method of miniaturization, including but not limited to multi-well plates, such as 24, 48, 96 or 384-wells per plate, microchips or slides. The assay may be reduced in size to be conducted on a micro-chip support, advantageously involving smaller amounts of reagent and other materials. Any miniaturization of the process which is conducive to high-throughput screening is within the scope of the invention.

In any method of the invention the cells having at least one characteristic of an TSC can be transferred into the same mammal from which the somatic cells were obtained. In other words, the somatic cells used in a method of the invention can be an autologous cell, i.e., can be obtained from the same individual in which the target cells are to be administered. Alternatively, the target cell can be allogenically transferred into another individual. Preferably, the cell is autologous to the subject in a method of treating or preventing a medical condition in the individual.

Culture Media

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. Exemplary cell culture medium for use in methods of the invention are shown in Table 2.

TABLE 2

| Cell culture media that can be used to culture different cell types | | | |
| --- | --- | --- | --- |
| Cell | Media | Cat#: | Company/Reference |
| Fibroblasts | Medium 106 DMEM (high glucose, without sodium pyruvate), 10% FBS, 1% penicillin/streptomycin, 1% nonessential amino acids, 1 mM Glutamax, 0.1 mM 2-mercaptoethanol and 1 mM sodium pyruvate | N/A | Life Technologies ThermoFisher Life Technologies |
| Naïve media (for culturing naïve ESCs or iPSCs) | T2iLGoY | N/A | Guo et al., (2016) Stem Cell Reports, 6(4): P437-446 |
| | 5iLAF | N/A | Theunissen et al., (2014) Cell Stem Cell, 15: 471-487 |
| | RSeT | #05978 | StemCell Technologies |
| | PXGL | N/A | Bredenkamp et al., (2019) Stem Cell Reports, https://doi.org/10.1016/j.stemcr.2019.10.009 |
| | NHSM | N/A | Gafi et al., (2013) Nature, 504(7479): 282-6 |
| LCDM medium (extended medium for culturing EPSCs or iPSCs) | LCDM medium | N/A | Yang et al., (2017) Cell, 169(2): 243-257 |
| Primed iPSCs | KSR/FGF2 | N/A | Eiselleovat et al., (2009) Stem Cells, 27: 1847-57 |
| | Essential 8 | # A1517001 | ThermoFisher |
| | mTeSR | # 05825 | StemCell Technologies |
| | AKIT | | Yasuda et al., (2018) Nature Biomedical Engineering, 2: 173-182 |
| | B8 | | Kuo et al., (2020) Stem Cell Reports, 14, 2 256-270. |

TABLE 2-continued

Cell culture media that can be used to culture different cell types

| Cell | Media | Cat#: | Company/Reference |
|------|-------|-------|-------------------|
| | TeSR-E7 | | StemCell Technologies |
| | Essential 6 | #A1516401 | ThermoFisher |
| | Essential 8 | # A1517001 | ThermoFisher |

A key finding of the present invention is that once the reprogramming process has commenced, a somatic cell undergoing reprogramming (but without having completed reprogramming) may be transitioned into media for supporting TSC growth and proliferation. Upon contacting the cell with such media, the inventors have found that it is possible to generate stable TSC-like cells (which may interchangeably be referred to as induced trophoblast stem cells or iTSCs).

Thus, by exposing cells to TSC media during the reprogramming process, the inventors have developed a novel method for generating human TSCs directly from somatic cells.

It will be understood that in accordance with the methods of the invention, once the reprogramming process has commenced, the somatic cells may be contacted with the TSC media at any time. For example, the contacting may be at 0.5, 1, 2, 3, 4, 5, 6, 7, 8, 10 or more including 14, 21, 28, 35 or more days following commencement of the reprogramming towards a pluripotent fate.

The initial media utilised during early stages of reprogramming also does not need to be pluripotency media. For example, in preferred methods of the invention, the cells are exposed to reprogramming agents in fibroblast media (or other media for supporting growth of somatic cells) prior to being transitioned into TSC media at a later stage, but prior to completion of reprogramming.

Alternatively, once reprogramming has commenced, the somatic cells may be cultured in naïve or primed media, or extended media, as herein described, for a period of time so as (which may or may not include completion of the reprogramming process and to generate induced pluripotent stems cells (iPSCs)). After this time, the cells may be transitioned to the TSC media.

The culture medium that is suitable for supporting TSC and proliferation thereof is preferably a culture medium as described in Okae (2018) Cell Stem Cell, and WO 2016/143866, the contents of which are hereby incorporated by reference.

The base media composition of the TSC may be any base medium typically used, including DMEM, MEM, RPMI 1640 and the like. Serum, growth factors, pyruvate, amino acids, antibiotics and the like can be appropriately included in the medium.

The TSC culture preferably comprises at least one growth factor and at least one ROCK inhibitor.

As used herein, a growth factor may be any growth factor, but is preferable one selected from Epidermal Growth Factor (EGF), insulin, transforming growth factor (TGF). The amount of growth factor may be any amount, for example 0.1 to 1000 ng/ml, preferably 10-100 ng/ml.

As used herein, a ROCK inhibitor refers to an inhibitor of Rho-binding kinase. Examples of such inhibitors include ((1R,4r)-4-((R)-1-aminoethyl)-N-(pyridin-4-yl)cyclohexane carboxamide, Abcam), also known as trans-N-(4-(1-amino-ethyl)-cyclohexanecarboxamide, 1-(5-isoquinolunyl) (sulfonyl) homopiperazine (1-(5-isoquinolinylsulfonyl)homopiperazine. Typically the amount of ROCK inhibitor will be between about 0.1 to 50 μM, preferably about 1 to 10 μM.

In certain preferred embodiments, the TSC culture is the ASECRiAV medium described in Okae et al., and comprises: A83-01, SB431542, EGF, CHIR, a ROCK inhibitor, ascorbic acid and valproic acid.

Most preferable the TSC media comprises:
DMEM/F-12,
GlutaMAX™ (ThermoFisher) supplemented with 0.3% BSA (Sigma),
0.2% FBS (ThermoFisher),
1% ITS-X supplement (ThermoFisher),
0.1 mM 2-mercaptoethanol (ThermoFisher),
0.5% Pen-Strep (ThermoFisher),
1.5 μg/ml L-ascorbic acid (Sigma),
5 μM Y27632 ((1R,4r)-4-((R)-1-aminoethyl)-N-(pyridin-4-yl)cyclohexane carboxamide, Abcam),
2 μM CHIR99021 (6-((2-((4-(2,4-Dichlorophenyl)-5-(4-methyl-1H-imidazol-2-Apyrimidin-2-yl)amino)ethyl) amino) nicotinonitrile Miltenyi Biotec),
0.5 μM A83-01 (3-(6-Methyl-2-pyridinyl)-N-phenyl-4-(4-quinolinyl)-1H-pyrazole-1-carbothioamide, Sigma),
1 μM SB431542 (4-[4-(1,3-benzodioxol-5-yl)-5-(2-pyridinyl)-1H-imidazol-2-yl]benzamide)
50 ng/ml EGF (Peprotech) and
0.8 mM Valproic acid (VPA, Sigma).

Differentiation

The present invention also includes a method of generating differentiated cells, the method comprising subjecting a cell exhibiting at least one characteristic of a TSC, made according to the present invention, to differentiation conditions. According to specific embodiments, the TSC cells made according to the present invention, can be used to isolate lineage-specific cells, for example ST and EVTs.

The skilled person will be familiar with standard methods for differentiating the TSCs generated according to the present invention. Briefly, TSCs can be differentiated to syncytiotrophoblasts (STs) by subjecting the TSCs to MEF-BAP treatment (MEF conditioned media, BMP4, TGFβi, FGFRi, as described in Amita et al., 2013 PNAS, 110: E1212-1221). Alternatively, exposure of TSCs to forskolin treatment can also be used to differentiate TSCs towards ST fate.

Further methods for differentiation are disclosed in Kidder (2014) Methods Mol Biol, 1150-201-12; Lei et al., (2017) Placenta, 28: 14-12; and Chen et al., (2013) Biochemical and Biophysical Research Communications, 431; 179-202. The methods may include culturing cells in a medium devoid of GFG4 and heparin. The methods may also involve genetic modification of the cells in media comprising differentiation factors.

Successful differentiation to STs can be determined by measuring basal β-hCG (human chorionic gonadotropin) secretion as well as expression of human placental lactogen genes. Alternatively, successful differentiation to STs can be determined by the presence of SDC1+ multinucleated cells.

Successful differentiation to EVT fate can be confirmed by determining protein expression of one or more markers selected from: HLA-G, PRG2 and PAPP2.

Nucleic Acids and Vectors

A nucleic acid or vector comprising a nucleic acid as described herein may include one or more of the sequences referred to above in Table 1.

The term "expression" refers to the cellular processes involved in producing RNA and proteins and as appropriate, secreting proteins, including where applicable, but not limited to, for example, transcription, translation, folding, modification and processing.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "vector" refers to a carrier DNA molecule into which a DNA sequence can be inserted for introduction into a host or somatic cell. Preferred vectors are those capable of autonomous replication and/or expression of nucleic acids to which they are linked. Vectors capable of directing the expression of genes to which they are operatively linked are referred to herein as "expression vectors". Thus, an "expression vector" is a specialized vector that contains the necessary regulatory regions needed for expression of a gene of interest in a host cell. In some embodiments the gene of interest is operably linked to another sequence in the vector. Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operatively linked" includes having an appropriate start signal (e.g. ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors.

As used herein, the term "adenovirus" refers to a virus of the family Adenovirida. Adenoviruses are medium-sized (90-100 nm), nonenveloped (naked) icosahedral viruses composed of a nucleocapsid and a double-stranded linear DNA genome.

As used herein, the term "non-integrating viral vector" refers to a viral vector that does not integrate into the host genome; the expression of the gene delivered by the viral vector is temporary. Since there is little to no integration into the host genome, non-integrating viral vectors have the advantage of not producing DNA mutations by inserting at a random point in the genome. For example, a non-integrating viral vector remains extra-chromosomal and does not insert its genes into the host genome, potentially disrupting the expression of endogenous genes. Non-integrating viral vectors can include, but are not limited to, the following: adenovirus, alphavirus, picornavirus, and vaccinia virus. These viral vectors are "non-integrating" viral vectors as the term is used herein, despite the possibility that any of them may, in some rare circumstances, integrate viral nucleic acid into a host cell's genome. What is critical is that the viral vectors used in the methods described herein do not, as a rule or as a primary part of their life cycle under the conditions employed, integrate their nucleic acid into a host cell's genome.

The vectors described herein can be constructed and engineered using methods generally known in the scientific literature to increase their safety for use in therapy, to include selection and enrichment markers, if desired, and to optimize expression of nucleotide sequences contained thereon. The vectors should include structural components that permit the vector to self-replicate in the somatic cell type. For example, the known Epstein Barr oriP/Nuclear Antigen-1 (EBNA-I) combination (see, e.g., Lindner, S. E. and B. Sugden, The plasmid replicon of Epstein-Barr virus: mechanistic insights into efficient, licensed, extrachromosomal replication in human cells, Plasmid 58:1 (2007), incorporated by reference as if set forth herein in its entirety) is sufficient to support vector self-replication and other combinations known to function in mammalian, particularly primate, cells can also be employed. Standard techniques for the construction of expression vectors suitable for use in the present invention are well-known to one of ordinary skill in the art and can be found in publications such as Sambrook J, et al., "Molecular cloning: a laboratory manual," (3rd ed. Cold Spring harbor Press, Cold Spring Harbor, N.Y. 2001), incorporated herein by reference as if set forth in its entirety.

In the methods of the invention, genetic material encoding the relevant transcription factors required for a conversion is delivered into the somatic cells via one or more reprogramming vectors. Each transcription factor can be introduced into the somatic cells as a polynucleotide transgene that encodes the transcription factor operably linked to a heterologous promoter that can drive expression of the polynucleotide in the somatic cell.

Suitable reprogramming vectors are any described herein, including episomal vectors, such as plasmids, that do not encode all or part of a viral genome sufficient to give rise to an infectious or replication-competent virus, although the vectors can contain structural elements obtained from one or more virus. One or a plurality of reprogramming vectors can be introduced into a single somatic cell. One or more transgenes can be provided on a single reprogramming vector. One strong, constitutive transcriptional promoter can provide transcriptional control for a plurality of transgenes, which can be provided as an expression cassette. Separate expression cassettes on a vector can be under the transcriptional control of separate strong, constitutive promoters, which can be copies of the same promoter or can be distinct promoters. Various heterologous promoters are known in the art and can be used depending on factors such as the desired expression level of the transcription factor. It can be advantageous, as exemplified below, to control transcription of separate expression cassettes using distinct promoters having distinct strengths in the v cells. Another consideration in selection of the transcriptional promoters is the rate at which the promoter(s) is silenced. The skilled artisan will appreciate that it can be advantageous to reduce expression of one or more transgenes or transgene expression cassettes after the product of the gene(s) has completed or substantially completed its role in the reprogramming method. Exemplary promoters are the human EF1a elongation factor promoter, CMV cytomegalovirus immediate early promoter and CAG chicken albumin promoter, and corresponding homologous promoters from other species. In human somatic cells, both EF1a and CMV are strong promoters, but the CMV promoter is silenced more efficiently than the EF1a promoter such that expression of transgenes under control of the former is turned off sooner than that of transgenes under control of the latter. The transcription factors can be expressed in the somatic cells in a relative ratio that can be varied to modulate reprogramming efficiency. Preferably, where a plurality of transgenes is encoded on a single transcript, an internal ribosome entry site is provided upstream of transgene(s) distal from the transcriptional promoter. Although the relative ratio of factors can vary depending upon the factors delivered, one of ordinary skill in possession of this disclosure can determine an optimal ratio of factors.

The skilled artisan will appreciate that the advantageous efficiency of introducing all factors via a single vector rather than via a plurality of vectors, but that as total vector size increases, it becomes increasingly difficult to introduce the vector. The skilled artisan will also appreciate that the position of a transcription factor within a polycistronic cassette on a vector can affect its temporal expression, and the resulting reprogramming efficiency. As such, various combinations of factors on combinations of vectors may be utilised. Several such combinations are here shown to support reprogramming.

After introduction of the reprogramming vector(s) and while the somatic cells are being reprogrammed, the vectors can persist in target cells while the introduced transgenes are transcribed and translated. Transgene expression can be advantageously downregulated or turned off in cells that have been reprogrammed to a target cell type. The reprogramming vector(s) can remain extra-chromosomal. At extremely low efficiency, the vector(s) can integrate into the cells' genome. The examples that follow are intended to illustrate but in no way limit the present invention.

Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art (e.g., Stadtfeld and Hochedlinger, Nature Methods 6(5):329-330 (2009); Yusa et al., Nat. Methods 6:363-369 (2009); Woltjen, et al., Nature 458, 766-770 (9 Apr. 2009)). Such methods include, but are not limited to, direct delivery of DNA such as by ex vivo transfection (Wilson et al., Science, 244:1344-1346, 1989, Nabel and Baltimore, Nature 326: 711-713, 1987), optionally with a lipid-based transfection reagent such as Fugene6 (Roche) or Lipofectamine (Invitrogen), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, J. Cell Biol., 101:1094-1099, 1985; U.S. Pat. No. 5,789,215, incorporated herein by reference); by electroporation (U.S. Pat. No. 5,384,253, incorporated herein by reference; Tur-Kaspa et al., Mol. Cell Biol., 6:716-718, 1986; Potter et al., Proc. Nat'l Acad. Sci. USA, 81:7161-7165, 1984); by calcium phosphate precipitation (Graham and Van Der Eb, Virology, 52:456-467, 1973; Chen and Okayama, Mol. Cell Biol., 7(8):2745-2752, 1987; Rippe et al., Mol. Cell Biol., 10:689-695, 1990); by using DEAE-dextran followed by polyethylene glycol (Gopal, Mol. Cell Biol., 5:1188-1190, 1985); by direct sonic loading (Fechheimer et al., Proc. Nat'l Acad. Sci. USA, 84:8463-8467, 1987); by liposome mediated transfection (Nicolau and Sene, Biochim. Biophys. Acta, 721:185-190, 1982; Fraley et al., Proc. Nat'l Acad. Sci. USA, 76:3348-3352, 1979; Nicolau et al., Methods Enzymol., 149:157-176, 1987; Wong et al., Gene, 10:87-94, 1980; Kaneda et al., Science, 243:375-378, 1989; Kato et al., J Biol. Chem., 266:3361-3364, 1991) and receptor-mediated transfection (Wu and Wu, Biochemistry, 27:887-892, 1988; Wu and Wu, J. Biol. Chem., 262:4429-4432, 1987); and any combination of such methods, each of which is incorporated herein by reference.

A number of polypeptides capable of mediating introduction of associated molecules into a cell have been described previously and can be adapted to the present invention. See, e.g., Langel (2002) Cell Penetrating Peptides: Processes and Applications, CRC Press, Pharmacology and Toxicology Series. Examples of polypeptide sequences that enhance transport across membranes include, but are not limited to, the *Drosophila* homeoprotein antennapedia transcription protein (AntHD) (Joliot et al., New Biol. 3: 1121-34, 1991; Joliot et al., Proc. Natl. Acad. Sci. USA, 88: 1864-8, 1991; Le Roux et al., Proc. Natl. Acad. Sci. USA, 90: 9120-4, 1993), the herpes simplex virus structural protein VP22 (Elliott and O'Hare, Cell 88: 223-33, 1997); the HIV-1 transcriptional activator TAT protein (Green and Loewenstein, Cell 55: 1179-1188, 1988; Frankel and Pabo, Cell 55: 1 289-1193, 1988); Kaposi FGF signal sequence (kFGF); protein transduction domain-4 (PTD4); Penetratin, M918, Transportan-10; a nuclear localization sequence, a PEP-I peptide; an amphipathic peptide (e.g., an MPG peptide); delivery enhancing transporters such as described in U.S. Pat. No. 6,730,293 (including but not limited to an peptide sequence comprising at least 5-25 or more contiguous arginines or 5-25 or more arginines in a contiguous set of 30, 40, or 50 amino acids; including but not limited to an peptide having sufficient, e.g., at least 5, guanidino or amidino moieties); and commercially available Penetratin™ 1 peptide, and the Diatos Peptide Vectors ("DPVs") of the Vectocell® platform available from Daitos S.A. of Paris, France. See also, WO/2005/084158 and WO/2007/123667 and additional transporters described therein. Not only can these proteins pass through the plasma membrane but the attachment of other proteins, such as the transcription factors described herein, is sufficient to stimulate the cellular uptake of these complexes.

Pharmaceutical Compositions and Other Applications

The invention, according to certain embodiments, contemplates the use of any cells, tissues and/or organs/organoids generated using the cells having at least one characteristic of a TSC (i.e., the iTSCs) made according to the invention. The invention further contemplates the use of any particle or compound secreted either by the TSCs made according to the invention, or secreted by EVTs or STs differentiated from the TSCs made according to the invention.

The isolated cells of the present invention may be further used for disease modelling, drug screening and patient-specific cell based therapy.

Thus, according to a certain aspect of the invention, there is provided an isolated placenta-like organoid, or a blastocyst-like cell comprising a TSC made according to the methods of the invention.

According to a further aspect, there is provided a method of augmenting a placenta, or a blastocyst comprising introducing into the placenta or blastocyst, a cell, or population of cells made according to the present invention. The cell or population of cells may be a cell exhibiting at least one characteristic of a TSC, made according to the method of the invention. Alternatively the cell or population of cells, may be a differentiated cell, or population of differentiated cells, made from a cell exhibiting at least one characteristic of a TSC of the invention.

Introducing cells may be performed in vitro or ex vivo via direct injection or aggregation within the developing host placenta or embryo.

Cells having at least one characteristic of a TSC, as made according to the invention, may also be used to prepare model systems for disorders associated with development and/or activity of trophoblasts. The systems find utility in screening for genes expressed in or essential for trophoblast differentiation and/or activity, to screen for agents and conditions (such as culture conditions and manipulation) that effect trophoblast development and/or activity, to produce specific growth factors and hormones, or as a cell therapy for disorders associated with development and/or activity of trophoblasts.

Thus, according to an aspect of the present invention, there is provided a method of identifying an agent capable of modulating trophoblast development and/or activity, the method comprising:

(i) contacting a TSC made according to the present invention, or an organoid derived from said TSC (such as a blastocyst-like organoid, or placenta-like organoid) with a candidate agent; and (ii) comparing development and/or activity of the TSC or the organoid following said contacting with said agent to development and/or activity of said TSC or said organoid without said agent, wherein an effect of said agent on said development and/or activity of said TSC or said organoid above a predetermined level relative to said development and/or or activity of said TSC or said organoid without said agent is indicative that said drug modulates trophoblast development and/or activity.

As used herein, the term "modulating" refers to altering trophoblast development and/or activity either by inhibiting or by promoting.

According to specific embodiments, modulating is inhibiting development and/or activity.

According to specific embodiments, modulating is promoting development and/or activity.

For the same culture conditions the effect of the candidate agent on trophoblast development and/or activity is generally expressed in comparison to the development and/or activity in a cell of the same species but not contacted with the candidate agent or contacted with a vehicle control, also referred to as control.

As used herein the phrase "an effect above a predetermined level" refers to a change in trophoblast development and/or activity or organoid development following contacting with the agent which is higher than a predetermined level such as a about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the level of expression prior to contacting with the candidate agent.

According to specific embodiments, the candidate agent may be any compound including, but not limited to a chemical, a small molecule, a polypeptide and a polynucleotide.

According to specific embodiments the selected agents may be further used to treat various conditions requiring regulation of trophoblast development or activity such as the conditions described below.

Recurrent miscarriage and fetal growth restriction (FGR) are associated with placental dysfunction and contribute to handicaps and in severe cases death. Cellular transplantation of intact and healthy TSCs holds great promise in the clinic as the transplanted cells might be able to rescue some of these fetuses by supporting the undeveloped/damaged placenta.

According to another aspect of the present invention, there is provided a method of treating and/or preventing a disorder associated with development and/or activity of trophoblasts in a subject in need thereof, the method comprising administering to the subject a therapeutically effective amount of an TSC made according to the present invention, thereby treating and/or preventing the disorder associated with development and/or activity of trophoblasts in the subject.

The terms "treating" or "treatment" refers to inhibiting, preventing or arresting the development of a pathology (e.g. recurrent miscarriage) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein the phrase "subject in need thereof" refers to a mammalian subject (e.g., human being) who is diagnosed with the pathology. In a specific embodiment, this term encompasses individuals who are at risk to develop the pathology. Veterinary uses are also contemplated. The subject may be of any gender or at any age including neonatal, infant, juvenile, adolescent, adult and elderly adult. According to specific embodiments, the subject is a female.

This aspect of the present invention contemplated treating a disorder associated with development and/or activity of trophoblasts. According to specific embodiments, the disease is selected from the group consisting of recurrent miscarriage, Preeclampsia, Fetal Growth Restriction (FGR), hydatiform mole and choriocarcinoma.

As trophoblasts produce several secreted growth factors and hormones, and particles, such as exosomes according to another aspect of the present invention, there is provided a method of obtaining a compound or particle produced by a trophoblast, the method comprising culturing a TSC or the TCS cell culture of the present invention and isolating from the culture medium a compound or particle secreted by the cells, thereby obtaining the compound or particle produced by the trophoblast.

According to specific embodiments, the compound is a growth factor or a hormone, such as but not limited to human Chorionic Gonadotropin (hCG). The particle may be an exosome.

The cells of the present invention, may be transplanted to a subject per se, or in a pharmaceutical composition where they are mixed with suitable carriers or excipients. Similarly, the constructs of the present invention may be administered to a subject per se, or in a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the cells or organoids of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Typically, the pharmaceutical composition is administered in a local rather than systemic manner, for example, via injection of the pharmaceutical composition directly into a tissue region of a patient.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Pharmaceutical compositions suitable for use in context of the present invention include compositions wherein the active ingredients are contained in an amount effective to achieve the intended purpose. Determination of a therapeutically effective amount is well within the capability of those skilled in the art, especially in light of the detailed disclosure provided herein.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser advice may be a syringe. The syringe may be prepacked with the cells. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The present invention includes the following non-limiting Examples.

EXAMPLES

Example 1: Human iTSCs Generated from Somatic Cell Reprogramming

Primary adult human dermal fibroblasts (HDFa) were obtained from Life Technologies. HDFa were expanded in medium 106 (Life Technologies) supplemented with LSGS (Gibco) for nuclear reprogramming experiments. The early passage (<P6) fibroblast cells were then seeded into 6-well plates at 50,000-70,000 cells per well before transduction in fibroblast medium containing DMEM (Gibco), 10% FBS (Hyclone), 1% nonessential amino acids (Gibco), 1 mM GlutaMAX (Gibco), 1% Pen-strep (Gibco), 0.1 mM 2-mercaptoethanol (Gibco) and 1 mM sodium pyruvate (Gibco).

48 hours later, cells in one well were trypsinized for counting to determine the volume of viruses required for transduction (MOI). Transduction was performed using CytoTune 2.0 iPSC Sendai Reprogramming Kit (Invitrogen)

consisting of four transcription factors, OCT4, SOX2, cMYC, KLF4 (OKSM). 24 hours later, the viruses were removed and the media changed every other day.

7 days post-transduction, cells were harvested using TrypLE Express (Life tech) and re-seeded onto a layer of irradiated MEF feeders in fibroblast media. The following day, the media was changed to: 1) iTSC media, 2) naïve media, 3) primed media or 4) LCDM media, as further described below.

Cells transferred to iTSC media 7-days post-transduction are herein referred to as "iTSCd8" reprogramming intermediates or "D8 fibroblast intermediates".

For cells cultured in media 2-4 (i.e., naïve, primed or LCDM media), cells were cultured for 5-13 days in this media prior to transfer into TSC media. Cells cultured in naïve media from days 8 to 21 may be termed "partially reprogramming intermediates", "naïve reprogramming intermediates" or D21 naïve intermediates. Cells cultured in Essential 7 (E7) media from days 8 to 21 may also be termed "partially reprogrammed intermediates" (or "primed reprogramming intermediates" or D21 primed intermediates).

Upon culturing in TSC media, once the iTSCs become confluent and evident, iTSCs were passaged every 3-4 days at a 1:2-1:4 ratio. For the initial 4 passages, iTSCs were passaged onto iMEF feeders using TrpLE Express (Life tech) and cultured in a 37° C., 5% $O_2$ and 5% $CO_2$ incubator. Starting from passage 5, iTSCs were passaged onto tissue culture flask that was pre-coated with 5 µg/ml Col IV (Sigma) (for at least one hour at 37° C.) and cultured in a 37° C., 20% $O_2$ and 5% $CO_2$ incubator.

In still a further example, cells were retained in fibroblast media up to 21 days prior to transitioning to TSC media. These cells are also referred to herein as iTSCd28 cells (see FIG. 6).

Generally, it will be appreciated that regardless of the media used, it is possible to obtain iTSCs from partially reprogrammed intermediates utilising the methods of the invention.

Media Used in this Example:

1. iTSC media was as described in Okae et al., Cell Stem Cell, 2018 and comprised:
   DMEM/F-12,
   GlutaMAX™ (ThermoFisher) supplemented with 0.3% BSA (Sigma),
   0.2% FBS (ThermoFisher),
   1% ITS-X supplement (ThermoFisher),
   0.1 mM 2-mercaptoethanol (ThermoFisher),
   0.5% Pen-Strep (ThermoFisher),
   1.5 µg/ml L-ascorbic acid (Sigma),
   5 µM Y27632 ((1R,4r)-4-((R)-1-aminoethyl)-N-(pyridin-4-yl)cyclohexane carboxamide, Abcam),
   2 µM CHIR99021 (6-((2-((4-(2,4-Dichlorophenyl)-5-(4-methyl-1H-imidazol-2-yl)pyrimidin-2-yl)amino)ethyl)amino) nicotinonitrile Miltenyi Biotec),
   0.5 µM A83-01 (3-(6-Methyl-2-pyridinyl)-N-phenyl-4-(4-quinolinyl)-1H-pyrazole-1-carbothioamide, Sigma),
   1 µM SB431542 (4-[4-(1,3-benzodioxol-5-yl)-5-(2-pyridinyl)-1H-imidazol-2-yl]benzamide)
   50 ng/ml EGF (Peprotech) and
   0.8 mM Valproic acid (VPA, Sigma).

2. Naive media.
Naive t2iLGoY medium as reported in Guo et al., (2016) Stem Cell Reports, 6(4): P437-446) comprising:
   a 50:50 mixture of DMEM/F-12 (Gibco) and Neurobasal medium (Gibco), supplemented with 2 mM L-glutamine (Gibco),
   0.1 mM 2-mercaptoethanol (Gibco), 0.5% N2 supplement (Gibco),
   1% B27 supplement (Gibco),
   1% Pen-strep (Gibco),
   10 ng/ml human LIF (made in house),
   250 µM L-ascorbic acid (Sigma),
   10 µg/ml recombinant human insulin (Sigma),
   1 µM PD0325901 (Miltenyi Biotec),
   1 µM CHIR99021 (Miltenyi Biotec),
   2.5 µM Gö6983 (Tocris),
   10 µM Y-27632 (Abcam).
   Other examples of naïve media include: 5iLAF, RSeT and PXGL.

3. Primed media.
An exemplary primed medium comprises:
   DMEM/F12 (ThermoFisher),
   20% Knockout Serum Replacement (KSR, ThermoFisher),
   1 mM GlutaMAX (ThermoFisher),
   55 µM 2-mercaptoethanol (ThermoFisher),
   1% Non-essential amino acids (ThermoFisher),
   50 ng/mL recombinant human FGF2 (Miltenyi Biotec),
   1% Pen-strep (ThermoFisher).
   The media KSR/FGF2, E8, mTeSR, AKIT, B8 are further examples of primed media.

4. LCDM medium:
   50:50 mixture of DMEM/F-12 (ThermoFisher) and Neurobasal medium (ThermoFisher), supplemented with 0.5% N2 supplement (ThermoFisher),
   1% B27 supplement (ThermoFisher),
   1% Nonessential amino acids (ThermoFisher),
   1 mM GlutaMAX (ThermoFisher),
   1% Pen-strep (ThermoFisher),
   0.1 mM 2-mercaptoethanol (ThermoFisher),
   0.5% KSR (ThermoFisher),
   10 ng/ml human LIF (made in house),
   1 µM CHIR99021 (Miltenyi Biotec),
   2 µM (S)-(+)-Dimethindene maleate (Tocris),
   2 µM Minocycline hydrochloride (Tocris),
   1 µM IWR-endo-1 (Selleckchem) and
   2 µM Y-27632 (Abcam).

Example 2: Conversion of Established Human Pluripotent Stem Cells to TSCs

Established naive EPSCs/iPSCs were cultured in t2iLGoY conditions as described above. Naive hEPSCs/hiPSCs were seeded onto a layer of MEF feeders or Collagen IV coated plates. When the TSCs became confluent and evident, TSCs were passaged every 3-4 days at a 1:2-1:4 ratio. TSCs were passaged onto iMEF feeders or on Col IV (Sigma) using TrpLE Express (Life tech) and cultured in a 37° C., 20% $O_2$ and 5% $CO_2$ incubator.

Primed human EPSCs/iPSCs are preferably contacted with naïve media prior to contact with TSC media.

Established human LCDM EPSCs or iPSCs (which can also be referred to as "extended" EPSCs or iPSCs) were cultured in LCDM medium as described above. Cells were seeded onto a layer of MEF feeders or Collagen IV coated plates. When the TSCs become confluent and evident, TSCs were passaged every 3-4 days at a 1:2-1:4 ratio. TSCs were passaged onto iMEF feeders or on Col IV (Sigma) using TrpLE Express (Life tech) and cultured in a 37° C., 20% $O_2$ and 5% $CO_2$ incubator.

Primed human EPSCs/iPSCs are preferably contacted with LCDM media prior to contact with TSC media.

US 12,668,775 B2

35
36

Example 3: Direct Conversion of Somatic Cells to iTSCs

Figure 3:
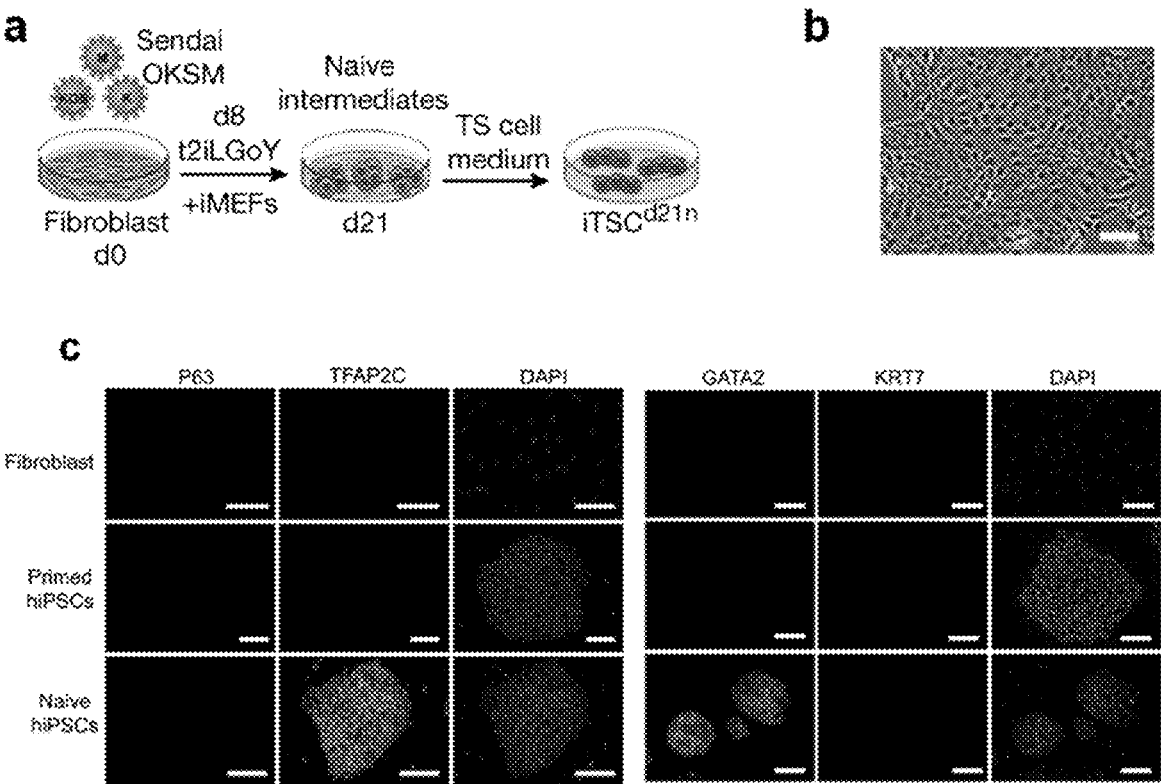
FIG. 3: Stabilization of the TE signatures during naive reprogramming for derivation of human iTSCs. (a) Schematic representation of the experimental design to capture and stabilize the naive intermediates in the TSC medium. (b) Phase-contrast images of iTSCs generated. (c) Immunostaining of fibroblast, primed, naive t2iLGoY iPS cells with P63, TFAP2C, GATA2 and KRT7, n=2. Scale bar, 100 μm. (d) Immunostaining of iTSCd21n with P63, TFAP2C, GATA2 and KRT7. Scale bar, 100 μm. Representative images from n=4. (e) Gene expression of trophoblast genes in fibroblasts, primed, naive t2iLGoY iPS cells, iTSCd21n and TS cells (TSCs) derived from a human blastocyst (TSCblast) and first-trimester placental trophoblast (TSCCT), mean of replicates, n=2. (f) Phase-contrast image of ST and EVT cells differentiated from iTSCd21n, n=4. Scale bar, 100 μm. (g) SDC1 and HLA-G immunostaining of syncytiotrophoblast (ST) (left) and extravillous trophoblast (EVT) (right) cells, respectively, differentiated from iTSCd21n. Scale bar, 100 μm. Representative images from n=4. (h) Fusion index of iTSCd21n ST and iTSCd21n, n=5, data are represented as mean±s.e.m. P values by two-tailed unpaired Student's t-test. (i) Representative results for over-the-counter hCG pregnancy test for medium of ST cells differentiated from iTSCd21n and control medium, n=6. (j) hCG levels in iTSCd21n- and iTSCd21n-ST conditioned medium, detected by ELISA, n=4. (k) Representation of iTSCd21n engraftment assay by injection into NOD-SCID mice. The urine, blood serum and lesions were examined 9 days post-injection (d.p.i). Representative positive results for hCG pregnancy test from urine samples collected from iTSCd21n-injected mice compared to the vehicle controls. n=3. (l) hCG level in mouse blood serum detected by ELISA, n=4. (m) Lesions collected from subcutaneously engrafted iTSCd21n in NOD-SCID mice, n=4. (n) H&E staining, Immunohistochemical staining of KRT7, SDC1 and HLA-G in the lesions collected from iTSCd21n engrafts in NOD-SCID mice. No lesions were evident in vehicle controls. Arrows indicate HLA-G-positive trophoblast cells. Scale bar, 200 μm. Representative images from n=4.
Figure 3:
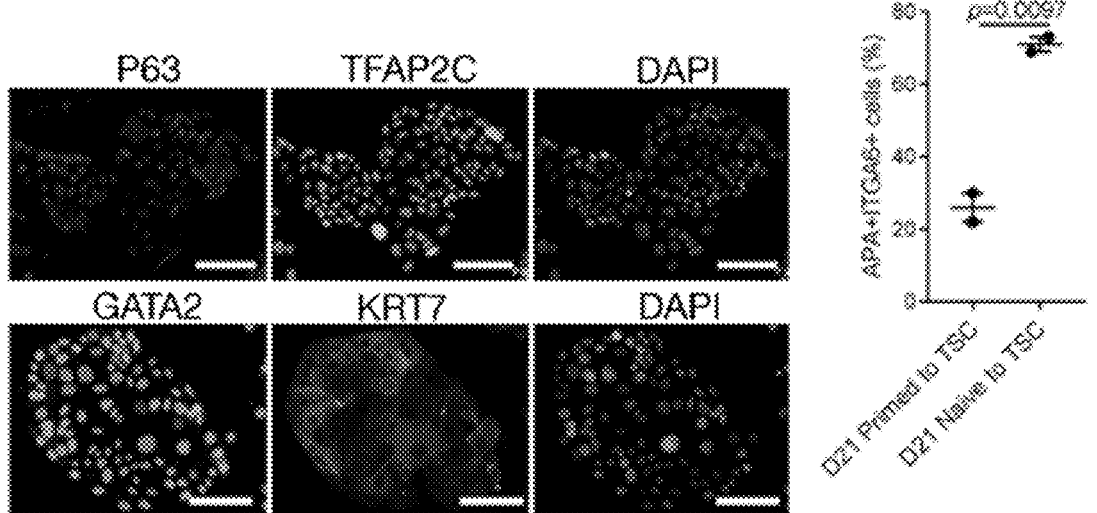
Figure 3:
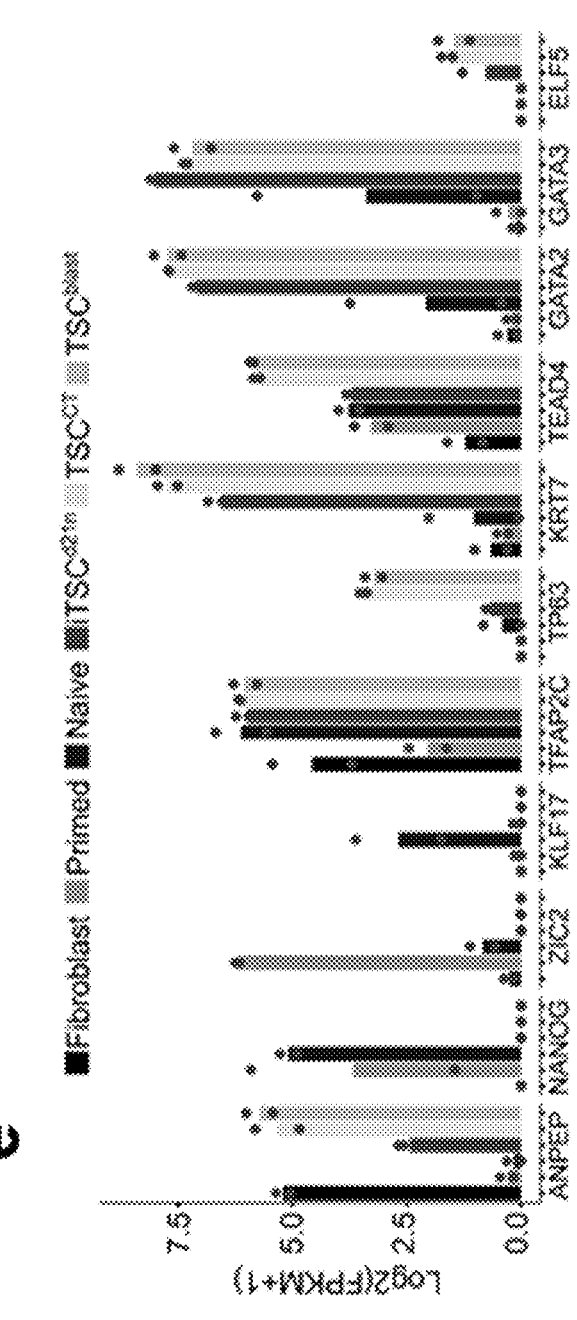
Figure 3:
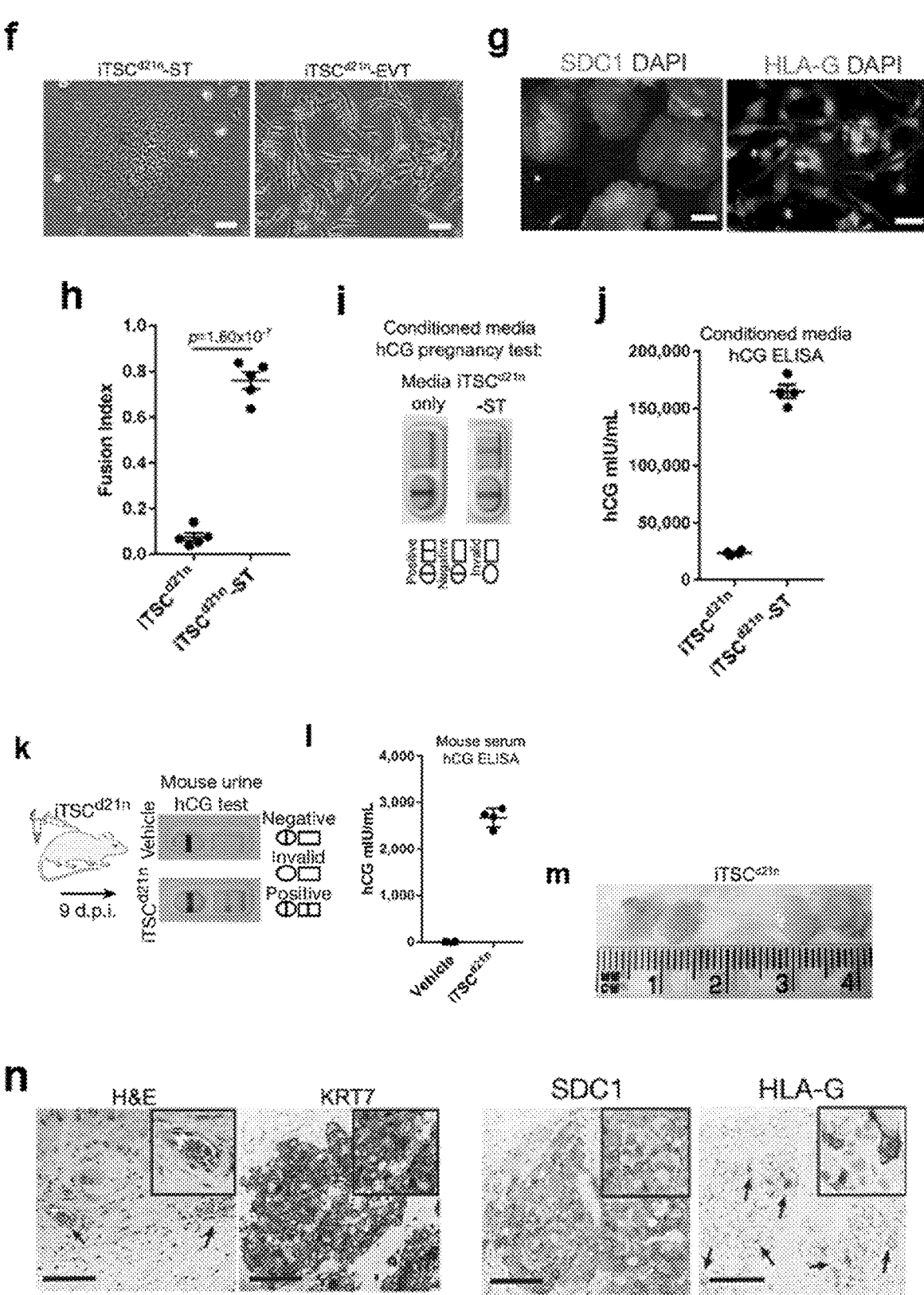

FIG. 3 shows the results from characterisation of TSCs generated by the stabilisation of TE signatures during naïve reprogramming for derivation of human iTSCs.

FIG. 3a provides a schematic representation of the experimental design to capture and stabilise naïve intermediates in TSC medium.

Briefly, the results show that during reprogramming from fibroblasts towards a de-differentiated state, it is possible to capture and stabilise intermediates in TSC medium, allowing for the generating of iTSCs.

Phase-contrast images of cells generated via this process indicate that the cells have similar morphology to TSCs (cobblestone appearance, FIG. 3b).

Immunostaining of fibroblast, primed, naïve t2iLGoY iPSCs with P63, TFAP2C, GATA2, KRT7 and DAPI for nuclei staining shows that markers characteristic of TSCs are is shown in FIG. 3c. FIG. 3d shows immunostaining of iTSCs generated from d21 naïve reprogramming intermediates.

Cells generated from D21 primed and naive intermediates were subjected to flow cytometry. APA+ITGA6+ double positive cells, gated from the TRA-1-60 negative cell population, which were sorted to purify iTSCs from the bulk reprogrammed cells (not shown). FIG. 3d also shows the percentage of TRA-1-60 negative, APA positive and ITGA6 positive iTSCs generated from D21 primed and naive reprogramming intermediates.

The level of expression of TSC markers was determined in human fibroblasts, primed iPSCs, naive iPSCs and iTSCs made according to the present invention, and compared with the TSCT and TSblast obtained from blastocysts (Okae et al., 2018). Results are shown in FIG. 3e.

ST cells were obtained by differentiating the TSCs made according to the present invention, using standard methods. Phase-contrast images and SDC1 immunostaining of the differentiated cells show that the cells exhibit characteristics of STs. (FIGS. 3f and 3g)

FIG. 3i shows positive results for ST cells differentiated from iTSCs using hCG pregnancy test sticks. ELISA was also used to detect the level of hCG secreted by TSCs made according to the present invention, and by STs obtained by differentiating those TSCs (FIG. 3j).

FIG. 3f shows phase-contrast images of EVT cells differentiated from iTSCs made according to the invention. HLA-G immunostaining was also performed (FIG. 3g).

An iTSC engraftment assay was performed by injecting iTSCs made according to the present invention, into NOD-SCID mice. The urine, lesions and blood serum were examined 9 days post-injection. FIG. 3k shows that urine samples collected from iTSC-injected mice showed positive hCG results on the pregnancy test sticks compared to the vehicle control. hCG levels were also detected by hCG ELISA using the blood serum samples (FIG. 3l).

FIG. 3n shows Hematoxylin and eosin and immunohistochemical staining of KRT7, SDC1 and HLA-G in the lesions harvested from iTSC-engrafted in NOD-SCID mice, no evident lesions were observed in vehicle controls.

FIG. 3m shows the results observed following engraftment of TSCs made according to the present invention, in NOD-SCID mice. Briefly, iTSCs with 80% confluency were dissociated with TrypLE express (ThermoFisher) and counted. $10^7$ iTSCs were resuspended in 200 µl of a 1:2 mixture of Matrigel (Corning) and DMEM/F-12, Gluta-MAX™ (ThermoFisher) supplemented with 0.3% BSA (Sigma) and 1% ITS-X supplement (ThermoFisher). The cellular mixture was then injected subcutaneously into dorsal flanks of NOD-SCID mice (100 µl mixture into each flank). At day 9 after injection, urine, lesions and serum were collected from the mice for analysis. Mice urine and serum were utilized for the detection and measurement of hCG secretion as detailed in the below section. Collected lesions were fixed with 4% Paraformaldehyde (PFA, Sigma) overnight and subsequently embedded in paraffin. Paraffin-embedded tissues were sectioned at 5 µm and stained with hematoxylin-eosin (H&E) or proceeded with immunostaining as described above.

Figure 4:
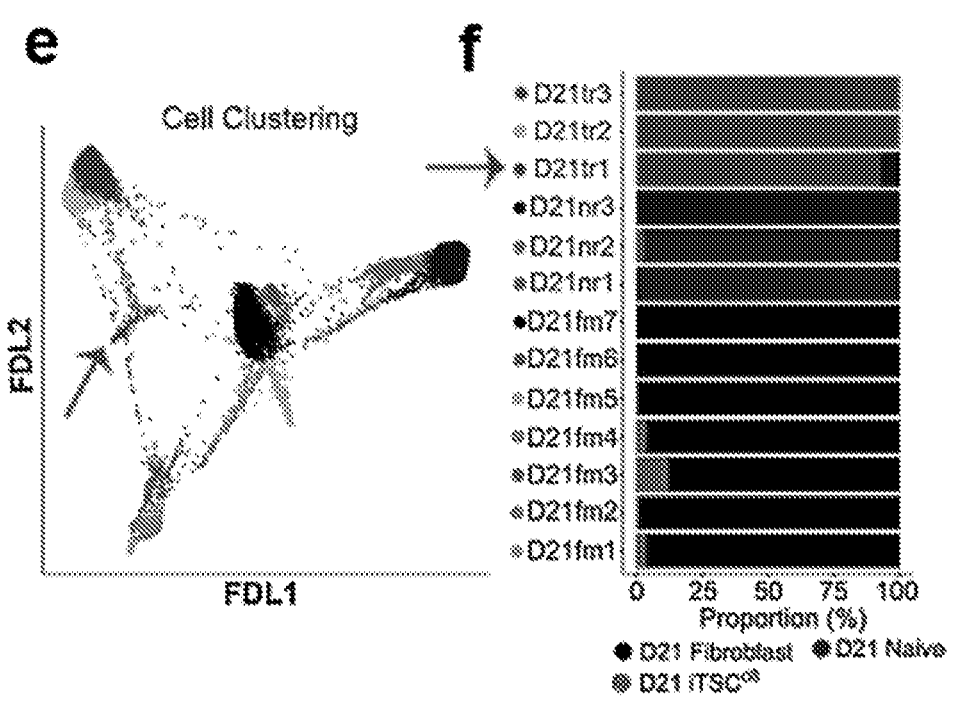
FIG. 4: Cellular heterogeneity of fibroblast and iTSCd8 reprogramming intermediates revealed by scRNA-seq. (a) Experimental designs and preparation of scRNA-seq libraries of day-21 fibroblast, naive and TSCd8 reprogramming intermediates. (b) FDL representation of scRNA-seq libraries of day-21 reprogramming intermediates (10,518 cells). (c) Strength of EPI signatures on FDL (10,518 cells). The cell population not enriched for EPI signatures but enriched for TE signatures is indicated by a purple arrow. (d) TE signatures on FDL projections. The TE-like population is highlighted and coloured by the library. (e) Representation of 13 cell clusters from unsupervised clustering projected onto the FDL, fibroblast medium cell clusters: D21fm1-D21fm7; naive reprogramming cell clusters: D21nr1-D21nr3; trophoblast reprogramming cell clusters: D21tr1-D21tr3. (f) Contribution of each scRNA-seq library (%) to the composition of cell clusters. D21tr1 cluster is indicated by a purple arrow.

FIG. 4 shows cellular heterogeneity of fibroblast and of reprogramming intermediates (iTSCd8) as revealed by scRNA-seq.

To test whether iTSCs could be derived directly from human fibroblasts, reprogramming experiments were commenced. The day-8 intermediates were transitioned into TSC medium or naive medium, or kept in fibroblast medium. scRNA-seq was then performed at day 21 to assess cellular heterogeneity (FIG. 4a). A population of TE-like cells was observed, and closer examination revealed that this TE-like population contained cells from all three reprogramming conditions (FIGS. 4b-d).

Example 4: Direct Derivation of iTSCs from Human Fibroblasts

Reprogramming of fibroblasts was commenced according to the methods described in Example 1. Briefly, at day 8 post-transfection with Sendai virus expressing transcription factors OKSM, cells were transferred to TSC media, as described herein (FIG. 5a).

Figure 5:
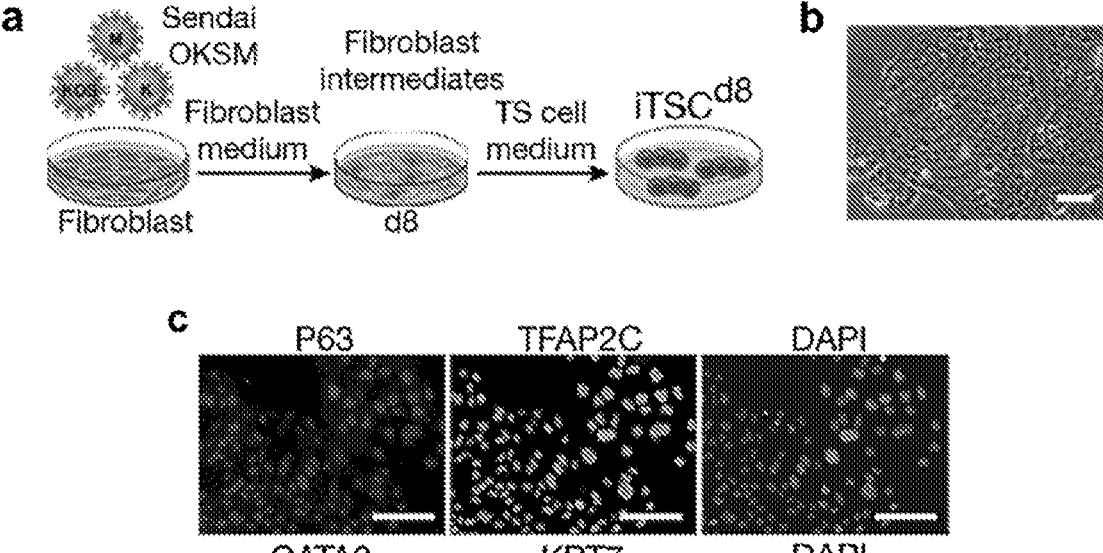
FIG. 5: Direct derivation of iTSCs from human fibroblasts. (a) Experimental design of direct derivation of iTSCd8 from fibroblasts. (b) Phase-contrast image of iTSCd8. Scale bar, 100 μm. (c) Immunostaining of iTSCd8 for several TS cell makers. Scale bar, 100 μm. (d) Sendai viral transgenes in iTS cell lines with positive and negative controls, n=6. (e) Gene expression of trophoblast genes in fibroblasts, primed iPS cells, naive t2iLGoY iPCs, iTSCd8 and iTSCd21n compared to TSCs derived from a human blastocyst (TSCblast) and first-trimester placental trophoblast (TSCCT), data are presented as mean (n=2). (f) Spearman correlation of transcriptomes from this study with published datasets. Biological replicates (n 2) are averaged before performing correlation. blast, blastocyst; blast/CT, blastocyst/cytotrophoblast; CT, cytotrophoblast. (g,h) Spearman correlation of the transcriptomes of fibroblast, primed and naive t2iLGoY iPS cells, iTSCd8 and iTSCd21n, iTSCd8 ST and iTSCd21n ST, iTSCd8 EVT and iTSCd21n EVT generated in this study with trophoblast organoids samples. (i) Expression of miRNAs of the chromosome 19 miRNA cluster, normalized to 1,000× expression of miR-103a, in the indicated cell lines. Mean±s.e.m. ND, not detected. Red dotted line indicates the level in primed iPS cells. n=2. (j) ATAC-seq signal at ELF5 region in the indicated cell types. Mean value of replicates (n=2). TS cell peaks are marked in grey. (k,l) Phase-contrast and immunostaining of ST (k) and EVT (l) cells differentiated from iTSCd8. Scale bar, 100 μm. n=4. (m) Cell fusion index of iTSCd8 ST and iTSCd8. n=5, data are mean±s.e.m. P values by two-tailed unpaired Student's t-test. (n) Representative results for hCG pregnancy test obtained from medium of ST cells differentiated from iTSCd8, n=6. (o) hCG levels of iTSCd8- and iTSCd8-ST-conditioned medium detected by ELISA, n=4. (p) Representative flow cytometry analysis of pan HLA-A, B, C class I marker (W6/32), HLA-Bw4 and HLA-G in fibroblasts and EVTs, n=4. (q) Representative flow cytometry analysis of pan HLA class I marker (W6/32)
Figure 5:
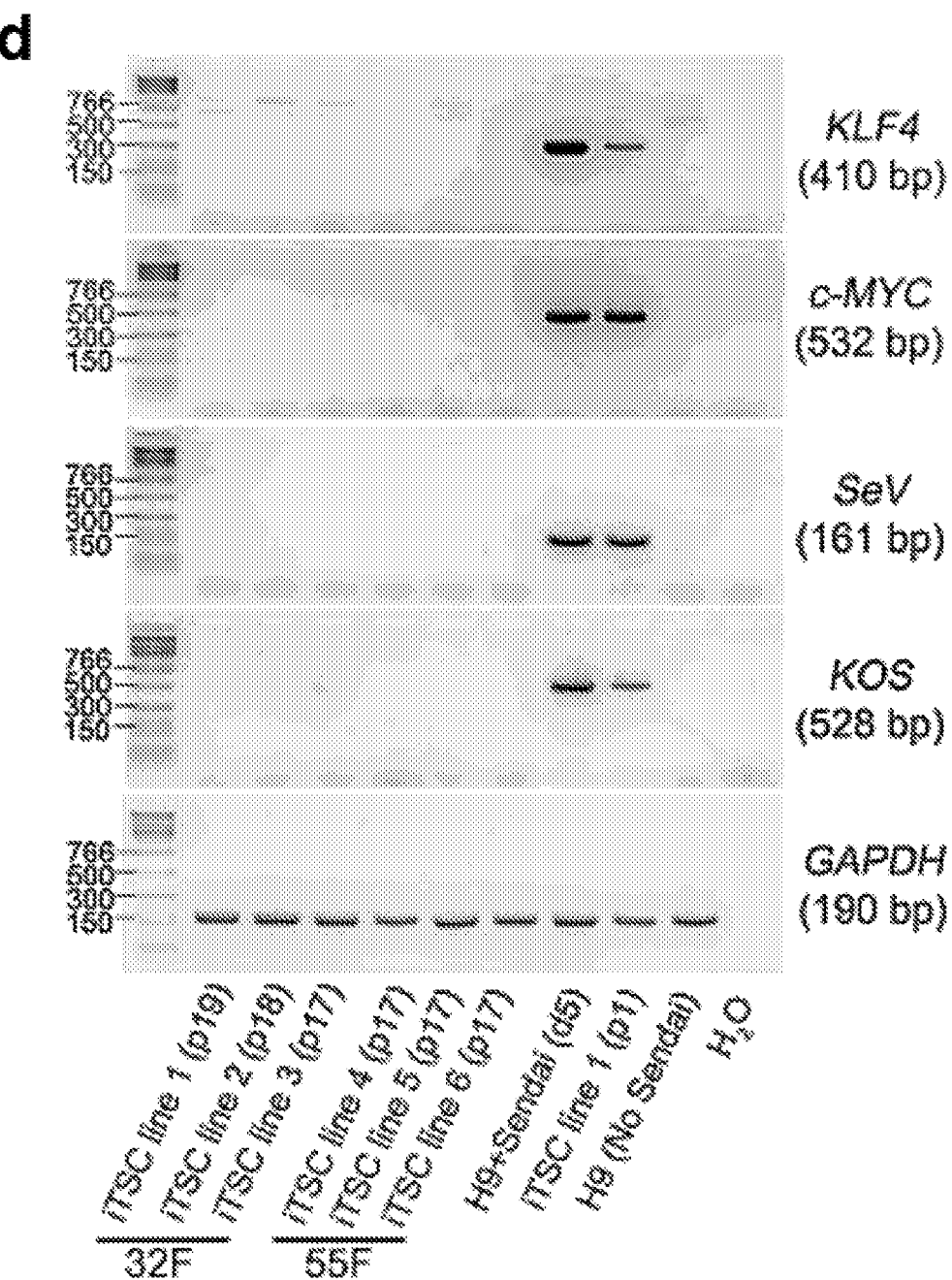
Figure 5:
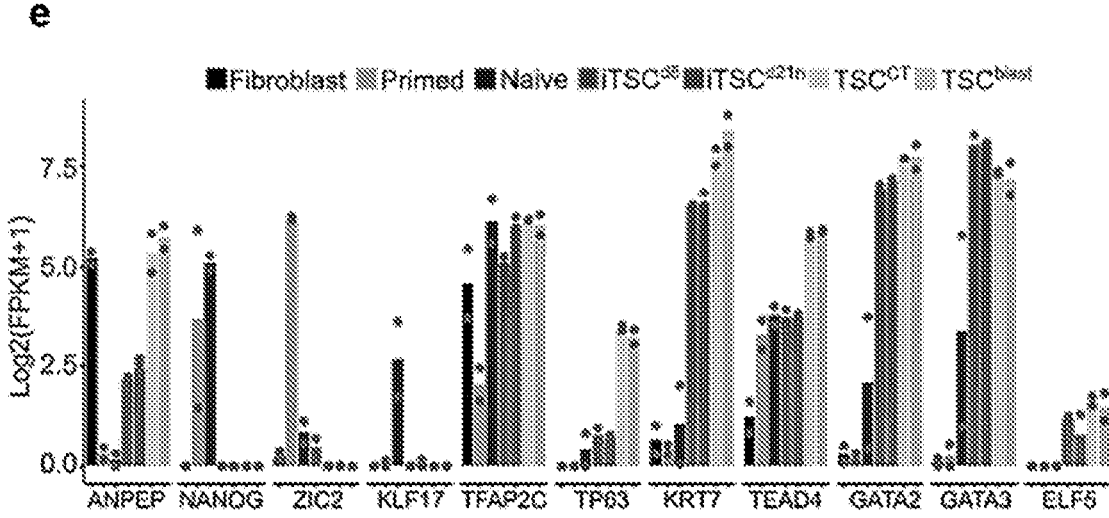
Figure 5:
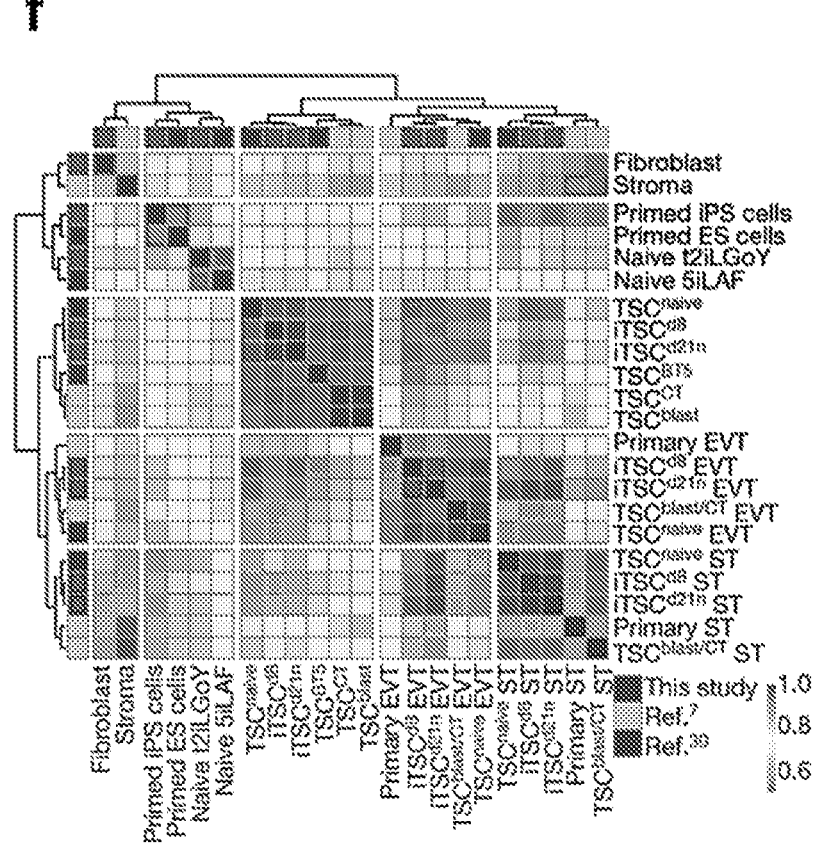
Figure 5:
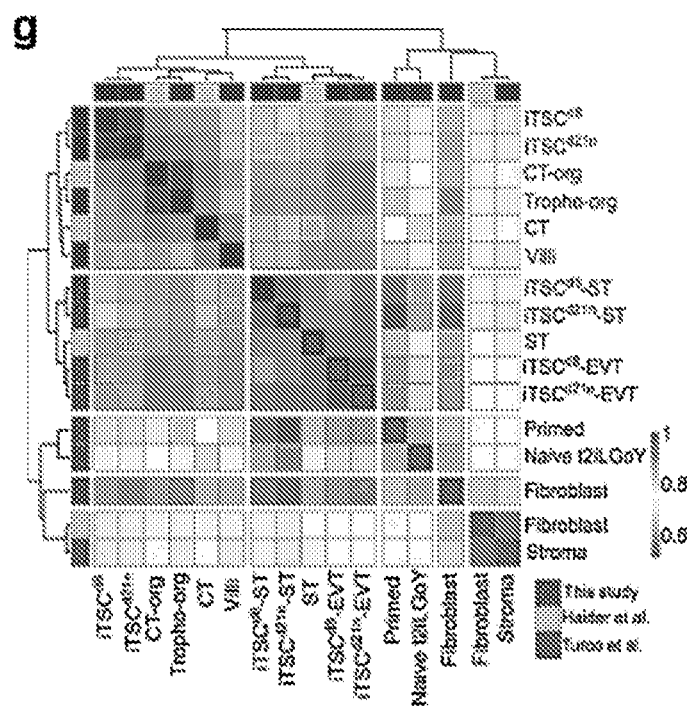
Figure 5:
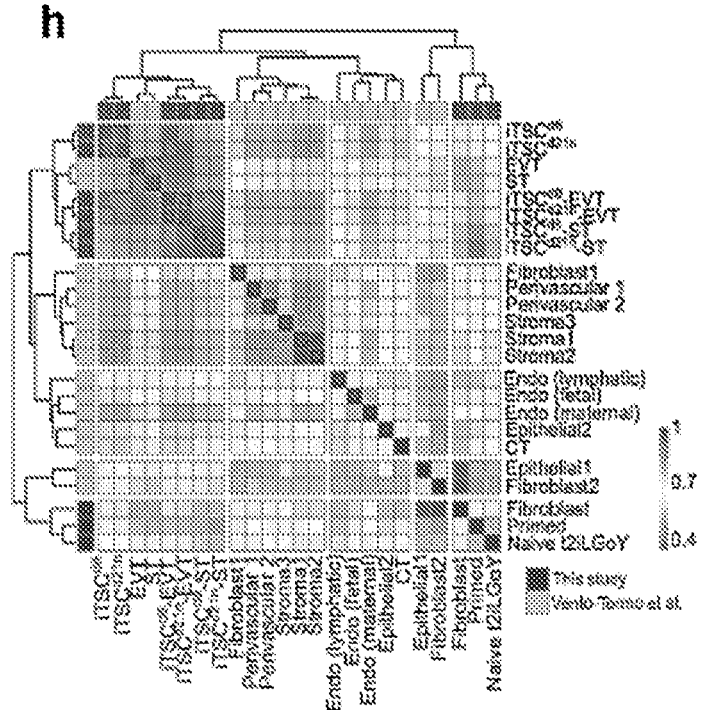
Figure 5:
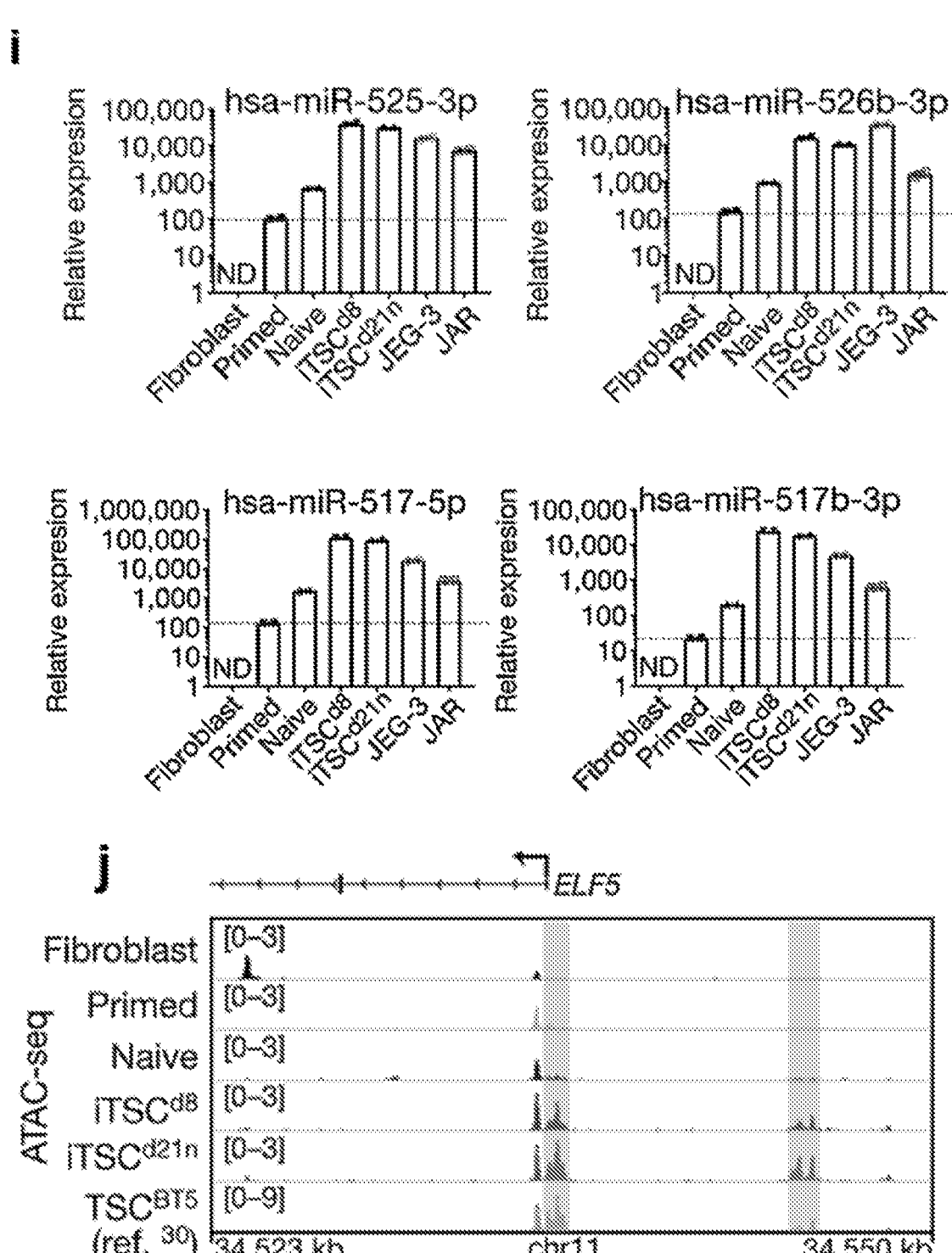
Figure 5:
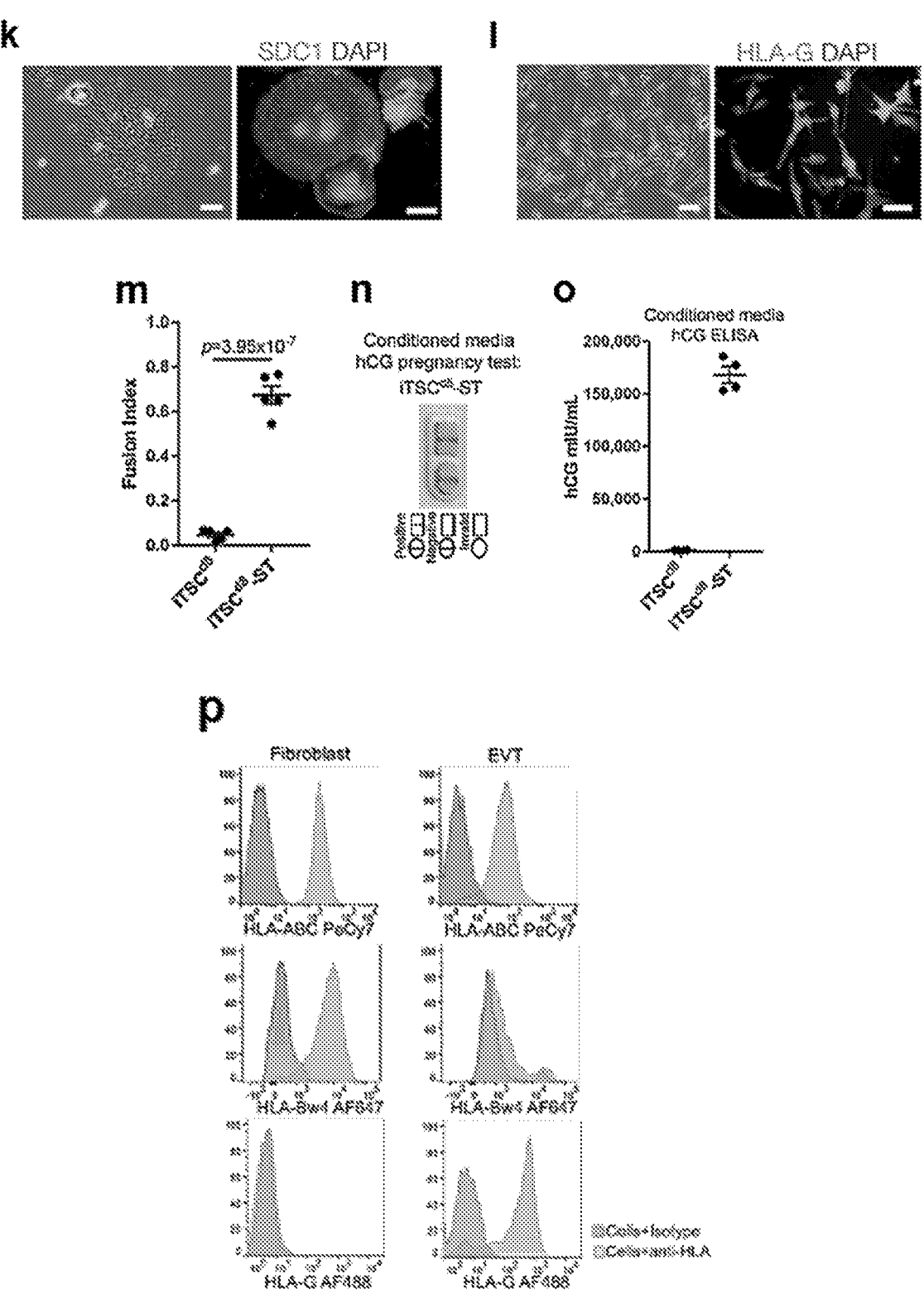
Figure 5:
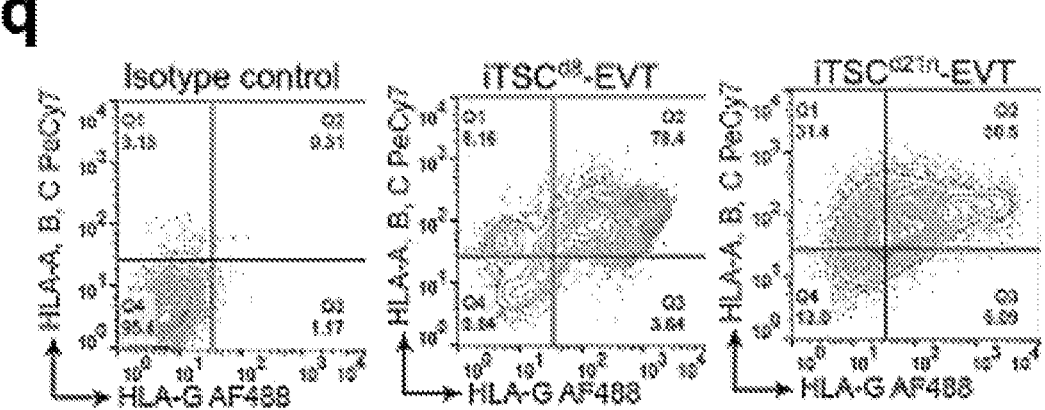
Figure 5:
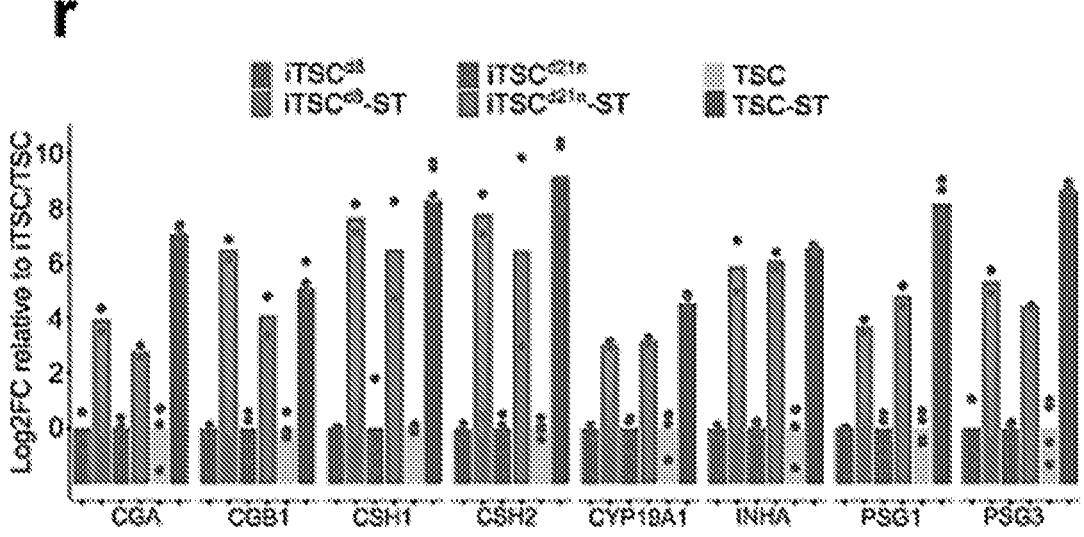
Figure 5:
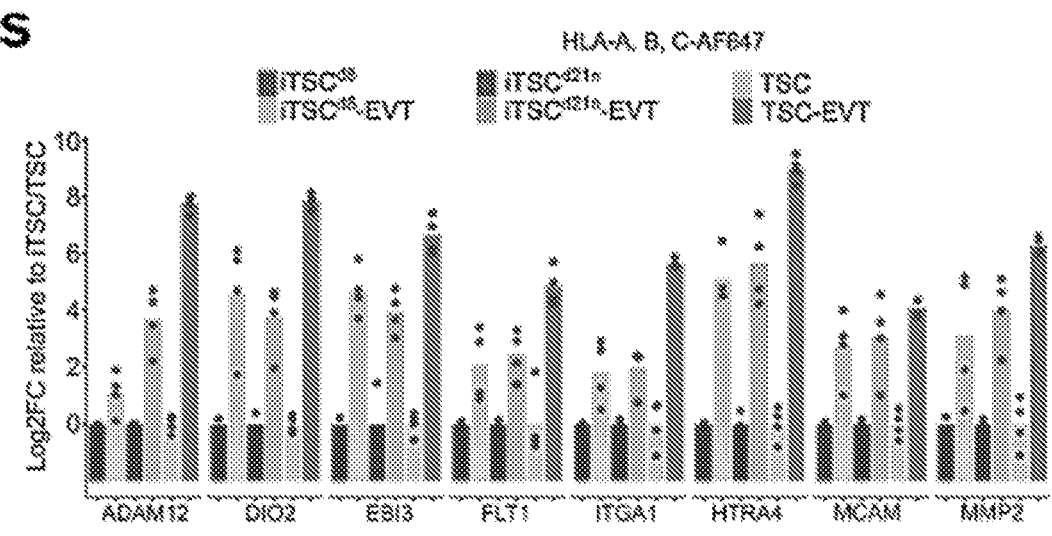
Figure 5:
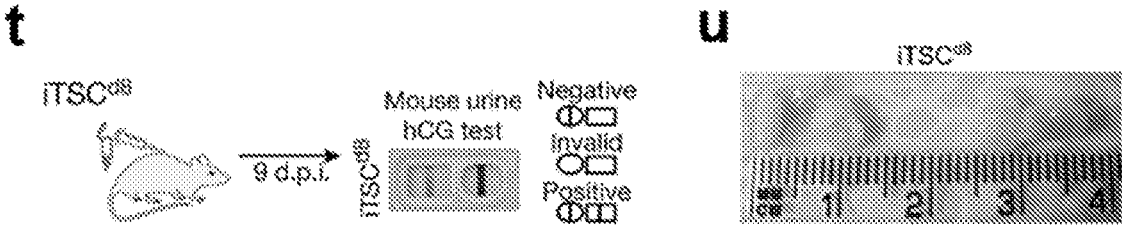
Figure 5:
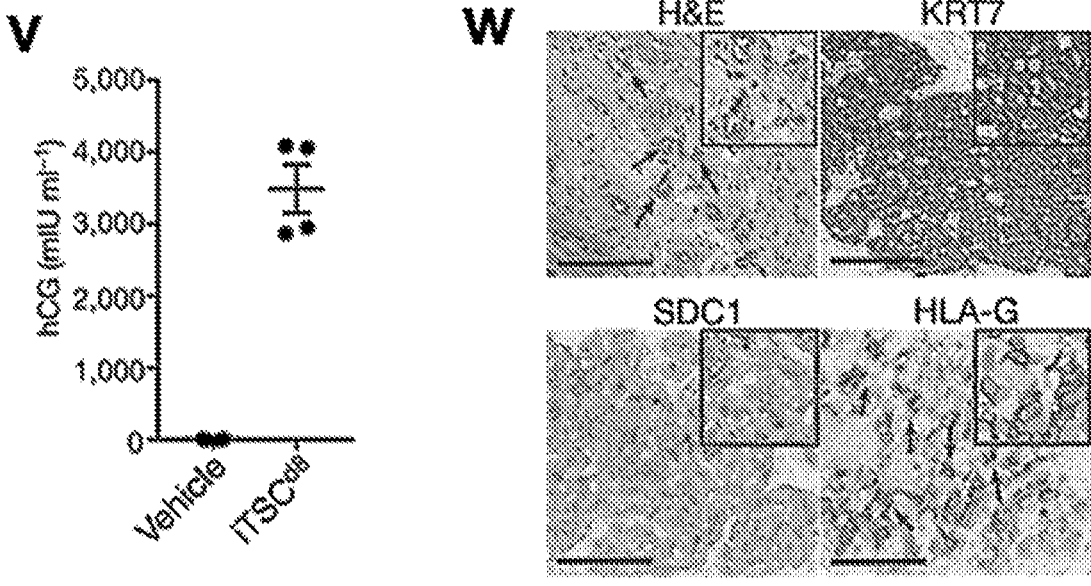

Phase-contrast images of cells generated via this process indicate that the cells have similar morphology to TSCs (cobblestone appearance, FIG. 5b).

FIG. 5c shows immunostaining of iTSCs generated from d8 fibroblast intermediates. These iTSCs can self-renew in transgene-free conditions (FIG. 5d).

The level of expression of TSC markers was determined in human fibroblasts, primed iPSCs, naive iPSCs and iTSCs made according to the present invention, and compared with the TSCT and TSblast obtained from blastocysts (Okae et al., 2018). Results are shown in FIG. 5e. Furthermore, iTSCs and iTSC-derived syncytiotrophoblasts (STs) and extravillous trophoblasts (EVTs) share a common transcriptomic profile with the corresponding primary cell types of other published datasets (FIGS. 5f-h).

iTSCs also show higher levels of expression of microRNAs (miRNAs) from the chromosome 19 miRNA cluster, compared to fibroblast and iPS cells—a unique feature of primary trophoblast (FIG. 5i).

iTSCs show specific open chromatin accessibility at the promoter and putative enhancer regions of the ELF5 locus as seen in TSCBT5 (which are derived from human blastocysts) (FIG. 5j).

ST cells were obtained by differentiating the iTSCs made according to the present invention, using standard methods. Phase-contrast images and SDC1 immunostaining of the differentiated cells show that the cells exhibit characteristics of STs (FIG. 5k).

FIG. 5n shows positive results for ST cells differentiated from iTSCs using hCG pregnancy test sticks. ELISA was also used to detect the level of hCG secreted by TSCs made according to the present invention, and by STs obtained by differentiating those iTSCs (FIG. 5o).

FIG. 5*l* shows phase-contrast images of EVT cells differentiated from iTSCs made according to the invention. HLA-G immunostaining was also performed (FIG. 5*l*). Furthermore, the expression of HLA-A, -B, -C pan marker (W632) was detected in iTS cells, similar to what was previously reported in TS cells derived from blastocysts (Okae et al., 2018) (FIGS. 5*p* and 5*q*).

FIGS. 5*r* and 5*s* show that iTS-cell-derived syncytiotrophoblasts and extravillous trophoblasts show expression of the relevant marker genes.

FIG. 5*t* shows a schematic representation of an iTSC engraftment assay was performed by injecting iTSCs made according to the present invention, into NOD-SCID mice. The urine, lesions and blood serum were examined 9 days post-injection. FIG. 5*t* shows that urine samples collected from iTSC-injected mice showed positive hCG results on the pregnancy test sticks compared to the vehicle control. hCG levels were also detected by hCG ELISA using the blood serum samples (FIG. 5*v*).

FIG. 5*w* shows Hematoxylin and eosin and immunohistochemical staining of KRT7, SDC1 and HLA-G in the lesions harvested from iTSC-engrafted in NOD-SCID mice, no evident lesions were observed in vehicle controls.

FIG. 5*u* shows the results observed following engraftment of TSCs made according to the present invention, in NOD-SCID mice. Briefly, iTSCs with 80% confluency were dissociated with TrypLE express (ThermoFisher) and counted. 107 iTSCs were resuspended in 200 µl of a 1:2 mixture of Matrigel (Corning) and DMEM/F-12, Gluta-MAX™ (ThermoFisher) supplemented with 0.3% BSA (Sigma) and 1% ITS-X supplement (ThermoFisher). The cellular mixture was then injected subcutaneously into dorsal flanks of NOD-SCID mice (100 µl mixture into each flank). At day 9 after injection, urine, lesions and serum were collected from the mice for analysis. Mice urine and serum were utilized for the detection and measurement of hCG secretion as detailed in the below section. Collected lesions were fixed with 4% Paraformaldehyde (PFA, Sigma) overnight and subsequently embedded in paraffin. Paraffin-embedded tissues were sectioned at 5 µm and stained with hematoxylin-eosin (H&E) or proceeded with immunostaining as described above.

Example 5: Derivation of iTSCs from Day21 Human Fibroblast Reprogramming Intermediates Reprogramming of fibroblasts was commenced according to the methods described in Example 1. Briefly, at day 21 post-transfection with Sendai virus expressing transcription factors OKSM, cells were transferred to TSC media, as described herein.

The day-21 fibroblast-medium intermediates also consist of cells with strong epiblast, primed and naive signatures, and accordingly these intermediates were able to give rise to pluripotent and TS cell lines (FIGS. 6*a-c*).

Example 6: Derivation of iTSCs from Partially Reprogrammed Intermediates, and from Established Naïve and Extended iPSCs into TSCs Reprogramming of fibroblasts to obtain reprogramming intermediates was commenced according to the methods described in Example 1. Briefly, at day 7 post-transfection with Sendai virus expressing transcription factors OKSM, cells were transferred to E7 media, as described herein. FIG. 7*a* shows a schematic representation of the reprogramming protocol and Phase contrast images of the cells at each stage.

TSCs obtained from established naïve and extended iPSCs were obtained according to the methods described in Example 2. A schematic of the conversion protocol and Phase contrast images of cells at each stage are shown in FIG. 7*b*.

FIG. 7*c* shows hierarchical clustering defined 3 groups of cells: (1) naive hPSC, (2) extended and primed hPSC, and (3) trophoblasts. Both induced and converted hTSC clustered together with previously established embryo- and placenta-derived hTSC to form the group of trophoblasts. This group subdivided between either hTSC comprising established, induced and converted hTSC ST and EVT. Pearson correlation analysis further confirmed the proximity of induced, converted, embryo- and placenta-derived hTSC. Extended and primed hPSC showed a high degree of transcriptional similarity, despite relative differences in their potential to form hTSC.

Further analysis confirmed that induced and converted hTSC expressed key trophoblast lineage markers. Notably, the expression levels of GATA3, KRT7 and VGLL1 were similar to those found in previously established embryo- and placenta-derived hTSC (absolute gene expression ranging from 10 to 300 UPM). We also identified genes associated with stemness of hTSC, including PEG10, NR2F2, and LRP2. These were expressed at similar levels in hTSC, hiTSC and hcTSC, but not in the differentiated ST and EVT (absolute gene expression ranging from 20 to 200 UPM in hTSC, below 10 UPM in hTSC-ST and hTSC-EVT) (FIG. 7*d*).

Figure 1:
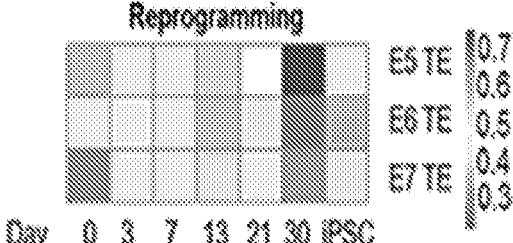
FIG. 1: Trophectoderm (TE) signature is upregulated during human reprogramming. a) Heatmap of the strength of the TE gene signature, defined by Petropoulos et al (2016), Cell, 165: 1012-26, during the reprogramming of fibroblasts into naive iPSCs. (b) In vivo TE signatures on FDL projection overlaid with single-cell trajectories constructed using Monocle3 (black lines). Blue arrow indicates the TE-enriched cell population. (c) Gene set enrichment analysis (GSEA) (Methods) of the EPI, PE and TE gene signatures in reprogramming intermediates and iPS cells reprogrammed under primed and several naive culture conditions. (d) Standardized gene expression (averaged z-scaling) of genes associated with ATAC-seq cluster peaks. (e) Transcription factor motif enrichment analysis of the ATAC-seq peak clusters. Motif enrichment (−log(P value)) heat map by colour and the size the percentage of sequences in the cluster featuring the motif. Red arrow points to OCT4, SOX2, NANOG and KLF4 motifs in transient ATAC-seq cluster (C3), Blue arrow=enrichment of TE-associated transcription factors TFAP2C and GATA2 (C7 and C8) are indicated by blue arrows.
Figure 1:
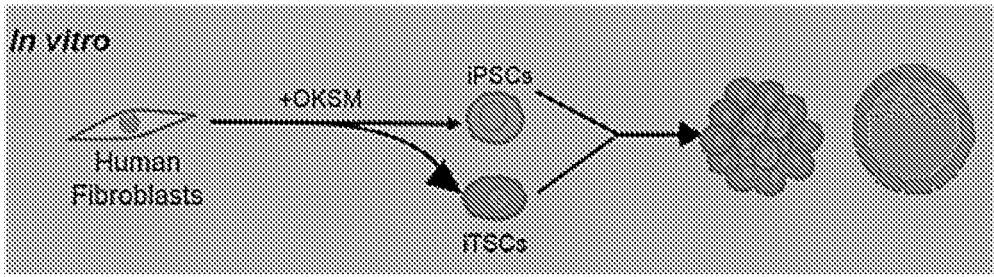
Figure 1:
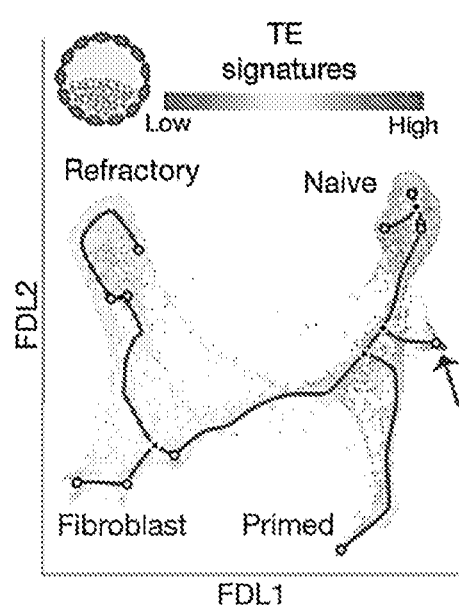
Figure 1:
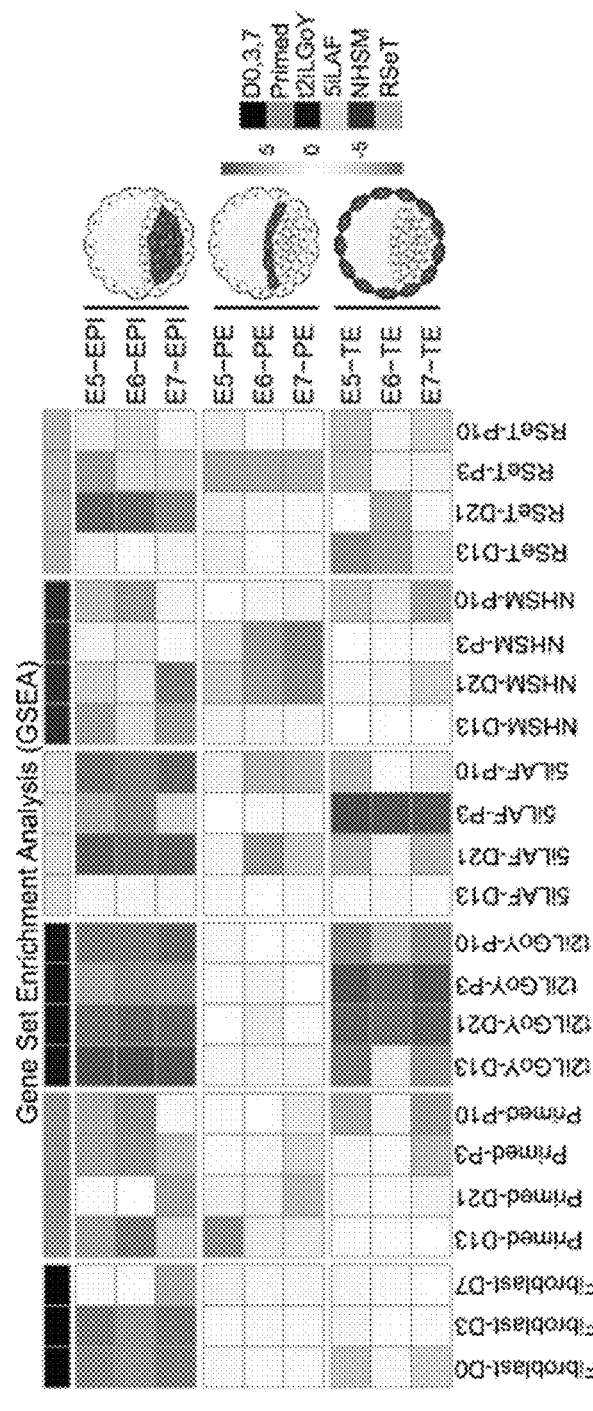
Figure 1:
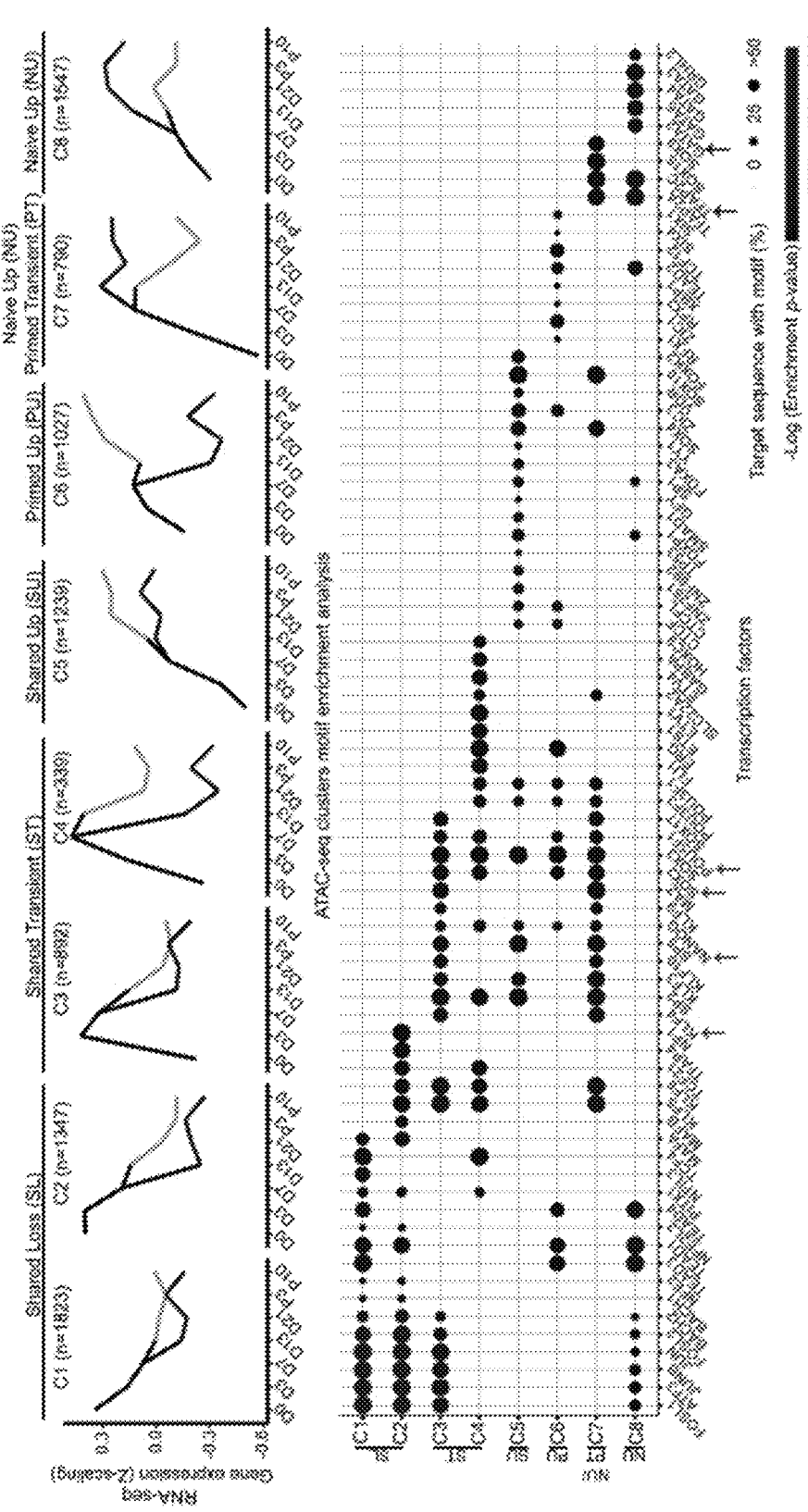

FIG. 7*e* shows immunostaining of hiTSC and hcTSC for the trophoblast markers NR2F2 and GATA2 that are expressed in the trophectoderm of human blastocysts. NR2F2 and GATA2 were highly expressed and localized in the nuclei of all cells. Conversely, SOX2 was highly expressed in hPSC, but absent in hTSC (FIG. 1*e*). These expression patterns were comparable between hiTSC, hcTSC and placenta-derived hTSC. These results confirm that hi/cTSC share similar expression profiles with previously-established hTSC.

FIGS. 7*f-g* show ST/EVT assays optimisation protocols. Upon optimized ST differentiation, cells upregulated the expression of CGA, CGB and SDC1, which are not expressed in hTSC (relative gene expression ranging from 10 to 1300-fold change). In contrast, HLA-G, MMP2, and ASCL2 were globally increased in the EVT differentiation condition (relative gene expression ranging from 10 to 700-fold change). Finally, LRP2 and CDKN3 predominantly expressed in hTSC were downregulated upon differentiation (relative gene expression ranging from 2 to 70-fold change). Importantly, gene expression patterns were comparable with those of placental cells, which was confirmed by statistical analysis (FIG. 7*h*).

FIG. 7*i* shows structures of multinucleated syncytia expressing DESMOPLAKIN (DSP) and CGB, and typically containing 6 to 10 nuclei.

Immunostaining for GATA3 and HLA-G confirmed the identity of EVT differentiated from induced, converted and placenta-derived hTSC (FIG. 7*j*)

Example 7: General Methods

Cell Culture Conditions

Primary human adult dermal fibroblasts from three female donors were obtained from ThermoFisher (catalogue number C-013-5C and lot no. 1029000 for 38F, lot no. 1528526 for 55F and lot no. 1569390 for 32F); cells were recovered and plated in medium 106 (ThermoFisher) supplemented with low serum growth supplement (LSGS) (ThermoFisher) for expansion. Culture conditions used for human somatic cell reprogramming were prepared as previously described. Fibroblast medium: DMEM (ThermoFisher), 10% fetal bovine serum (FBS) (Hyclone), 1% nonessential amino acids (ThermoFisher), 1 mM GlutaMAX (ThermoFisher), 1% penicillin-streptomycin (ThermoFisher), 55 µM 2-mercaptoethanol (ThermoFisher) and 1 mM sodium pyruvate (ThermoFisher). Primed medium: DMEM/F12 (ThermoFisher), 20% knockout serum replacement (KSR) (ThermoFisher), 1 mM GlutaMAX (ThermoFisher), 0.1 mM 2-mercaptoethanol (ThermoFisher), 1% non-essential amino acids (ThermoFisher), 50 ng/ml recombinant human FGF2 (Miltenyi Biotec), 1% penicillin-streptomycin (ThermoFisher). Naive medium (t2iLGoY): 50:50 mixture of DMEM/F-12 (ThermoFisher) and neurobasal medium (ThermoFisher), supplemented with 2 mM l-glutamine (ThermoFisher), 0.1 mM 2-mercaptoethanol (ThermoFisher), 0.5% N2 supplement (ThermoFisher), 1% B27 supplement (ThermoFisher), 1% penicillin-streptomycin (ThermoFisher), 10 ng/ml human leukaemia inhibitory factor (LIF) (made in-house), 250 µM l-ascorbic acid (Sigma), 10 µg/ml recombinant human insulin (Sigma), 1 µM PD0325901 (Miltenyi Biotec), 1 µM CHIR99021 (Miltenyi Biotec), 2.5 µM Gö6983 (Tocris), 10 µM Y-27632 (Abcam). Naive human stem cell medium (NHSM): culture condition adapted from Gafni, O. et al. Derivation of novel human ground state naive pluripotent stem cells. Nature 504, 282-286, with suggested modifications from the web page of the J. Hanna laboratory in 2014 was used. DMEM/F12 (ThermoFisher) supplemented with 10 mg/ml AlbuMAX I (ThermoFisher), 1% penicillin-streptomycin (ThermoFisher), 1 mM GlutaMAX (ThermoFisher), 1% nonessential amino acids (ThermoFisher), 10% KSR (ThermoFisher), 1% N2 supplement (ThermoFisher), 12.5 µg/ml recombinant human insulin (Sigma), 50 µg/ml l-ascorbic acid (Sigma), 20 ng/ml of recombinant human LIF (made in-house), 8 ng/ml FGF2 (Peprotech), 2 ng/ml recombinant TGFβ1 (Peprotech), 20 ng/ml human LR3-IGF1 (Prospec) and small molecule inhibitors: 1 µM PD0325901 (Miltenyi Biotec), 3 µM CHIR99021 (Miltenyi Biotec), 5 µM SP600125 (Tocris) 2 µM BIRB796 (Axon), 0.4 µM LDN193189 (Axon), 10 µM Y-27632 (supplemented daily to media from freshly thawed stock aliquot) (Abcam) and 1 µM Gö6983 (supplemented daily to media from freshly thawed stock aliquot) (Tocris). Naive 5iLAF medium: 50:50 mixture of DMEM/F-12 (ThermoFisher) and neurobasal medium (ThermoFisher) supplemented with 1% N2 supplement (ThermoFisher), 2% B27 supplement (ThermoFisher), 1% nonessential amino acids (ThermoFisher), 1 mM GlutaMAX (ThermoFisher), 1% penicillin-streptomycin (ThermoFisher), 0.1 mM 2-mercaptoethanol (ThermoFisher), 50 µg/ml bovine serum albumin (ThermoFisher), 1 µM PD0325901 (Miltenyi Biotec), 1 µM IM-12 (Millipore), 0.5 µM SB590885 (Tocris), 1 µM WH-4-023 (A Chemtek), 10 µM Y-27632 (Abcam), 20 ng/ml activin A (Peprotech), 8 ng/ml FGF2 (Miltenyi Biotec), 20 ng/ml human LIF (made in-house) and 0.5% KSR (ThermoFisher). Naive RSeT medium: 100 ml of RSeT 5× supplement, 1 ml of RSeT 500× supplement and 0.5 ml of RSeT 1,000× supplement into 398.5 ml of RSeT basal medium (Stem Cell Technologies) supplemented with 1% penicillin-streptomycin (ThermoFisher). Human TS cell medium7: DMEM/F-12, GlutaMAX (ThermoFisher) supplemented with 0.3% BSA (Sigma), 0.2% FBS (ThermoFisher), 1% ITS-X supplement (ThermoFisher), 0.1 mM 2-mercaptoethanol (ThermoFisher), 0.5% penicillin-streptomycin (ThermoFisher), 1.5 µg/ml l-ascorbic acid (Sigma), 5

µM Y27632 (Abcam), 2 µM CHIR99021 (Miltenyi Biotec), 0.5 µM A83-01 (Sigma), 1 µM SB431542, 50 ng/ml EGF (Peprotech) and 0.8 mM valproic acid (VPA) (Sigma).

Reprogramming Experiments

The t2iLGoY medium was used for naive reprogramming, as it has previously been shown that this medium can be used to reprogram fibroblasts into naive iPS cells that possess all the hallmarks of naïve pluripotency and maintain a more stable karyotype when compared to other conditions. Human somatic cell reprogramming into primed and naive pluripotent states experiments and the subsequent culture of primed and naive iPS cells were performed as previously described. In brief, the reprogramming of human fibroblasts was conducted using CytoTune-iPS 2.0 Sendai reprogramming kit, according to the manufacturer's instructions (ThermoFisher).

Primary human adult dermal fibroblasts were seeded at a density of about $5\text{-}10 \times 10^4$ cells in fibroblast medium. Cells were transduced with Sendai viruses in fibroblast medium at a multiplicity of infection (MOI) as follows: KLF4, OCT4 and SOX2, MOI=5 or 10; MYC, MOI=5 or 10; and KLF4 MOI=6 or 12. Cells were reseeded onto a layer of iMEF feeders on day 7 and transitioned into different culture media (primed, t2iLGoY, NHMS, RSeT or 5iLAF) the next day. After 18-21 days, iPSCs could be passaged and expanded as previously described. For the derivation of iTSCd21n during primed or naïve reprogramming, day-21 primed or naive t2iLGoY reprogramming intermediates were transitioned into TS cell medium. After 4-5 days, cells were passaged using TrypLE express (ThermoFisher) every 3-4 days at a 1:2-1:4 ratio. For the initial 4 passages, iTSCs were passaged onto iMEF feeders and cultured in a 37-° C., 5% $O_2$ and 5% $CO_2$ incubator.

Starting from passage 5, iTSCd21n were passaged onto a tissue culture flask that was pre-coated with 5 µg/ml collagen IV (Sigma) (for at least 1 h at 37° C.) and cultured in a 37° C., 20% $O_2$ and 5% $CO_2$ incubator. For the direct derivation of iTSCd8 from human fibroblasts, day-8 fibroblast reprogramming intermediates were transitioned into TSC medium. After 10-13 days, iTSCd8 were passaged onto iMEF feeders and cultured in a 37° C., 5% $O_2$ and 5% $CO_2$ incubator as described for iTSCd21n. Sendai detection in established iTSC lines was performed as described in the Sendai reprogramming protocol (ThermoFisher). For the derivation of primed, naive iPSCs and iTSCs from day-21 fibroblast reprogramming intermediates, day-21 fibroblast reprogramming intermediates were transitioned into primed, naive or TSC medium, and then cultured and expanded as described.

For data present in FIG. 7, Human adult fibroblasts were reprogrammed using the CytoTune-iPS 2.0 Sendai reprogramming kit (Life Technologies™). Two days before infection, 3.0 to $4.0 \times 10^4$ fibroblasts were seeded per well on a 12-well plate, coated with Matrigel. At day 0, cells were infected with the three vectors: polycistronic Klf4-Oct4-Sox2, Myc and Klf4 at a 5:5:3 or 3:3:3 multiplicity of infection (MOI) respectively. At day 9 of infection, cells were dissociated with TrypLE (5 min, 37° C., Life Technologies™) and seeded in 35 mm dishes, on MEFs. On the following day, cells were transited into E7 reprogramming medium (STEMCELL Technologies™). From day 21 onwards, cells were transited into hTSC medium. Induced hTSC lines (hiTSC) were routinely cultured at 37° C. in hypoxic conditions (5% O2, 5% CO2). Somatic cell reprogramming to hiNPSC, hiEPS and hiPSC was performed as described in previous reports (Kilens et al., 2018 Nature Communications 9: 360; Yang et al., 2017, Cell, 169: 243-257).

Conversion of hNPSC and hEPS to hcTSC hNPSC and hEPS were dissociated with TrypLE (5 min, 37° C., Life Technologies™) and seeded in 35 mm dishes, on MEFs, at a density of 0.6 to $1.7\times10^5$ cells per dish. Cells were maintained in their initial medium supplemented with 10 μM Y27632 for 1 day. From day 2 onwards, cells were transited into hTSC medium. Converted hTSC lines (hcTSC) were routinely cultured at 37° C. in hypoxic conditions (5% O2, 5% CO2). Primed hPSC included in conversion experiments were initially cultured in KSR+ FGF2 or iPS-BREW. 10 colonies were picked (KSR+FGF2) or cells were passaged with TrypLE (iPS-BREW) and seeded at a density of 0.5 to $1.25\times10^5$ cells per dish in 35 mm dishes coated with MEFs for conversion assays.

Differentiation of iTSCd21n and iTSCd8 into ST and EVT In Vitro

Differentiation of iTSCs into ST and EVT was performed as previously described (Okae, H. et al. (2018) Derivation of human trophoblast stem cells. Cell Stem Cell 22, 50-63). For the differentiation of iTSCs into ST, iTSCs were seeded at a density of $1\times10^5$ cells per well onto a 6-well plate pre-coated with 2.5 μg/ml collagen IV (Sigma) and cultured in 2 ml of ST differentiation medium (DMEM/F-12, GlutaMAX (ThermoFisher) supplemented with 0.3% BSA (Sigma), 4% KSR (ThermoFisher), 1% ITS-X supplement (ThermoFisher), 0.1 mM 2-mercaptoethanol (ThermoFisher), 0.5% penicillin-streptomycin (ThermoFisher), 2.5 μM Y27632 (Abcam) and 2 μM forskolin (Selleckchem)). Media were replaced daily for the initial 4 days, and cells were analysed on day 6. The fusion index was used to quantify the efficiency of cell fusion, which is calculated by using the number of nuclei counted in the syncytia minus the number of syncytia, then divided by the total number of nuclei counted. For the differentiation of iTSCs into EVT, iTSCs were seeded at a density of $0.75\times105$ cells per well onto a 6-well plate pre-coated with 1 μg/ml collagen IV (Sigma) and cultured in 2 ml of EVT differentiation medium (DMEM/F-12, GlutaMAX (ThermoFisher) supplemented with 0.3% BSA (Sigma), 4% KSR (ThermoFisher), 1% ITS-X supplement (ThermoFisher), 0.1 mM 2-mercaptoethanol (ThermoFisher), 0.5% penicillin-streptomycin (ThermoFisher), 2.5 μM Y27632 (Abcam), 100 ng/ml NRG1 (Cell Signaling) and 7.5 μM A83-01 (Sigma). Shortly after suspending the cells in the EVT differentiation medium, Matrigel (Corning) was overlaid to a 2% final concentration. On day 3 of differentiation, EVT differentiation medium without human NRG1 (Cell Signaling) and Matrigel (Corning) was added to a final concentration of 0.5%. On day 6 of differentiation, EVT differentiation media were replaced without NRG1 (Cell Signaling) or KSR (ThermoFisher), and Matrigel (Corning) was added to 0.5% final concentration. The cells were cultured for an additional 2 d before analyses were performed.

Differentiation of Hi/c TSC to EVT and ST

After at least 15 passages, cells were collected for differentiation assays. Prior to differentiation into ST and EVT, h(i/c)TSC (initially cultured on MEFs) were transited to fibronectin for at least 3 passages. EVT differentiation: 2-4 days before passage, h(i/c)TSC were transited into pre-EVT medium [DMEM/F12 supplemented with 0.1 mM 2-mercaptoethanol, 0.5% penicillin-streptomycin, 0.3% BSA, 1% ITS-X supplement, 4% KSR, 7.5 μM A83-01 (Tocris™), 2.5 μM Y27632, 5 μM IWR-endo-1 (Miltenyi Biotec™)]. Then, cells were passaged with TrypLE to a density of 0.8 to $3.0\times10^4$ cells/cm². Before treatment was initiated, cells were placed in differentiation basal medium [DMEM/F12 containing 0.1 mM 2-mercaptoethanol, 0.5% Penicillin-Streptomycin, 0.3% BSA, 1% ITS-X], supplemented with 10 μM ROCK inhibitor (Y27632). Within 6 hours, timing depending on the lines, cells were transited into EVT medium (Okae et al., 2018) [Differentiation basal medium, supplemented with 100 ng/ml NRG1, 7.5 mM A83-01, 2.5 mM Y27632, 4% KnockOut Serum Replacement, 2% Matrigel]. At day 3, medium was replaced with the EVT medium containing 0.5% Matrigel, without NRG1. Typically, EVT formation was observed by day 4-5. At day 6, medium was replaced with the EVT medium containing 0.5% Matrigel, without NRG1 and KSR. Cells were collected on day 8 for subsequent analyses. 2D-ST differentiation: h(i/c)TSC were passaged with TrypLE to a density of 2.0 to $6.0\times10^4$ cells/cm². Before treatment was initiated, cells were placed in differentiation basal medium [DMEM/F12 containing 0.1 mM mercaptoethanol, 0.5% Penicillin-Streptomycin, 0.3% BSA, 1% ITS-X], supplemented with 10 μM ROCK inhibitor (Y27632). Within 3 hours, timing depending on the lines, cells were transited into ST medium (Okae et al., 2018) [Differentiation basal medium, supplemented with 2.5 mM Y27632, 2 mM forskolin, and 4% KSR]. Medium was replaced at day 3, and cells were analyzed at day 6. 3D-ST differentiation: Prior to 3D differentiation assay, h(i/c)TSC were transited to trophoblast organoid medium (TOM) with small modifications (Turco et al., 2018) [DMEM/F12, 1×N2 supplement, 1×B27 supplement minus vitamin A, 1.25 mM N-Acetyl-L-cysteine, 1% GlutaMAX (Gibco™), 0.5% Penicillin-Streptomycin (TOM basal medium), supplemented with 500 nM A83-01, 1.5 μM CHIR99021, 80 ng/ml human R-spondin1, 50 ng/ml hEGF, 100 ng/ml hFGF2, 50 ng/ml hHGF, 2 μM Y-27632]. 0.4 to $1.0\times10^5$ cells passaged with TrypLE were embedded into 150 μl drops comprising: 50 μl Matrigel and 50 μl PBS+/+ along with 960 ng fibronectin, 50 ng laminin521 and 50 μl TOM basal medium. Drops were carefully deposited on sterile parafilm covered dishes and placed at 37° C. for 20 minutes to solidify. Complete TOM supplemented with 10 μM ROCK inhibitor (Y27632) was further added to cover the drops. Medium was replaced every 3 days with TOM. The 3D structures emerged within a week and were collected on day 14 for subsequent analyses.

iTSCd21n and iTSCd8 In Vivo Engraftment Assay

Protocols and use of mice were undertaken with the approval of the Monash University Animal Welfare Committee following the 2004 Australian Code of Practice for the Care and Use of Animals for Scientific Purposes and the Victorian Prevention of Cruelty to Animals Act and Regulations legislation. iTS cells with 80% confluency were dissociated with TrypLE express (ThermoFisher) and counted. Ten million iTS cells were resuspended in 200 μl of a 1:2 mixture of Matrigel (Corning) and DMEM/F-12, GlutaMAX (ThermoFisher) supplemented with 0.3% BSA (Sigma) and 1% ITS-X supplement (ThermoFisher). The cellular mixture was then injected subcutaneously into dorsal flanks of male and female, 5-20-week-old NOD/SCID IL-2R-gamma knockout mice (100 μl into each flank). Mice were randomized between controls and iTS cells, but investigators were not blinded. Nine days after injection, urine, blood serum and lesions were collected from the mice for analysis. Mice urine and serum were used for the detection and measurement of hCG secretion as detailed in 'Pregnancy tests and hCG ELISA'. Collected lesions were fixed with 4% paraformaldehyde (PFA) (Sigma) overnight and subsequently embedded in paraffin. Lesions collected were less than 1 cm³ in volume. Paraffin-embedded tissues were sectioned and stained with haematoxylin and eosin (H&E) or proceeded with immunohistochemistry staining of KRT7, HLA-G and SDC1.

Pregnancy Tests and hCG ELISA iTSCs were seeded at a density of 0.5×10⁵ cells per ml on a 12-well plate for ST differentiation as detailed in 'Differentiation of iTSCd21n and iTSCd8 into ST and EVT in vitro'. The medium of the ST cells was replaced on day 4 and the conditioned medium was collected at day 6 and stored at −80° C. As a control, iTSCs were also seeded at a density of 0.5×10⁵ cells per ml on a 12-well plate and cultured in TSC medium. Two days later, the conditioned medium was collected and stored at −80° C. The conditioned media were then tested using over-the-counter hCG pregnancy test sticks (Freedom) according to the manufacturer's recommendations. In addition, the hCG level within the medium was also measured using hCG ELISA kit (Abnova, ABNOKA4005) according to the manufacturer's instructions. Following the iTSC engraftment assay, the collected mouse urine was tested using the over-the-counter hCG pregnancy test sticks and hCG level in blood serum was measured using hCG ELISA kit.

Flow Cytometry Analysis and Fluorescent-Activated Cell Sorting

Cells were dissociated with TrypLE express (ThermoFisher), and DPBS (ThermoFisher) supplemented with 2% FBS (Hyclone) and 10 µM Y-27632 (Abcam) was used for antibody labelling steps and final resuspension of the samples. For HLA experiments, cells were labelled with HLA-A, B, C (W6/32) or HLA-Bw4 (1:1, Purcell lab), then AF647 goat anti-mouse IgG antibody (1:1,000, ThermoFisher), or cells were labelled with (1) HLA-G MEM-G/9 (1:500, Abcam); (2) AF488 goat anti-mouse IgG antibody (1:1,000, ThermoFisher); and (3) PE-Cy7 mouse anti-human HLA-A, B, C W6/32 (1:200, Biolegend).

scRNA-Seq of Human Reprogramming Intermediates

For scRNA-seq experiments, day 0, day 3, day 7, day 13 primed, day 13 naive, day 21 primed, day 21 naive, iPSCs primed (passage 3) and iPSCs naive (passage 3) were collected and cryopreserved. These collected samples were then subjected to FACS, for day 0, day 3, day 7, day 13 primed, day 13 naive, day 21 primed and day 21 naive samples were sorted for PI-TRA-1-85+ cells to remove dead cells and iMEF cells, and iPSCs primed (passage 3) and iPS cells naive (passage 3) samples were sorted for PI-TRA-1-85+CD13-F11R+TRA-1-60+EPCAM+ cells to get rid of dead cells and iMEF cells, as well as differentiated cells. Three samples were prepared in Extended Data FIG. 1c for subsequent library preparation, sample one contained cells isolated from day 0, 3 and 7, samples two and three contained cells for primed day 13, day 21 and iPSCs) and naive reprogramming (day 13, day 21 and iPS cells), respectively, and a small number of mixed day 0, 3 and 7 cells were added to sample two and three to capture the full reprogramming trajectories and also to account for potential batch effects. The collected cells were isolated, encapsulated and library constructed using Chromium controller (10× Genomics) as per the manufacturer's instructions (Chromium Single Cell 3' Reagent Kit V2 User Guide, 10× Genomics document number CG00052 Revision 3). A total of 12 cDNA amplification cycles were used. A total of 16 cycles of library amplification were used. Sequencing was carried out using an Illumina NextSeq 500 using SBS V2 chemistry in a high-output mode according to the recommendations outlined by 10× Genomics Chromium Single Cell 3' Reagent Kit V2 User Guide (10× Genomics document number CG00052 Revision 3), with the exception that the second read was extended to 115 bp instead of 98 bp. Libraries were diluted according to the manufacturer's instruction (NextSeq 500 System User Guide, Illumina document number 15046563 v02) and loaded at 1.8 µM. Chromium barcodes were used for demultiplexing and FASTQ files were generated from the mkfastq pipeline using the Cellranger program (v.2.1.0). Alignment and UMI counting were performed to the hg19 genome as per the snRNA-seq (except that mature mRNA was used rather than pre-mRNA, UMIs assigned to exons).

scRNA-Seq of Day-21 Fibroblast, Naive and iTSCd8 Reprogramming Intermediates

Day-21 fibroblast, naive and iTSCd8 reprogramming intermediates were collected and sorted for PI-TRA-1-85+ cells to remove dead cells and iMEF cells. The collected cells were isolated, encapsulated and constructed using Chromium controller (10× Genomics) as per the manufacturer's instructions (Chromium Next GEM Single Cell 3' Reagent Kit V3.3 User Guide). Sequencing was done on an Illumina NovaSeq 6000 using a paired-end (R1 28 bp and R2 87 bp) sequencing strategy and aiming for 20,000 read-pairs per cell. Chromium barcodes were used for demultiplexing and FASTQ files were generated from the mkfastq pipeline using the Cellranger program (v.3.1.0). Alignment and UMI counting were performed to the hg19 genome as per the scRNA-seq experiments.

Example 8: Discussion

The present results demonstrate that the transient TE state, observed during reprogramming of somatic cells, can be captured and stabilized through shifting reprogramming intermediates out of pluripotency media and into a medium that supports TSC proliferation (e.g., the TSCs media described in Okae et al, Cell Stem Cell, 2018). Remarkably, human trophoblast stem cells (TSCs) were generated during reprogramming. As such, this is the first report of a direct reprogramming from human somatic cells into TSCs.

Further characterization shows that the TSCs generated according to the present methods express key markers that define human TE and TSCs (FIG. 3). These TSCs have undergone more than 30 passages thus far without a reduction in growth rate. Moreover, functional characterisation of the TSCs, using in vitro and in vivo differentiation assays, demonstrated that the TSCs give rise to a) syncytiotrophoblasts (ST), defined SDC1+ multinucleated cells and b) extravillous trophoblasts cells (EVT), which are defined by up-regulated expression of HLA-G (key histocompatibility molecule expressed in placenta). Importantly, these assays demonstrate that the TSCs are indeed bipotential and can differentiate into ST cells and EVT cells. Altogether, these results revealed a previously undetermined extraembryonic potential of reprogramming intermediates, suggesting that cell fate specification is highly dynamic and plastic during human somatic cell reprogramming into the naive state.

Having stable, self-renewing, bona fide isogenic human iPSC and iTSC lines that can be derived from adult cells will provide the entire field with a unique opportunity to study human trophectoderm, trophoblast development, its relationship with pluripotent cells and its role in coordinating events associated with cell fate decisions in early human embryogenesis and developmental diseases in an in vitro context where modern biochemical and molecular techniques can be applied at scale.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for reprogramming a human somatic cell to a cell exhibiting at least one characteristic of a human trophoblast stem cell (TSC), the method comprising the following steps in order:

a) increasing the protein expression or amount of one or more factors in the somatic cell, wherein the factors are for reprogramming the cell towards a de-differentiated or pluripotent state;

b) culturing the cell for a sufficient time and under conditions to allow the reprogramming of the cell towards a de-differentiated or pluripotent state;

c) contacting the cell with a TSC culture medium suitable for sustaining trophoblast stem cells (TSC), wherein the cell is contacted with the TSC medium during the reprogramming process, and prior to completion of reprogramming of the cell to a pluripotent state; and d) culturing the cell in the TSC medium for a sufficient time and under conditions to allow the cell to exhibit at least one characteristic of a TSC, thereby reprogramming the somatic cell to a cell exhibiting at least one characteristic of a TSC, wherein the protein expression, or amount, of the factor(s) for reprogramming a somatic cell towards a de-differentiated or pluripotent state, is/are increased by:

contacting the cell with an agent which increases the expression of the factor, wherein the agent is selected from the group consisting of: a nucleotide sequence, a protein, an aptamer and small molecule, ribosome, RNAi agent and peptide-nucleic acid (PNA) and analogues or variants thereof; or introducing at least one nucleic acid comprising a nucleotide sequence encoding the factor, or encoding a functional fragment thereof, in the cell;

and wherein the at least one characteristic of a TSC comprises one or more of:

an undifferentiated, bipotential state;

cobblestone-shaped colony appearance;

the ability to differentiate into a cell exhibiting one or more characteristics of an extravillous trophoblast (EVT) or syncytiotrophoblast (ST);

a methylation pattern similar to a blastocyst-derived TSC, as determined by a bisulfite assay; and the expression of one or more biochemical markers of a TSC, as determined by an immunohistochemistry and/ or PCR assay.

2. The method according to claim 1, wherein the TSC culture medium comprises a growth factor, and a Rho-kinase (ROCK) inhibitor.

3. The method according to claim 1, wherein the TSC medium comprises a growth factor, and a Rho-kinase (ROCK) inhibitor and wherein the growth factor is selected from: Epidermal Growth Factor (EGF), insulin, transforming growth factor (TGF) and/or wherein the ROCK inhibitor is trans-N-(4-pyridyl)-4-(1-aminoethyl)-cyclohexanecarboxamide (Y-27632), or a salt thereof.

4. The method according to claim 1, wherein the TSC medium comprises a growth factor, and a Rho-kinase (ROCK) inhibitor and wherein the TSC culture medium additionally comprises one or more of:

4-[4-(1,3-benzodioxol-5-yl)-5-(2-pyridyl)-1H-imidazol-2-yl] benzamide (SB 431542) or a salt thereof;

6-[[2-[[4-(2,4-dichlorophenyl)-5-(4-methyl-1H-imidazol 2-yl)-2-pyrimidinyl]amino]ethyl]amino]nicotinonitrile (CHIR 99021), or a salt thereof; and/or A83-01 (3-(6-Methyl-2-pyridinyl)-N-phenyl-4-(4-quinolinyl)-1H-pyrazole-1-carbothioamide), or a salt thereof.

5. The method according to claim 1, wherein the TSC culture is ASECRiAV and comprises: A83-01, SB431542, EGF, CHIR, a ROCK inhibitor, ascorbic acid and valproic acid.

6. The method according to claim 1, wherein the somatic cell is selected from: a fibroblast, a dermal fibroblast, an epidermal cell, a keratinocyte, or a monocyte.

7. The method according to claim 1, wherein the factors for reprogramming the somatic cell towards a de-differentiated or pluripotent state, are one or more of: OCT4, SOX2, KLF4 and MYC, or wherein the factors are OCT4, SOX2, KLF4 and MYC.

8. The method according to claim 1, wherein the factors for reprogramming the somatic cell towards a de-differentiated or pluripotent state, are OCT4, SOX2, KLF4, MYC and LIN28 or, OCT4, SOX2, KLF4, MYC and NANOG, or OCT4, SOX2, KLF4, MYC, LIN28 and NANOG.

9. The method according to claim 1, wherein the somatic cell is contacted with the TSC medium at least 1 days, 2, 3, 4, 5, 6, 7, 14, 21, 28, 35, 42 or more days after increasing the protein expression or amount of one or more factors for reprogramming the somatic towards a de-differentiated or pluripotent state.

10. The method according to claim 1, wherein the somatic cell is cultured in non-pluripotent medium during the reprogramming process, and prior to being contacted with the TSC medium.

11. The method according to claim 1, wherein the step of culturing the cell for a sufficient time and under conditions to allow the reprogramming of the cell towards a de-differentiated or pluripotent state, comprises culturing the cell in media for supporting growth of the somatic cell a period of at least 7 days and no more than 22 days, wherein the somatic cell has not achieved pluripotency prior to being contacted with a TSC culture medium suitable for sustaining trophoblast stem cells (TSC).

12. The method according to claim 1, wherein the method comprises:

a) contacting somatic cells with an agent for increasing the amount or expression of OCT4, SOX2, KLF4 and MYC in the cell;

b) culturing the cells in culture medium for supporting the growth of the somatic cell, for a sufficient time and under conditions to allow the generation of reprogramming intermediate cells;

c) contacting the reprogramming intermediate cells with a TSC culture medium suitable for sustaining trophoblast stem cells (TSCs), thereby producing a cell exhibiting at least one characteristic of a TSC from a somatic cell.

13. The method according to claim 12, wherein the medium comprises A83-01, SB431542, EGF, CHIR, a ROCK inhibitor, ascorbic acid and valproic acid.

14. The method according to claim 1, wherein the somatic cell is further cultured in naïve media or extended media prior to contacting and culturing the cells with TSC medium.

15. The method of claim 1, wherein the at least one characteristic of a TSC further comprises one or more of:

the expression of one or more biochemical markers of a TSC, as determined by an immunohistochemistry and/ or PCR assay, wherein the markers are selected from the group consisting of: CD49f (iTGA6), CD249, nuclear GATA2/3, TFAP2C, P63, and NR2F2;

an absence of the markers characterising the somatic cell, optionally wherein the cell exhibiting at least one characteristic of a TSC does not express one or more of the following markers: OCT4 (also called POU5F1), NANOG, SOX2, SALL2, OTX2, BANCR, KLF17, DPPA3, ARGFX and DNMT3L;

retains its undifferentiated state when maintained in sub-culture;

the ability to differentiate into a cell exhibiting one or more characteristics of an extravillous trophoblast (EVT) or syncytiotrophoblast (ST); and expression of one or more biochemical markers of a TSC selected from the group consisting of: nuclear GATA2/3, TFAP2C, P63, and NR2F2;

and wherein the cell retains the at least one characteristic of a TSC for at least 5, at least 10, at least 15, at least 20, at least 40 or more cell culture passages.

16. The method of claim 1 wherein the method further comprises the step of differentiating the cells exhibiting at least one characteristic of a TSC to generate a cell exhibiting at least one characteristic of an EVT or an ST or to a non-placental cell type, for use in regenerative medicine.

17. A pharmaceutical composition or supplement comprising:

a cell obtained according to claim 1;

a population of cells obtained according to claim 1;

a differentiated cell or population of differentiated cells obtained according to claim 1, followed by a step of differentiation; or an organoid obtained according to the method of claim 1, or part thereof;

and a pharmaceutically acceptable excipient.

18. A method of treating and/or preventing a disorder associated with the development and/or activity of tropho-blasts in a subject in need thereof, the method comprising administering to the subject a therapeutically effective amount of:

a cell obtained according to the method of claim 1;

a population of cells obtained according to the method of claim 1;

a differentiated cell or population of differentiated cells obtained according to the method of claim 1, followed by a step of differentiation;

an organoid obtained according to the method of claim 1; or a pharmaceutical composition comprising a cell obtained according to claim 1, to a subject in need thereof, thereby treating and/or preventing the disorder associated with the development and/or activity of trophoblasts in the subject.

19. The method according to claim 1, wherein the cell exhibiting at least one characteristic of a human TSC is further introduced into a placenta or blastocyst thereby augmenting the placenta or the blastocyst.

20. The method according to claim 1, wherein the cell exhibiting at least one characteristic of a human TSC is further contacted with an agent, wherein the development and/or activity of the cell, following the contacting with the agent is compared to the development and/or activity of the cell, without the agent to identify the agent capable of modulating trophoblast development and/or activity, and wherein the effect of the agent on the development and/or activity of the cell above a predetermined level relative to the development of the cell without the agent is indicative that the agent modulates trophoblast development and/or activity.

21. The method according to claim 1, wherein the cell exhibiting at least one characteristic of a human TSC is further cultured and a compound secreted by the cells is isolated from the culture medium.

\* \* \* \* \*